US007585630B2

(12) United States Patent
Grant

(10) Patent No.: US 7,585,630 B2
(45) Date of Patent: Sep. 8, 2009

(54) GENETIC VARIANTS IN THE TCF7L2 GENE AS DIAGNOSTIC MARKERS FOR RISK OF TYPE 2 DIABETES MELLITUS

(75) Inventor: Struan F. A. Grant, Reykjavik (IS)

(73) Assignee: deCODE genetics ehf., Reykjavik (IS)

( * ) Notice: Subject to any disclaimer, the term of this patent is extended or adjusted under 35 U.S.C. 154(b) by 222 days.

(21) Appl. No.: 11/454,296

(22) Filed: Jun. 16, 2006

(65) Prior Publication Data

US 2006/0286588 A1 Dec. 21, 2006

Related U.S. Application Data

(60) Provisional application No. 60/757,155, filed on Jan. 6, 2006, provisional application No. 60/692,174, filed on Jun. 20, 2005.

(51) Int. Cl.
*C12Q 1/68* (2006.01)
*C07H 21/02* (2006.01)
(52) U.S. Cl. .......................... 435/6; 536/23.1; 536/24.3
(58) Field of Classification Search ........................ None
See application file for complete search history.

(56) References Cited

U.S. PATENT DOCUMENTS

| | | | |
|---|---|---|---|
| 6,057,117 | A | 5/2000 | Harrison et al. |
| 6,153,618 | A | 11/2000 | Schultz et al. |
| 6,417,185 | B1 | 7/2002 | Goff et al. |
| 6,465,231 | B2 | 10/2002 | Harrison et al. |
| 6,489,344 | B1 | 12/2002 | Nuss et al. |
| 6,512,102 | B1 | 1/2003 | Xu et al. |
| 6,608,063 | B2 | 8/2003 | Nuss et al. |
| 6,716,624 | B2 | 4/2004 | Harrison et al. |
| 6,762,185 | B1 | 7/2004 | Kahn et al. |
| 6,800,632 | B2 | 10/2004 | Nuss et al. |
| 2003/0008866 | A1 | 1/2003 | Nuss et al. |
| 2003/0077798 | A1 | 4/2003 | Harrison et al. |
| 2003/0130289 | A1 | 7/2003 | Nuss et al. |
| 2003/0207883 | A1 | 11/2003 | Renhowe et al. |
| 2004/0005313 | A1 | 1/2004 | Clevers et al. |
| 2004/0072831 | A1 | 4/2004 | Moon et al. |
| 2004/0092535 | A1 | 5/2004 | Barsani et al. |
| 2004/0247593 | A1 | 12/2004 | He et al. |
| 2005/0048511 | A1 | 3/2005 | Harrison et al. |
| 2005/0059628 | A1 | 3/2005 | Kahn et al. |

FOREIGN PATENT DOCUMENTS

WO  WO 03/024447  3/2003

OTHER PUBLICATIONS

Miyake, K. et al., J. Hum. Gen., vol. 53, pp. 174-180 (2008).*
Grant, S.F.A. et al., Nature Genetics, vol. 38, pp. 320-323, Supplementary Tables 3 and 4 only (2006).*
Wagman, A.S., et al., "Discovery and Development of GSK3 Inhibitors for the Treatment of Type 2 Diabetes," *Current Pharmaceutical Design*, 10: 1105-1137 (2004).
Database SNPDB ncbi, "Reference SNP (refSNP) Cluster Report rs7903146," XP002401742 (2003).
Database EMBL EBI, "HS_3076_B1_H08_MR CIT Approved Human Genomic Sperm Library D Homo sapiens Genomic Clone Plate = 3076 Col = 15 Row = P, genomic survey sequence" (1998).
Ehm, M.G., et al., "Genomewide Search for Type 2 Diabetes Susceptibility Genes in Four American Populations," *American Journal of Human Genetics*, 66: 1871-1881 (2000).
Wolfrum, C., et al., "Foxa2 Regulates Lipid Metabolism and Ketogenesis in the Liver During Fasting and in Diabetes," *Nature* 432:1027-1032 (2004).
Ross, S.E., et al., "Inhibition of Adipogenesis by Wnt Signaling," *Science*, 289:950-953 (2000).
Fasolini, M., et al., "Hot Spots in Tcf4 for the Interaction with β-Catenin," *J. Biol. Chem*. 278:21092-21098 (2003).
King, H., et al., "Global Burden of Diabetes," *Diabetes Care*, 21:1414-1431 (1998).
Noble, J.A., et al., "A Polymorphism in the TCF7 Gene, C883A, Is Associated With Type 1 Diabetes," *Diabetes*, 52:1579-1582 (2003).
Nakae, J., et al., "Regulation of Insulin Action and Pancreatic β-Cell Function by Mutated Alleles of the Gene Forkhead Transcription Factor Foxo 1," *Nature Genetics*, 32: 245-253 (2002).
Jansson, E.A., et al., "The Wnt/β-Catenin Signaliing Pathway Targets PPARγ Activity in Colon Cancer Cells," *PNAS*, 102:1460-1465 (2005).
Yi, F. et al., "TCF-4 Mediates Cell Type-Specific Regulation of Proglucagon Gene Expression by β-Catenin and Glycogen Synthase Kinase-3β," *J. Biol. Chem.*, 2:1457-1464 (2005).
Horikawa, H., et al., "Genetic Variation in the Gene Encoding Calpain-10 is Associated with Type 2 Diabetes Mellitus," *Nature Genetics*, 26: 163-175 (2000).
Gloyn, A.L., et al., "Large-Scale Association Studies of Variants in Genes Encoding the Pancreatic β-Cell $K^{ATP}$ Channel Subunits Kir6.2 (*KCNJ11*) and SUR1 (*ABCC8*) Confirm That the *KCNJ11* E23K Variant is Associated with Type 2 Diabetes," *Diabetes*, 52:568-572 (2003).
Altshuler, D., et al., "The Common PPARγPro12Ala Polymorphism is Associated with Decreased Risk of Type 2 Diabetes," *Nature Genetics*, 26:76-80 (2000).
Vilbergsson, S., et al., "Prevalence and Incidence of NIDDM in Iceland: Evidence for Stable Incidence Among Males and Femals 1967-1991-The Reykjavik Study," *Diabetic Medicine*, 14:491-498 (1997).
Fajans, S.S., et al., "Molecular Mechanisms and Clinical Pathophysiology of Maturity-Onset Diabetes of the Young," *N. Engl. J. Med.*, 345:971-980 (2001).
Gloyn, A.L., "The Search for Type 2 Diabetes Genes," *Ageing Research Reviews*, 2:111-127 (2003).

(Continued)

*Primary Examiner*—Teresa E Strzelecka
(74) *Attorney, Agent, or Firm*—Hamilton, Brook, Smith & Reynolds, P.C.

(57) ABSTRACT

Polymorphisms in the gene TCF7L2 are shown by association analysis to be a susceptibility gene for type II diabetes. Methods of diagnosis of susceptibility to diabetes, of decreased susceptibility to diabetes and protection against diabetes, are described, as are methods of treatment for type II diabetes.

13 Claims, 1 Drawing Sheet

OTHER PUBLICATIONS

Bagger, Y.Z., et al., "Risk Factors for Development of Osteoporosis and Cardiovascular Disease in Postmenopausal Danish Women: The PERF Study," *Journal of Bone and Mineral Research ASBMR 23rd Annual Meeting*, SU361, 396 (2001).

Falk, C.T. and P. Rubenstein, "Haplotype Relative Risks: An Easy Reliable Way to Construct a Proper Control Sample for Risk Calculations," *Ann. Hum. Genet.* 51:227-233 (1987).

Barnett, A.H., et al., "Diabetes in Identical Twins," *Diabetologia*, 20:87-93 (1981).

Knowler, W.C., et al., "Diabetes Mellitus in the Pima Indians: Incidence, Risk Factors and Pathogeneis," *Diabetes/Metabolism Rev.*, 6:1-27(1990).

Terwilliger, J.D., and J. Ott, "A Haplotype-Based 'Haplotype Relative Risk' Approach to Detecting Allelic Associations," *Hum. Hered.* 42:337-346 (1992).

Hill, W.G., and A. Robertson, "The Effects of Inbreeding at Loci with Heterozygote Advantage," *Genetics*, 60:615-628 (1968).

Lewontin, R.C., "The Interaction of Selection and Linkage," *Genetics*, 50:757-782 (1964).

Benson, G., "Tandem Repeats Finder: A Program to Analyze DNA Sequences," *Nucleic Acids Research*, 27:573-580 (1999).

Gulcher, J.R., et al., "Protection of Privacy by Third-Party Encryption in Genetic Research in Iceland," *Eur. Jour. Hum. Genet.* 8:739-742 (2000).

Newman, B., et al., "Concordance for Type 2 (Non-Insulin-Dependent) Diabetes Mellitus in Male Twins," *Diabetologia*, 30:763-768 (1987).

Zimmet, P., et al., "Prevalence of Diabetes and Impaired Glucose Tolerance in The Biracial (Melanesian and Indian) Population of FIJI: A Rural-Urban Comparison," *Am. Jour. Epidemiology*, 118: 673-688 (1983).

Amos, A.F., et al., "The Rising Global Burden of Diabetes and its Complications: Estimates and Projections to the Year 2010," *Diabetic Medicine*, 14:7-85 (1997).

Luu, H.H., "Wnt/β-Catenin Signaling Pathway as novel Cancer Drug Targets," *Current Cancer Drug Targets*, 4:653-671 (2004).

Cauchi, S., et al., "TCF7L2 is Reproducibly Associated with Type 2 Diabetes in Various Ethnic Groups: a Global Meta-Analysis," *J. Mol. Med.*, 85:777-782 (2007).

Florez, J.C., "The New Type 2 Diabetes Gene TCF7L2," *Curr. Opin. Clin. Nutr. Metab. Care*, 10:391-396 (2007).

Fraying, T.M., "Genome-Wide Association Studies Provide New Insights into Type 2 Diabetes Aetiology," *Nature*, 8:657-662 (2007).

Press Release "deCODE Lauches deCODE T2™ Novel DNA-Based Test for Assessing Inherited Risk of Type 2 Diabetes," Apr. 15, 2007.

Brinkmeier, M. L., et al., "TCF and Groucho-Related Genes Influence Pituitary Growth and Development," *Molecular Endocrinology* 17(11), pp. 2152-2161 (2003).

Chang, H., et al., "Genetic and Cellular Characterizations of Human TCF4 with Microsatellite Instability in Colon Cancer and Leukemia Cell Lines," *Cancer Letters*, 233 pp. 165-171 (2006).

Douglas, K. R., et al., "Identification of Members of the Wnt Signaling Pathway in the Embryonic Pituitary Gland," *Mammalian Genome*, 12, pp. 843-851 (2001).

Duval, A., et al., "Assignment[1] of the TCF-4 Gene (TCF7L2) to Human Chromosome Band 10q25.3," *Cytogenet Cell Genet*, 88, pp. 264-265 (2000).

Duval, A., et al., "The Human T-Cell Transcription Factor-4 Gene: Structure, Extensive Characterization of Alternative Splicings, and Mutational Analysis in Colorectal Cancer Cell Lines[1]," *Cancer Research*, 60, pp. 3872-3879 (2000).

Duval, A., et al., "Variable Mutation Frequencies in Coding Repeats of TCF-4 and other Target Genes in Colon, Gastric and Endometrial Carcinoma Showing Microsatellite Instability," *Oncogene*, 18, pp. 6806-6809 (1999).

Duval, A., et al., "Frequent Frameshift Mutations of the TCF-4 Gene in Colorectal Cancers with Microsatellite Instability[1]," *Cancer Research*, 59, pp. 4213-4215 (1999).

Duggirala, R., et al., "Linkage of Type 2 Diabetes Mellitus and of Age at Onset to a Genetic Location on Chromosome 10q in Mexican Americans," *Am. J. Hum. Genet.*, 64, pp. 1127-1140 (1999).

Grant, S. F. A., et al., "Variant of Transcription Factor 7-like 2 (TCF7L2) Gene Confers Risk of Type 2 Diabetes," *Nature Genetics*, 38(3), pp. 320-323 (2006).

Gu, H. F., et al., "Quantitative Trait Loci Near the Insulin-Degrading Enzyme (IDE) Gene Contribute to Variation in Plasma Insulin Levels," *Diabetes*, 53, pp. 2137-2142 (2004).

Huelsken, J., et al., "New Aspects of Wnt Signaling Pathways in Higher Vertebrates," *Curr Opin Genet Dev*, 11, pp. 547-553 (2001).

Korinek, V., et al., "Depletion of Epithelial Stem-Cell Compartments in the Small Intestine of Mice Lacking Tcf-4," *Nature Genetics*, 19, pp. 379-383 (1998).

Lepourcelet, M., et al., "Small-Molecule Antagonists of the Oncogenic Tcf/β-Catenin Protein Complex," *Cancer Cell*, 5, pp. 91-102 (2004).

Nelson, W. J., et al., "Convergence of Wnt, β-Catenin, and Cadherin Pathways," *Science*, 303, pp. 1483-1487 (2004).

Prunier C., et al., "Wnt Signaling: Physiology and Pathology," *Growth Factors*, 22(3), pp. 141-150 (2004).

Reynisdottir, I., et al., "Localization of a Susceptibility Gene for Type 2 Diabetes to Chromosome 5q34-q35.2," *Am. J. Hum. Genet.*, 73, pp. 323-335 (2003).

Rotimi, C. N., et al., "In Search of Susceptibility Genes for Type 2 Diabetes in West Africa: The Design and Results of the First Phase of the AADM Study," *Ann Epidemiol*, 11(1), pp. 51-58 (2001).

Stern, M. P., "The Search for Type 2 Diabetes Susceptibility Genes Using Whole-Genome Scans: An Epidemiologist's Perspective," *Diabetes Metab Res Rev*, 18, pp. 106-113 (2002).

Wong, N. A. C., et al., "β-Catenin-A Linchpin in Colorectal Carcinogenesis," *American Journal of Pathology*, 160(2), pp. 389-401 (2002).

\* cited by examiner

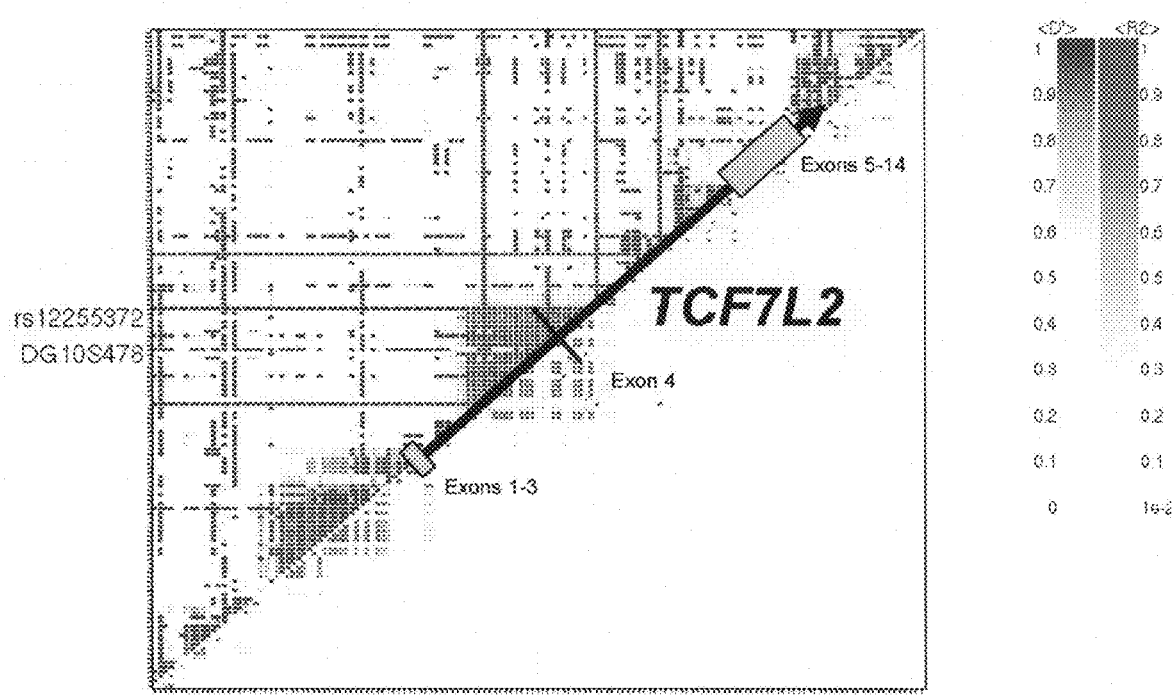

GENETIC VARIANTS IN THE TCF7L2 GENE AS DIAGNOSTIC MARKERS FOR RISK OF TYPE 2 DIABETES MELLITUS

RELATED APPLICATIONS

This application claims the benefit of U.S. Provisional Application No. 60/757,155, filed on Jan. 6, 2006 and U.S. Provisional Application No. 60/692,174, filed on Jun. 20, 2005. The entire teachings of the above applications are incorporated herein by reference.

BACKGROUND OF THE INVENTION

Diabetes mellitus, a metabolic disease wherein carbohydrate utilization is reduced and lipid and protein utilization is enhanced, is caused by an absolute or relative deficiency of insulin. In the more severe cases, diabetes is characterized by chronic hyperglycemia, glycosuria, water and electrolyte loss, ketoacidosis and coma. Long term complications include development of neuropathy, retinopathy, nephropathy, generalized degenerative changes in large and small blood vessels and increased susceptibility to infection. The most common form of diabetes is Type II, non-insulin-dependent diabetes that is characterized by hyperglycemia due to impaired insulin secretion and insulin resistance in target tissues. Both genetic and environmental factors contribute to the disease. For example, obesity plays a major role in the development of the disease. Type II diabetes is often a mild form of diabetes mellitus of gradual onset.

The health implications of Type II diabetes are enormous. In 1995, there were 135 million adults with diabetes worldwide. It is estimated that close to 300 million will have diabetes in the year 2025. (King H., et al., *Diabetes Care*, 21(9): 1414-1431 (1998)). The prevalence of Type II diabetes in the adult population in Iceland is 2.5% (Vilbergsson, S., et al., *Diabet. Med.*, 14(6): 491-498 (1997)), which comprises approximately 5,000 people over the age of 34 who have the disease. The high prevalence of the disease and increasing population affected shows an unmet medical need to define the genetic factors involved in Type II diabetes to more precisely define the associated risk factors. Also needed are therapeutic agents for prevention of Type II diabetes.

SUMMARY OF THE INVENTION

The present invention relates to methods of diagnosing an increased susceptibility to type II diabetes, as well as methods of diagnosing a decreased susceptibility to type II diabetes or diagnosing a protection against type II diabetes, by evaluating certain markers or haplotypes relating to the TCF7L2 gene (transcription factor 7-like 2 (T-cell specific, HMG-box), previously referred to as the TCF4 gene (T-cell transcription factor 4)). The methods comprise detecting a genetic marker associated with the exon 4 LD block of TCF7L2 gene.

In a first aspect, the invention relates to a method of diagnosing a susceptibility to type II diabetes in an individual, comprising analyzing a nucleic acid sample obtained from the individual for a marker or haplotype associated with the exon 4 LD block of TCF7L2, wherein the presence of the marker or haplotype is indicative of a susceptibility to type II diabetes. In one embodiment, the marker or haplotype comprises at least one marker selected from the markers listed in Table 6. In another embodiment, the marker or haplotype is a marker.

In one preferred embodiment, the marker or haplotype is indicative of increased susceptibility of type II diabetes. The increased susceptibility is in one embodiment characterized by a relative risk of at least 1.2, including a relative risk of at least 1.3 and a relative risk of at least 1.4. In one embodiment, the marker is selected from the group consisting of DG10S478, rs12255372, rs7895340, rs11196205, rs7901695, rs7903146, rs12243326, and rs4506565, and wherein the presence of a non-0 allele (e.g., −4, 4, 8, 12, 16, 20, or other non-0 allele) in DG10S478, a T allele in rs12255372; an A allele in rs7895340; a C allele in rs11196205; a C allele in rs7901695; a T allele in rs7903146; a C allele in rs12243326; or an T allele in rs4506565, is indicative of increased susceptibility to type II diabetes. In a preferred embodiment, the marker is selected from the group consisting of DG10S478 and rs7903146, and wherein the presence of a non-0 allele in DG10S478 or a T allele in rs7903146 is indicative of increased susceptibility to type II diabetes. In yet another preferred embodiment, the marker is rs7903146, and wherein the presence of a T allele in rs7903146 is indicative of increased susceptibility to type II diabetes.

In another preferred embodiment, the marker or haplotype is indicative of decreased susceptibility of type II diabetes. The decreased susceptibility is in one embodiment characterized by a relative risk of less than 0.8, including a relative risk of less than 0.7. In one embodiment, the marker is selected from the group consisting of DG10S478, rs12255372, rs7895340, rs11196205, rs7901695, rs7903146, rs2243326, and rs4506565, and wherein the presence of a 0 allele in DG10S478, a G allele in SNP rs12255372; a G allele in rs7895340; a G allele in rs11196205; a T allele in rs7901695; a C allele in rs7903146; a T allele in rs12243326; or an A allele in rs4506565 is indicative of a decreased susceptibility to type II diabetes. In a preferred embodiment, the marker is DG10S478, and wherein the presence of a 0 allele in DG10S478 is indicative of decreased susceptibility to type II diabetes. In another preferred embodiment, the marker is rs7903146, and wherein the presence of a C allele in rs7903146 is indicative of decreased susceptibility to type II diabetes.

In a second aspect, the present invention relates to a kit for assaying a sample from an individual to detect a susceptibility to type II diabetes, wherein the kit comprises one or more reagents for detecting one or more markers associated with the exon 4 LD block of TCF7L2. In one embodiment, the one or more reagents comprise at least one contiguous nucleotide sequence that is completely complementary to a region comprising at least one marker associated with the exon 4 LD block of TCF7L2. In one embodiment, the one or markers is selected from the group consisting of DG10S478, rs12255372, rs7895340, rs1196205, rs7901695, rs7903146, rs12243326, and rs4506565. In a preferred embodiment, the one or more marker is DG10S478 or rs7903146. In another preferred embodiment, the marker is the C allele in rs7903146.

In another aspect, the present invention relates to a method of assessing an individual for probability of response to a TCF7L2 therapeutic agent, comprising: detecting a marker associated with the exon 4 LD block of TCF7L2, wherein the presence of the marker is indicative of a probability of a positive response to a TCF7L2 therapeutic agent. In one embodiment, the marker is selected from the group consisting of DG10S478, rs12255372, rs7895340, rs1196205, rs7901695, rs7903146, rs12243326, and rs4506565. In another embodiment, the marker is marker DG10S478 or marker rs7903146, and wherein the presence of a non-0 allele in DG10S478 or a T allele in rs7903146 is indicative of a probability of a positive response to a TCF7L2 therapeutic agent.

Another aspect of the invention relates to the use of a TCF7L2 therapeutic agent for the manufacture of a medicament for the treatment of type II diabetes. In one embodiment, the TCF7L2 therapeutic agent is an agent that alters activity in the Wnt signaling pathway or in the cadherin pathway. In another embodiment, the TCF7L2 therapeutic agent is an agent selected from the group set forth in the Agent Table.

BRIEF DESCRIPTION OF THE DRAWINGS

The foregoing and other objects, features and advantages of the invention will be apparent from the following more particular description of preferred embodiments of the invention.

The FIGURE depicts the TCF7L2 region of interest with respect to linkage disequilibrium (LD) of SNPs in HapMap project Build 16. The 215.9 kb gene spans seven LD blocks as indicated by the black arrow schematic (based on NCBI RefSeq) which shows the direction of transcription; exons are indicated, with exon 4 highlighted. DG10S478 is located at 114.46 Mb on chromosome 10 (NCBI Build 34) in intron 3 of the TCF7L2 gene, within a 74.9 kb block that incorporates part of intron 3, the whole of exon 4 and part of intron 4 (herein referred to as the "exon 4 LD block of TCF7L2"). The SNP markers are plotted equidistantly rather than according to their physical positions. The FIGURE shows two measures of LD—i.e. D' (upper left part of FIGURE) and $r^2$ (lower right part).

DETAILED DESCRIPTION OF THE INVENTION

A description of preferred embodiments of the invention follows.

Loci Associated with Type II Diabetes

Type II diabetes is characterized by hyperglycemia, which can occur through mechanisms such as impaired insulin secretion, insulin resistance in peripheral tissues and increased glucose output by the liver. Most type II diabetes patients suffer serious complications of chronic hyperglycemia including nephropathy, neuropathy, retinopathy and accelerated development of cardiovascular disease. The prevalence of type II diabetes worldwide is currently 6% but is projected to rise over the next decade(1). This increase in prevalence of type II diabetes is attributed to increasing age of the population and rise in obesity.

There is evidence for a genetic component to the risk of type II diabetes, including prevalence differences between various racial groups(2, 3), higher concordance rates among monozygotic than dizygotic twins(4, 5) and a sibling relative risk ($\mu_s$) for type II diabetes in European populations of approximately 3.5(6).

Two approaches have thus far been used to search for genes associated with type II diabetes. Single nucleotide polymorphisms (SNPs) within candidate genes have been tested for association and have, in general, not been replicated or confer only a modest risk of type II diabetes—the most widely reported being a protective Pro12Ala polymorphism in the peroxisome proliferator activated receptor gamma gene (PPARG2)(7) and an at risk polymorphism in the potassium inwardly-rectifying channel, subfamily J, member 11 gene (KIR6.2)(8).

Genome-wide linkage scans in families with the common form of type II diabetes have yielded several loci, and the primary focus of international research consortia has been on loci on chromosomes 1, 12 and 20 observed in many populations(6). The genes in these loci have yet to be uncovered. However, in Mexican Americans, the calpain 10 (CAPN10) gene was isolated out of a locus on chromosome 2q; this represents the only gene for the common form of type II diabetes to date to be identified through positional cloning (9). The rare Mendelian forms of type II diabetes, namely maturity-onset diabetes of the young (MODY), have yielded six genes by positional cloning(6).

We previously reported genome-wide significant linkage to chromosome 5q for type II diabetes mellitus in the Icelandic population(10); in the same study, we also reported suggestive evidence of linkage to 10q and 12q. Linkage to the 10q region has also been observed in Mexican Americans(11).

Transcription Factor 7-Like 2 Gene (TCF7L2) Association with Type II Diabetes

The present invention relates to identification of a type II diabetes-associated LD block ("exon 4 LD block of TCF7L2") within the gene encoding T-cell transcription factor 4 (TCF4—official gene symbol TCF7L2). Several markers within the exon 4 LD block of TCF7L2, including microsatellite DG10S478 and SNP markers rs7903146 and rs12255372, have been found to be associated with type II diabetes. The original observation, first found in an Icelandic cohort, of the association of DG10S478 (P=1.3×10$^{-9}$; Relative risk=1.45; Population attributable risk=22.7%), has subsequently been replicated in a Danish type II diabetes cohort and a United States Caucasian cohort. DG10S478 is located in intron 3 of the TCF7L2 gene on 10q25.2 and within a well defined LD block of 74.9 kb that encapsulates part of intron 3, the whole of exon 4 and part of intron 4. The TCF7L2 gene product is a high mobility group (HMG) box-containing transcription factor that plays a role in the Wnt signaling pathway, also known as the APC3/β-catenin/TCF pathway. TCF7L2 mediates the cell type-specific regulation of proglucagon gene expression (a key player in blood glucose homeostasis) through the Wnt pathway members β-catenin and glycogen synthase kinase-3beta(12). In addition, Wnt signaling maintains preadipocytes in an undifferentiated state through inhibition of the adipogenic transcription factors CCAAT/enhancer binding protein alpha (C/EBPalpha) and peroxisome proliferator-activated receptor gamma (PPARgamma)(13). When Wnt signaling in preadipocytes is prevented by overexpression of dominant-negative TCF7L2, these cells differentiate into adipocytes(13). In addition, it has been reported that the Wnt/β-catenin signaling pathway targets PPARgamma activity through physical interaction with β-catenin and TCF7L2 in colon cancer cells(14). The multifunctional β-catenin protein is also important for mediating cell adhesion through its binding of cadherins(15).

As a result of this discovery, methods are now available for diagnosis of a susceptibility to type II diabetes, as well as for diagnosis of a decreased susceptibility to type II diabetes and/or a protection against type II diabetes. In preferred embodiments of the invention, diagnostic assays are used to identify the presence of particular alleles, including a 0 allele in marker DG10S478 (associated with a decreased susceptibility to type II diabetes and is an allele that is protective against type II diabetes); a non-0 allele (e.g., −4, 4, 8, 12, 16 or 20, or other allele) in marker DG10S478 (associated with susceptibility to type II diabetes); a G allele in SNP rs12255372 (associated with a decreased susceptibility to type II diabetes and is an allele that is protective against type II diabetes); a T allele in SNP rs12255372 (associated with susceptibility to type II diabetes); a G allele in SNP rs7895340 (associated with a decreased susceptibility to type II diabetes and is an allele that is protective against type II diabetes); an A allele in SNP rs7895340 (associated with susceptibility to type II diabetes); a G allele in SNP rs11196205 (associated with a decreased susceptibility to type II diabetes and is an allele that is protective against type II diabetes); a C allele in SNP rs11196205 (associated with susceptibility to type II diabetes); a T allele in SNP rs7901695 (associated with a decreased susceptibility to type II diabetes and is an allele that is protective against type II diabetes); a C allele in SNP rs7901695 (associated with susceptibility to type II diabetes); a C allele in SNP rs7903146 (associated with a decreased susceptibility to type II diabetes and is an allele that is protective against type II diabetes); a T allele in SNP rs7903146 (associated with a susceptibility to type II diabetes); a C allele in SNP rs12243326 (associated with a susceptibility to type II diabetes); and an T allele in SNP rs4506565 (associated with a susceptibility to type II diabetes). In additional embodiments of the invention, other markers or SNPs, identified using the methods described herein, can be used for diagnosis of a susceptibility to type II diabetes, and also for diagnosis of a decreased susceptibility to type II diabetes or for identification of an allele that is protective against type II diabetes. The diagnostic assays presented below can be used to identify the presence or absence of these particular alleles.

Diagnostic Assays

Nucleic acids, probes, primers, and antibodies such as those described herein can be used in a variety of methods of diagnosis of a susceptibility to type II diabetes, as well as in kits (e.g., useful for diagnosis of a susceptibility to type II diabetes). Similarly, the nucleic acids, probes, primers, and antibodies described herein can be used in methods of diagnosis of a decreased susceptibility to type II diabetes, as well as in methods of diagnosis of a protection against type II diabetes, and also in kits). In one aspect, the kit comprises primers that can be used to amplify the markers of interest.

In one aspect of the invention, diagnosis of a susceptibility to type II diabetes is made by detecting a polymorphism in a TCF7L2 nucleic acid as described herein (e.g., the alleles in marker DG10S478 or in SNP rs12255372, rs7895340, rs11196205, rs7901695, rs7903146, rs12243326, rs4506565). The polymorphism can be a change in a TCF7L2 nucleic acid, such as the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such change may be present in a single gene. Such sequence changes cause a difference in the polypeptide encoded by a TCF7L2 nucleic acid. For example, if the difference is a frame shift change, the frame shift can result in a change in the encoded amino acids, and/or can result in the generation of a premature stop codon, causing generation of a truncated polypeptide. Alternatively, a polymorphism associated with a disease or condition or a susceptibility to a disease or condition associated with a TCF7L2 nucleic acid can be a synonymous alteration in one or more nucleotides (i.e., an alteration that does not result in a change in the polypeptide encoded by a TCF7L2 nucleic acid). Such a polymorphism may alter splicing sites, affect the stability or transport of mRNA, or otherwise affect the transcription or translation of the gene. A TCF7L2 nucleic acid that has any of the changes or alterations described above is referred to herein as an "altered nucleic acid."

In a first method of diagnosing a susceptibility to type II diabetes, hybridization methods, such as Southern analysis, Northern analysis, or in situ hybridizations, can be used (see *Current Protocols in Molecular Biology*, Ausubel, F. et al., eds, John Wiley & Sons, including all supplements through 1999). For example, a biological sample (a "test sample") from a test subject (the "test individual") of genomic DNA, RNA, or cDNA, is obtained from an individual (RNA and cDNA can only be used for exonic markers), such as an individual suspected of having, being susceptible to or predisposed for, or carrying a defect for, type II diabetes. The individual can be an adult, child, or fetus. The test sample can be from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a polymorphism in a TCF7L2 nucleic acid is present, and/or to determine which splicing variant(s) encoded by the TCF7L2 is present. The presence of the polymorphism or splicing variant(s) can be indicated by hybridization of the gene in the genomic DNA, RNA, or cDNA to a nucleic acid probe. A "nucleic acid probe", as used herein, can be a DNA probe or an RNA probe; the nucleic acid probe can contain, for example, at least one polymorphism in a TCF7L2 nucleic acid and/or contain a nucleic acid encoding a particular splicing variant of a TCF7L2 nucleic acid. The probe can be any of the nucleic acid molecules described above (e.g., the gene or nucleic acid, a fragment, a vector comprising the gene or nucleic acid, a probe or primer, etc.).

To diagnose a susceptibility to type II diabetes, a hybridization sample can be formed by contacting the test sample containing a TCF7L2 nucleic acid with at least one nucleic acid probe. A preferred probe for detecting mRNA or genomic DNA is a labeled nucleic acid probe capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. Suitable probes for use in the diagnostic assays of the invention are described above (see e.g., probes and primers discussed under the heading, "Nucleic Acids of the Invention").

The hybridization sample is maintained under conditions that are sufficient to allow specific hybridization of the nucleic acid probe to a TCF7L2 nucleic acid. "Specific hybridization", as used herein, indicates exact hybridization (e.g., with no mismatches). Specific hybridization can be performed under high stringency conditions or moderate stringency conditions, for example, as described above. In a particularly preferred aspect, the hybridization conditions for specific hybridization are high stringency.

Specific hybridization, if present, is then detected using standard methods. If specific hybridization occurs between the nucleic acid probe and TCF7L2 nucleic acid in the test sample, then the TCF7L2 has the polymorphism, or is the splicing variant, that is present in the nucleic acid probe. More than one nucleic acid probe can also be used concurrently in this method. Specific hybridization of any one of the nucleic acid probes is indicative of a polymorphism in the TCF7L2 nucleic acid, or of the presence of a particular splicing variant encoding the TCF7L2 nucleic acid and can be diagnostic for a susceptibility to type II diabetes, or for a decreased susceptibility to type II diabetes (or indicative of a protective allele against type II diabetes).

In Northern analysis (see *Current Protocols in Molecular Biology*, Ausubel, F. et al., eds., John Wiley & Sons, supra) the hybridization methods described above are used to identify the presence of a polymorphism or a particular splicing variant, associated with a susceptibility to type II diabetes or associated with a decreased susceptibility to type II diabetes. For Northern analysis, a test sample of RNA is obtained from the individual by appropriate means. Specific hybridization of a nucleic acid probe, as described above, to RNA from the individual is indicative of a polymorphism in a TCF7L2 nucleic acid, or of the presence of a particular splicing variant encoded by a TCF7L2 nucleic acid and is therefore diagnostic for the susceptibility to type II diabetes or the decreased susceptibility to type II diabetes (or indicative of a protective allele against type II diabetes).

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry* 5, American Chemical Society, p. 1 (1994). The PNA probe can be designed to specifically hybridize to a TCF7L2 nucleic acid. Hybridization of the PNA probe to a TCF7L2 nucleic acid can be diagnostic for a susceptibility to type II diabetes or decreased susceptibility to type II diabetes (or indicative of a protective allele against type II diabetes).

In another method of the invention, alteration analysis by restriction digestion can be used to detect an alteration in the gene, if the alteration (mutation) or polymorphism in the gene results in the creation or elimination of a restriction site. A test sample containing genomic DNA is obtained from the individual. Polymerase chain reaction (PCR) can be used to amplify a TCF7L2 nucleic acid (and, if necessary, the flanking sequences) in the test sample of genomic DNA from the test individual. RFLP analysis is conducted as described (see *Current Protocols in Molecular Biology*, supra). The digestion pattern of the relevant DNA fragment indicates the presence or absence of the alteration or polymorphism in the TCF7L2 nucleic acid, and therefore indicates the presence or absence a susceptibility to type II diabetes or a decreased susceptibility to type II diabetes (or indicative of a protective allele against type II diabetes).

Sequence analysis can also be used to detect specific polymorphisms in a TCF7L2 nucleic acid. A test sample of DNA or RNA is obtained from the test individual. PCR or other appropriate methods can be used to amplify the gene or nucleic acid, and/or its flanking sequences, if desired. The sequence of a TCF7L2 nucleic acid, or a fragment of the nucleic acid, or cDNA, or fragment of the cDNA, or mRNA, or fragment of the mRNA, is determined, using standard methods. The sequence of the nucleic acid, nucleic acid fragment, cDNA, cDNA fragment, mRNA, or mRNA fragment is compared with the known nucleic acid sequence of the gene or cDNA or mRNA, as appropriate. The presence of a polymorphism in the TCF7L2 indicates that the individual has a susceptibility to type II diabetes or a decreased susceptibility to type II diabetes (or indicative of a protective allele against type II diabetes).

Allele-specific oligonucleotides can also be used to detect the presence of a polymorphism in a TCF7L2 nucleic acid, through the use of dot-blot hybridization of amplified oligonucleotides with allele-specific oligonucleotide (ASO) probes (see, for example, Saiki, R. et al., *Nature* 324:163-166 (1986)). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to a TCF7L2 nucleic acid, and that contains a polymorphism associated with a susceptibility to type II diabetes or a polymorphism associated with a decreased susceptibility to type II diabetes (or indicative of a protective allele against type II diabetes). An allele-specific oligonucleotide probe that is specific for particular polymorphisms in a TCF7L2 nucleic acid can be prepared, using standard methods (see *Current Protocols in Molecular Biology*, supra). To identify polymorphisms in the gene that are associated with type II diabetes, a test sample of DNA is obtained from the individual. PCR can be used to amplify all or a fragment of a TCF7L2 nucleic acid and its flanking sequences. The DNA containing the amplified TCF7L2 nucleic acid (or fragment of the gene or nucleic acid) is dot-blotted, using standard methods (see *Current Protocols in Molecular Biology*, supra), and the blot is contacted with the oligonucleotide probe. The presence of specific hybridization of the probe to the amplified TCF7L2 nucleic acid is then detected. Hybridization of an allele-specific oligonucleotide probe to DNA from the individual is indicative of a polymorphism in the TCF7L2 nucleic acid, and is therefore indicative of susceptibility to type II diabetes or is indicative of decreased susceptibility to type II diabetes (or indicative of a protective allele against type II diabetes).

The invention further provides allele-specific oligonucleotides that hybridize to the reference or variant allele of a gene or nucleic acid comprising a single nucleotide polymorphism or to the complement thereof. These oligonucleotides can be probes or primers.

An allele-specific primer hybridizes to a site on target DNA overlapping a polymorphism and only primes amplification of an allelic form to which the primer exhibits perfect complementarity. See Gibbs, *Nucleic Acid Res.* 17, 2427-2448 (1989). This primer is used in conjunction with a second primer, which hybridizes at a distal site. Amplification proceeds from the two primers, resulting in a detectable product, which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

With the addition of such analogs as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures of 64° C. and 74° C. when in complex with complementary DNA or RNA, respectively, as opposed to 28° C. for both DNA and RNA for the corresponding DNA nonamer. Substantial increases in $T_m$ are also obtained when LNA monomers are used in combination with standard DNA or RNA monomers. For primers and probes, depending on where the LNA monomers are included (e.g., the 3' end, the 5'end, or in the middle), the $T_m$ could be increased considerably.

In another aspect, arrays of oligonucleotide probes that are complementary to target nucleic acid sequence segments from an individual can be used to identify polymorphisms in a TCF7L2 nucleic acid. For example, in one aspect, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092. These arrays can generally be produced using mechanical synthesis methods or light directed synthesis methods that incorporate a combination of photolithographic methods and solid phase oligonucleotide synthesis methods. See Fodor et al., Science 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings are incorporated by reference herein. Techniques for the synthesis of these arrays using mechanical synthesis methods are described in, e.g., U.S. Pat. No. 5,384,261; the entire teachings are incorporated by reference herein. In another example, linear arrays can be utilized.

Once an oligonucleotide array is prepared, a nucleic acid of interest is hybridized with the array and scanned for polymorphisms. Hybridization and scanning are generally carried out by methods described herein and also in, e.g., published PCT Application Nos. WO 92/10092 and WO 95/11995, and U.S. Pat. No. 5,424,186, the entire teachings are incorporated by reference herein. In brief, a target nucleic acid sequence that includes one or more previously identified polymorphic markers is amplified by well-known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detecting a single polymorphism, arrays can include multiple detection blocks, and thus be capable of analyzing multiple, specific polymorphisms. In alternative aspects, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional uses of oligonucleotide arrays for polymorphism detection can be found, for example, in U.S. Pat. Nos. 5,858,659 and 5,837,832, the entire teachings of which are incorporated by reference herein. Other methods of nucleic acid analysis can be used to detect polymorphisms in a type II diabetes gene or variants encoded by a type II diabetes gene. Representative methods include direct manual sequencing (Church and Gilbert, Proc. Natl. Acad. Sci. USA 81:1991-1995 (1988); Sanger, F. et al., Proc. Natl. Acad. Sci. USA 74:5463-5467 (1977); Beavis et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al., Proc. Natl. Acad. Sci. USA 86:232-236 (1989)), mobility shift analysis (Orita, M. et al., Proc. Natl. Acad. Sci. USA 86:2766-2770 (1989)), restriction enzyme analysis (Flavell et al., Cell 15:25 (1978); Geever, et al., Proc. Natl. Acad. Sci. USA 78:5081 (1981)); heteroduplex analysis; chemical mismatch cleavage (CMC) (Cotton et al., Proc. Natl. Acad. Sci. USA 85:4397-4401 (1985)); RNase protection assays (Myers, R. M. et al., Science 230:1242 (1985)); use of polypeptides which recognize nucleotide mismatches, such as E. coli mutS protein; allele-specific PCR, for example.

In one aspect of the invention, diagnosis of a susceptibility to type II diabetes, or of a decreased susceptibility to type II diabetes (or indicative of a protective allele against type II diabetes), can also be made by expression analysis by quantitative PCR (kinetic thermal cycling). This technique, utilizing TaqMan® assays, can assess the presence of an alteration in the expression or composition of the polypeptide encoded by a TCF7L2 nucleic acid or splicing variants encoded by a TCF7L2 nucleic acid. TaqMan®probes can also be used to allow the identification of polymorphisms and whether a patient is homozygous or heterozygous. Further, the expression of the variants can be quantified as physically or functionally different.

In another aspect of the invention, diagnosis of a susceptibility to type II diabetes or of a decreased susceptibility to type II diabetes (or indicative of a protective allele against type II diabetes), can be made by examining expression and/or composition of a TCF7L2 polypeptide, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by a TCF7L2 nucleic acid, or for the presence of a particular variant encoded by a TCF7L2 nucleic acid. An alteration in expression of a polypeptide encoded by a TCF7L2 nucleic acid can be, for example, an alteration in the quantitative polypeptide expression (i.e., the amount of polypeptide produced); an alteration in the composition of a polypeptide encoded by a TCF7L2 nucleic acid is an alteration in the qualitative polypeptide expression (e.g., expression of an altered TCF7L2 polypeptide or of a different splicing variant). In a preferred aspect, diagnosis of a susceptibility to type II diabetes or of a decreased susceptibility to type II diabetes can be made by detecting a particular splicing variant encoded by that TCF7L2 nucleic acid, or a particular pattern of splicing variants.

Both such alterations (quantitative and qualitative) can also be present. The term "alteration" in the polypeptide expression or composition, as used herein, refers to an alteration in expression or composition in a test sample, as compared with the expression or composition of polypeptide by a TCF7L2 nucleic acid in a control sample. A control sample is a sample that corresponds to the test sample (e.g., is from the same type of cells), and is from an individual who is not affected by a susceptibility to type II diabetes. An alteration in the expression or composition of the polypeptide in the test sample, as compared with the control sample, is indicative of a susceptibility to type II diabetes. Similarly, the presence of one or more different splicing variants in the test sample, or the presence of significantly different amounts of different splicing variants in the test sample, as compared with the control sample, is indicative of a susceptibility to type II diabetes. Various means of examining expression or composition of the polypeptide encoded by a TCF7L2 nucleic acid can be used, including: spectroscopy, colorimetry, electrophoresis, isoelectric focusing, and immunoassays (e.g., David et al., U.S. Pat. No. 4,376,110) such as immunoblotting (see also *Current Protocols in Molecular Biology*, particularly Chapter 10). For example, in one aspect, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling a DNA probe with biotin such that it can be detected with fluorescently labeled streptavidin.

Western blotting analysis, using an antibody as described above that specifically binds to a polypeptide encoded by an altered TCF7L2 nucleic acid or an antibody that specifically binds to a polypeptide encoded by a non-altered nucleic acid, or an antibody that specifically binds to a particular splicing variant encoded by a nucleic acid, can be used to identify the presence in a test sample of a particular splicing variant or of a polypeptide encoded by a polymorphic or altered TCF7L2 nucleic acid, or the absence in a test sample of a particular splicing variant or of a polypeptide encoded by a non-polymorphic or non-altered nucleic acid. The presence of a polypeptide encoded by a polymorphic or altered nucleic acid, or the absence of a polypeptide encoded by a non-polymorphic or non-altered nucleic acid, is diagnostic for a susceptibility to type II diabetes, as is the presence (or absence) of particular splicing variants encoded by the TCF7L2 nucleic acid.

In one aspect of this method, the level or amount of polypeptide encoded by a TCF7L2 nucleic acid in a test sample is compared with the level or amount of the polypeptide encoded by the TCF7L2 in a control sample. A level or amount of the polypeptide in the test sample that is higher or lower than the level or amount of the polypeptide in the control sample, such that the difference is statistically significant, is indicative of an alteration in the expression of the polypeptide encoded by the TCF7L2 nucleic acid, and is diagnostic for a susceptibility to type II diabetes. Alternatively, the composition of the polypeptide encoded by a TCF7L2 nucleic acid in a test sample is compared with the composition of the polypeptide encoded by the TCF7L2 nucleic acid in a control sample (e.g., the presence of different splicing variants). A difference in the composition of the polypeptide in the test sample, as compared with the composition of the polypeptide in the control sample, is diagnostic for a susceptibility to type II diabetes. In another aspect, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of a susceptibility to type II diabetes.

The same methods can conversely be used to identify the presence of a difference when compared to a control (disease) sample. A difference from the control is indicative of a decreased susceptibility to diabetes, and/or is indicative of a protective allele against type II diabetes.

Assessment for Markers and Haplotypes

Populations of individuals exhibiting genetic diversity do not have identical genomes. Rather, the genome exhibits sequence variability between individuals at many locations in the genome; in other words, there are many polymorphic sites in a population. In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a disease or abnormal phenotype). Alleles that differ from the reference are referred to as "variant" alleles.

A "marker", as described herein, refers to a genomic sequence characteristic of a particular variant allele (i.e. polymorphic site). The marker can comprise any allele of any variant type found in the genome, including SNPs, microsatellites, insertions, deletions, duplications and translocations.

SNP nomenclature as reported herein refers to the official Reference SNP (rs) ID identification tag as assigned to each unique SNP by the National Center for Biotechnological Information (NCBI).

A "haplotype," as described herein, refers to a segment of a genomic DNA strand that is characterized by a specific combination of genetic markers ("alleles") arranged along the segment. In a certain embodiment, the haplotype can comprise one or more alleles, two or more alleles, three or more alleles, four or more alleles, or five or more alleles. The genetic markers are particular "alleles" at "polymorphic sites" associated with the exon 4 LD block of TCF7L2. As used herein, "exon 4 LD block of TCF7L2" refers to the LD block on Chr10q within which association of variants to type II diabetes is observed. NCBI Build 34 position of this LD block is from 114,413,084-114,488,013 bp. The term "susceptibility", as described herein, encompasses both increased susceptibility and decreased susceptibility. Thus, particular markers and/or haplotypes of the invention may be characteristic of increased susceptibility of type II diabetes, as characterized by a relative risk of greater than one. Markers and/or haplotypes that confer increased susceptibility of type II diabetes are furthermore considered to be "at-risk", as they confer an increased risk of disease. Alternatively, the markers and/or haplotypes of the invention are characteristic of decreased susceptibility of type II diabetes, as characterized by a relative risk of less than one.

A nucleotide position at which more than one sequence is possible in a population (either a natural population or a synthetic population, e.g., a library of synthetic molecules) is referred to herein as a "polymorphic site". Where a polymorphic site is a single nucleotide in length, the site is referred to as a single nucleotide polymorphism ("SNP"). For example, if at a particular chromosomal location, one member of a population has an adenine and another member of the population has a thymine at the same position, then this position is a polymorphic site, and, more specifically, the polymorphic site is a SNP. Alleles for SNP markers as referred to herein refer to the bases A, C, G or T as they occur at the polymorphic site in the SNP assay employed. The person skilled in the art will realise that by assaying or reading the opposite strand, the complementary allele can in each case be measured. Thus, for a polymorphic site containing an A/G polymorphism, the assay employed may either measure the percentage or ratio of the two bases possible, i.e. A and G. Alternatively, by designing an assay that determines the opposite strand on the DNA template, the percentage or ratio of the complementary bases T/C can be measured. Quantitatively (for example, in terms of relative risk), identical results would be obtained from measurement of either DNA strand (+strand or −strand). Polymorphic sites can allow for differences in sequences based on substitutions, insertions or deletions. For example, a polymorphic microsatellite has multiple small repeats of bases (such as CA repeats) at a particular site in which the number of repeat lengths varies in the general population. Each version of the sequence with respect to the polymorphic site is referred to herein as an "allele" of the polymorphic site. Thus, in the previous example, the SNP allows for both an adenine allele and a thymine allele. SNPs and microsatellite markers located within the exon 4 LD block of TCF7L2 found to be associated with type II diabetes are described in Tables 2-7.

Typically, a reference sequence is referred to for a particular sequence. Alleles that differ from the reference are referred to as "variant" alleles. For example, the reference genomic DNA sequence between positions 114413084 and 114488013 of NCBI Build 34 (equals 74929 bp, or 74.9 kb), which refers to the location within Chromosome 10, is described herein as SEQ ID NO:1. A variant sequence, as used herein, refers to a sequence that differs from SEQ ID NO:1 but is otherwise substantially similar. The genetic markers that make up the haplotypes associated with the exon 4 LD block of TCF7L2 are variants. Additional variants can include changes that affect a polypeptide, e.g., a polypeptide encoded by the TCF7L2 gene. These sequence differences, when compared to a reference nucleotide sequence, can include the insertion or deletion of a single nucleotide, or of more than one nucleotide. Such sequence differences may result in a frame shift; the change of at least one nucleotide, may result in a change in the encoded amino acid; the change of at least one nucleotide, may result in the generation of a premature stop codon; the deletion of several nucleotides, may result in a deletion of one or more amino acids encoded by the nucleotides; the insertion of one or several nucleotides, such as by unequal recombination or gene conversion, may result in an interruption of the coding sequence of a reading frame; duplication of all or a part of a sequence; transposition; or a rearrangement of a nucleotide sequence, as described in detail herein. Such sequence changes alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with type II diabetes or a susceptibility to type II diabetes can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level in tumors. The polypeptide encoded by the reference nucleotide sequence is the "reference" polypeptide with a particular reference amino acid sequence, and polypeptides encoded by variant alleles are referred to as "variant" polypeptides with variant amino acid sequences.

A polymorphic microsatellite has multiple small repeats of bases that are 2-8 nucleotides in length (such as CA repeats) at a particular site, in which the number of repeat lengths varies in the general population. An indel is a common form of polymorphism comprising a small insertion or deletion that is typically only a few nucleotides long.

The haplotypes described herein are a combination of various genetic markers, e.g., SNPs and microsatellites, having particular alleles at polymorphic sites. The haplotypes can comprise a combination of various genetic markers, therefore, detecting haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., *Genome Res.* 9(5): 492-98 (1999)), PCR, LCR, Nested PCR and other techniques for nucleic acid amplification. These markers and SNPs can be identified in at-risk haplotypes. Certain methods of identifying relevant markers and SNPs include the use of linkage disequilibrium (LD) and/or LOD scores.

In certain methods described herein, an individual who is at-risk for type II diabetes is an individual in whom an at-risk marker or haplotype is identified. In one aspect, the at-risk marker or haplotype is one that confers a significant increased risk (or susceptibility) of type II diabetes. In one embodiment, significance associated with a marker or haplotype is measured by a relative risk. In a further embodiment, the significance is measured by a percentage. In one embodiment, a significant increased risk is measured as a relative risk of at least about 1.2, including but not limited to: 1.2, 1.3, 1.4, 1.5, 1.6, 1.7, 1.8 and 1.9. In a further embodiment, a relative risk of at least 1.2 is significant. In a further embodiment, a relative risk of at least about 1.5 is significant. In a further embodiment, a significant increase in risk is at least about 1.7 is significant. In a further embodiment, a significant increase in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%.

In other embodiments of the invention, the marker or haplotype confers decreased risk (decreased susceptibility) of type II diabetes. In one embodiment, significant decreased risk is measured as a relative risk at less than 0.9, including but not limited to 0.9, 0.8, 0.7, 0.6, 0.5, and 0.4. In a further embodiment, significant relative risk is less than 0.7. In another embodiment, the decreased in risk (or susceptibility) is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant decrease in risk is at least about 30%.

Thus, the term "susceptibility to type II diabetes" indicates either an increased risk or susceptility or a decreased risk or susceptibility of type II diabetes, by an amount that is significant, when a certain allele, marker, SNP or haplotype is present; significance is measured as indicated above. The terms "decreased risk", "decreased susceptibility" and "protection against," as used herein, indicate that the relative risk is decreased accordingly when a certain other allele, marker, SNP, and/or a certain other haplotype, is present. It is understood however, that identifying whether an increased or decreased risk is medically significant may also depend on a variety of factors, including the specific disease, the marker or haplotype, and often, environmental factors.

An at-risk marker or haplotype in, or comprising portions of, the TCF7L2 gene, is one where the marker or haplotype is more frequently present in an individual at risk for type II diabetes (affected), compared to the frequency of its presence in a healthy individual (control), and wherein the presence of the marker or haplotype is indicative of susceptibility to type II diabetes. As an example of a simple test for correlation would be a Fisher-exact test on a two by two table. Given a cohort of chromosomes the two by two table is constructed out of the number of chromosomes that include both of the markers or haplotypes, one of the markers or haplotypes but not the other and neither of the markers or haplotypes.

In certain aspects of the invention, at-risk marker or haplotype is an at-risk marker or haplotype within or near TCF7L2 that significantly correlates with type II diabetes. In other aspects, an at-risk marker or haplotype comprises an at-risk marker or haplotype within or near TCF7L2 that significantly correlates with susceptibility to type II diabetes. In particular embodiments of the invention, the marker or haplotype is associated with the exon 4 LD block of TCF7L2, as described herein.

Standard techniques for genotyping for the presence of SNPs and/or microsatellite markers can be used, such as fluorescent based techniques (Chen, et al., *Genome Res.* 9, 492 (1999)), PCR, LCR, Nested PCR and other techniques for nucleic acid amplification. In a preferred aspect, the method comprises assessing in an individual the presence or frequency of SNPs and/or microsatellites in, comprising portions of, the TCF7L2 gene, wherein an excess or higher frequency of the SNPs and/or microsatellites compared to a healthy control individual is indicative that the individual is susceptible to type II diabetes. Such SNPs and markers can form haplotypes that can be used as screening tools. These markers and SNPs can be identified in at-risk haploptypes. For example, an at-risk haplotype can include microsatellite markers and/or SNPs such as marker DG10S478 and/or SNP rs12255372, rs7895340, rs11196205, rs7901695, rs7903146, rs12243326 or rs4506565. The presence of an at-risk haplotype is indicative of increased susceptibility to type II diabetes, and therefore is indicative of an individual who falls within a target population for the treatment methods described herein.

Identification of Susceptibility Variants

The frequencies of haplotypes in the patient and the control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of an significant marker and/or haplotype association.

A detailed discussion of haplotype analysis follows.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Measuring Information

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics*, 60(2):368-75 (2004)) as a natural extension of information measures defined for linkage analysis, and is implemented in NEMO.

Statistical Analysis

For single marker association to the disease, the Fisher exact test can be used to calculate two-sided p-values for each individual allele. All p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure described in Risch, N. & Teng, J. (*Genome Res.*, 8:1273-1288 (1998)), DNA pooling (ibid) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and RR² times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, risk($h_i$)/risk($h_j$)=($f_i/p_i$)/($f_j/p_j$), where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

Linkage Disequilibrium Using NEMO

LD between pairs of markers can be calculated using the standard definition of D' and $R^2$ (Lewontin, R., *Genetics* 49:49-67 (1964); Hill, W. G. & Robertson, A. *Theor. Appl. Genet.* 22:226-231 (1968)). Using NEMO, frequencies of the two marker allele combinations are estimated by maximum likelihood and deviation from linkage equilibrium is evaluated by a likelihood ratio test. The definitions of D' and $R^2$ are extended to include microsatellites by averaging over the values for all possible allele combination of the two markers weighted by the marginal allele probabilities. When plotting all marker combination to elucidate the LD structure in a particular region, we plot D' in the upper left corner and the p-value in the lower right corner. In the LD plots the markers can be plotted equidistant rather than according to their physical location, if desired.

Statistical Methods for Linkage Analysis

Multipoint, affected-only allele-sharing methods can be used in the analyses to assess evidence for linkage. Results, both the LOD-score and the non-parametric linkage (NPL) score, can be obtained using the program Allegro (Gudbjartsson et al., *Nat. Genet.* 25:12-3 (2000)). Our baseline linkage analysis uses the $S_{pairs}$ scoring function (Whittemore, A. S., Halpern, J. *Biometrics* 50:118-27 (1994); Kruglyak L. et al., *Am. J. Hum. Genet.* 58:1347-63 (1996)), the exponential allele-sharing model (Kong, A. and Cox, N. J., *Am. J. Hum. Genet.* 61:1179-88 (1997)) and a family weighting scheme that is halfway, on the log-scale, between weighting each affected pair equally and weighting each family equally. The information measure that we use is part of the Allegro program output and the information value equals zero if the marker genotypes are completely uninformative and equals one if the genotypes determine the exact amount of allele sharing by decent among the affected relatives (Gretarsdottir et al., *Am. J. Hum. Genet.*, 70:593-603 (2002)). The P-values were computed two different ways and the less significant result is reported here. The first P-value can be computed on the basis of large sample theory; the distribution of $Z_{lr}$=□(2 [$\log_e(10)$LOD]) approximates a standard normal variable under the null hypothesis of no linkage (Kong, A. and Cox, N. J., *Am. J. Hum. Genet.* 61:1179-88 (1997)). The second P-value can be calculated by comparing the observed LOD-score with its complete data sampling distribution under the null hypothesis (e.g., Gudbjartsson et al., *Nat. Genet.* 25:12-3 (2000)). When the data consist of more than a few families, these two P-values tend to be very similar.

Haplotypes and "Haplotype Block" Definition of a Susceptibility Locus

In certain embodiments, marker and haplotype analysis involves defining a candidate susceptibility locus based on "haplotype blocks" (also called "LD blocks"). It has been reported that portions of the human genome can be broken into series of discrete haplotype blocks containing a few common haplotypes; for these blocks, linkage disequilibrium data provided little evidence indicating recombination (see, e.g., Wall, J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). As used herein, the terms "haplotype block" or "LD block" includes blocks defined by either characteristic.

Representative methods for identification of haplotype blocks are set forth, for example, in U.S. Published Patent Application Nos. 20030099964, 20030170665, 20040023237 and 20040146870. Haplotype blocks can be used readily to map associations between phenotype and haplotype status. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

Haplotypes and Diagnostics

As described herein, certain markers and haplotypes comprising such markers are found to be useful for determination of susceptibility to type II diabetes—i.e., they are found to be useful for diagnosing a susceptibility to type II diabetes. Particular markers and haplotypes are found more frequently in individuals with type II diabetes than in individuals without type II diabetes. Therefore, these markers and haplotypes have predictive value for detecting type II diabetes, or a susceptibility to type II diabetes, in an individual. Haplotype blocks (i.e. the exon 4 LD block of TCF7L2) comprising certain tagging markers, can be found more frequently in individuals with type II diabetes than in individuals without type II diabetes. Therefore, these "at-risk" tagging markers within the haplotype block also have predictive value for detecting type II diabetes, or a susceptibility to type II diabetes, in an individual. "At-risk" tagging markers within the haplotype or LD blocks can also include other markers that distinguish among the haplotypes, as these similarly have predictive value for detecting type II diabetes or a susceptibility to type II diabetes. As a consequence of the haplotype block structure of the human genome, a large number of markers or other variants and/or haplotypes comprising such markers or variants in association with the haplotype block (LD block) may be found to be associated with a certain trait and/or phenotype. Thus, it is possible that markers and/or haplotypes residing within the exon 4 LD block of TCF7L2 as defined herein or in strong LD (characterized by $r^2$ greater than 0.2) with the exon 4 LD block of TCF7L2 are associated with type II diabetes (i.e. they confer increased or decreased susceptibility of type II diabetes). This includes markers that are described herein (Table 6), but may also include other markers that are in strong LD (characterized by $r^2$ greater than 0.2) with one or more of the markers listed in Table 6. The identification of such additional variants can be achieved by methods well known to those skilled in the art, for example by DNA sequencing of the LD block A genomic region in particular group of individuals, and the present invention also encompasses such additional variants.

As described herein, certain markers within the exon 4 LD block of TCF7L2 are found in decreased frequency in individuals with type II diabetes, and haplotypes comprising two or more of those markers listed in Tables 13, 20 and 21 are also found to be present at decreased frequency in individuals with type II diabetes. These markers and haplotypes are thus protective for type II diabetes, i.e. they confer a decreased risk of individuals carrying these markers and/or haplotypes developing type II diabetes.

The haplotypes and markers described herein are, in some cases, a combination of various genetic markers, e.g., SNPs and microsatellites. Therefore, detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker or haplotype associated with the exon 4 LD block of TCF7L2 is one in which the marker or haplotype is more frequently present in an individual at risk for type II diabetes (affected), compared to the frequency of its presence in a healthy individual (control), wherein the presence of the marker or haplotype is indicative of type II diabetes or a susceptibility to type II diabetes. In other embodiments, at-risk tagging markers in linkage disequilibrium with one or more markers associated with the exon 4 LD block of TCF7L2, are tagging markers that are more frequently present in an individual at risk for type II diabetes (affected), compared to the frequency of their presence in a healthy individual (control), wherein the presence of the tagging markers is indicative of increased susceptibility to type II diabetes. In a further embodiment, at-risk markers in linkage disequilibrium with one or more markers associated with the exon 4 LD block of TCF7L2, are markers that are more frequently present in an individual at risk for type II diabetes, compared to the frequency of their presence in a healthy individual (control), wherein the presence of the markers is indicative of susceptibility to type II diabetes.

In certain methods described herein, an individual who is at risk for type II diabetes is an individual in whom an at-risk marker or haplotype is identified. In one embodiment, the strength of the association of a marker or haplotype is measured by relative risk (RR). RR is the ratio of the incidence of the condition among subjects who carry one copy of the marker or haplotype to the incidence of the condition among subjects who do not carry the marker or haplotype. This ratio is equivalent to the ratio of the incidence of the condition among subjects who carry two copies of the marker or haplotype to the incidence of the condition among subjects who carry one copy of the marker or haplotype. In one embodiment, the marker or haplotype has a relative risk of at least 1.2. In other embodiments, the marker or haplotype has a relative risk of at least 1.3, at least 1.4, at least 1.5, at least 2.0, at least 2.5, at least 3.0, at least 3.5, at least 4.0, or at least 5.0.

In other methods of the invention, an individual who has a decreased risk (or deceased susceptibility) of type II diabetes is an individual in whom a protective marker or haplotype is identified. In such cases, the relative risk (RR) is less than unity. In one embodiment, the marker or haplotype has a relative risk of less than 0.9. In another embodiments, the marker or haplotype has a relative risk of less than 0.8, less than 0.7, less than 0.6, less than 0.5 or less than 0.4.

Utility of Genetic Testing

The knowledge about a genetic variant that confers a risk of developing type II diabetes offers the opportunity to apply a genetic-test to distinguish between individuals with increased risk of developing the disease (i.e. carriers of the at-risk variant) and those with decreased risk of developing the disease (i.e. carriers of the protective variant). The core values of genetic testing, for individuals belonging to both of the above mentioned groups, are the possibilities of being able to diagnose the disease at an early stage and provide information to the clinician about prognosis/aggressiveness of the disease in order to be able to apply the most appropriate treatment. For example, the application of a genetic test for type II diabetes can provide an opportunity for the detection of the disease at an earlier stage which may lead to the application of therapeutic measures at an earlier stage, and thus can minimize the deleterious effects of the symptoms and serious health consequences conferred by type II diabetes.

Methods of Therapy

In another embodiment of the invention, methods can be employed for the treatment of type II diabetes. The term "treatment" as used herein, refers not only to ameliorating symptoms associated with type II diabetes, but also preventing or delaying the onset of type II diabetes; lessening the severity or frequency of symptoms of type II diabetes; and/or also lessening the need for concomitant therapy with other drugs that ameliorate symptoms associated with type II diabetes. In one aspect, the individual to be treated is an individual who is susceptible (at an increased risk) for type II diabetes (e.g., an individual having the presence of an allele other than a 0 allele in marker DG10S478; the presence of a T allele in SNP rs12255372; the presence of an A allele in SNP rs7895340; the presence of a C allele in SNP rs11196205; the presence of a C allele in SNP rs7901695; the presence of a T allele in SNP rs7903146; the presence of a C allele in SNP rs12243326; or the presence of an T allele in SNP rs4506565.

In additional embodiments of the invention, methods can be employed for the treatment of other diseases or conditions associated with TCF7L2. A TCF7L2 therapeutic agent can be used both in methods of treatment of type II diabetes, as well as in methods of treatment of other diseases or conditions associated with TCF7L2.

The methods of treatment (prophylactic and/or therapeutic) utilize a TCF7L2 therapeutic agent. A "TCF7L2 therapeutic agent" is an agent that alters (e.g., enhances or inhibits) polypeptide activity and/or nucleic acid expression of TCF7L2, either directly or indirectly (e.g., through altering activity or nucleic acid expression of a protein that interacts with TCF7L2, such as a protein in the Wnt signaling pathway or in the cadherin pathway (e.g., beta-catenin)). In certain embodiments, the TCF7L2 therapeutic agent alters activity and/or nucleic acid expression of TCF7L2.

TCF7L2 therapeutic agents can alter TCF7L2 polypeptide activity or nucleic acid expression by a variety of means, such as, for example, by providing additional TCF7L2 polypeptide or by upregulating the transcription or translation of the TCF7L2 nucleic acid; by altering posttranslational processing of the TCF7L2 polypeptide; by altering transcription of TCF7L2 splicing variants; or by interfering with TCF7L2 polypeptide activity (e.g., by binding to a TCF7L2 polypeptide), or by binding to another polypeptide that interacts with TCF7L2, by altering (e.g., downregulating) the expression, transcription or translation of a TCF7L2 nucleic acid, or by altering (e.g., agonizing or antagonizing) activity.

Representative TCF7L2 therapeutic agents include the following: nucleic acids or fragments or derivatives thereof described herein, particularly nucleotides encoding the polypeptides described herein and vectors comprising such nucleic acids (e.g., a gene, cDNA, and/or mRNA, such as a nucleic acid encoding a TCF7L2 polypeptide or active fragment or derivative thereof, or an oligonucleotide; or a complement thereof, or fragments or derivatives thereof, and/or other splicing variants encoded by a Type II diabetes nucleic acid, or fragments or derivatives thereof); polypeptides described herein and/or splicing variants encoded by the TCF7L2 nucleic acid or fragments or derivatives thereof; other polypeptides (e.g., TCF7L2 receptors); TCF7L2 binding agents; or agents that affect (e.g., increase or decrease) activity, antibodies, such as an antibody to an altered TCF7L2 polypeptide, or an antibody to a non-altered TCF7L2 polypeptide, or an antibody to a particular splicing variant encoded by a TCF7L2 nucleic acid as described above; peptidomimetics; fusion proteins or prodrugs thereof; ribozymes; other small molecules; and other agents that alter (e.g., enhance or inhibit) expression of a TCF7L2 nucleic acid, or that regulate transcription of TCF7L2 splicing variants (e.g., agents that affect which splicing variants are expressed, or that affect the amount of each splicing variant that is expressed). Additional representative TCF7L2 therapeutic agents include compounds that influence insulin signaling and/or glucagons, GLP-1 or GIP signaling. More than one TCF7L2 therapeutic agent can be used concurrently, if desired.

In preferred embodiments, the TCF7L2 therapeutic agent is an agent that interferes with the activity of TCF7L2, such as, for example, an agent that interferes with TCF7L2 binding or interaction of TCF7L2 with beta-catenin (see, e.g., Fasolini, et al., J. Biol. Chem 278(23):21092-06 (2003)) or with other proteins. Other TCF7L2 therapeutic agents include agents that affect the Wnt signaling pathway or agents that affect the cadherin pathway. Representative agents include agents such as those used for cancer therapy, including, for example, proteins such as the DKK proteins; the beta-catenin binding domain of APC, or Axin; factors such as IDAX, AXAM and ICAT; antisense oligonucleotides or RNA interference (RNAi), such as with the use of Vitravene; oncolytic viral vectors; and other compounds (see, e.g., Luu et al., Current Cancer Drug Targets 4:6530671 (2004)); small molecule antagonists, including, for example, ZTM00990, PKF118-310, PKF118-744, PKF115-584, PKF222-815, CGPO49090, NPDDG39.024, and NPDDG1.024 as described by Lepourcelet et al. (see, e.g., Lepourcelet et al., Cancer Call 5:91-102 (2004)); compounds described in U.S. Pat. No. 6,762,185; compounds described in US Patent applications 20040005313, 20040072831, 20040247593, or 20050059628. Other representative TCF7L2 therapeutic agents include gsk3 inhibitors, including, for example, those described in U.S. Pat. Nos. 6,057,117; 6,153,618; 6,417,185; 6,465,231; 6,489,344; 6,512,102; 6,608,063; 6,716,624; 6,800,632; and published US Patent applications 20030008866; 20030077798; 20030130289; 20030207883; 2000092535; and 200500851. The entire teachings of all of the references, patents and patent applications recited in the Specification are incorporated herein in their entirety.

Additional representative TCF7L2 therapeutic agents are shown in the Agent Table, below.

Agent table

| Compound name(s) | Compound name (generated using Autonom, ISIS Draw version 2.5 from MDL Information Systems) | Company | Compound Reference | Indications |
|---|---|---|---|---|
| AR-0133418 (SN-4521) | 1-(4-Methoxy-benzyl)-3-(5-nitro-thiazol-2-yl)-urea | AstraZeneca | | AD |
| AR-025028 | NSD | AstraZeneca | | |
| CT-98023 | N-[4-(2,4-Dichloro-phenyl)-5-(1H-imidazol-2-yl)-pyrimidin-2-yl]-N'-(5-nitro-pyridin-2-yl)-ethane-1,2-diamine | Chiron Corp | Wagman et al., Curr Pharm. Des 2004: 10(10) 1105-37 | non-insulin dependent diabetes |
| CT-20026 | NSD | Chiron Corp | | non-insulin dependent diabetes |
| CT-21022 | NSD | Chiron Corp | | non-insulin dependent diabetes |
| CT-20014 | NSD | Chiron Corp | | non-insulin dependent diabetes |
| CT-21018 | NSD | Chiron Corp | | non-insulin dependent diabetes |

-continued

Agent table

| Compound name(s) | Compound name (generated using Autonom, ISIS Draw version 2.5 from MDL Information Systems) | Company | Compound Reference | Indications |
|---|---|---|---|---|
| CHIR-98025 | NSD | Chiron Corp | Wagman et al., Curr Pharm. Des 2004: 10(10) 1105-37 | non-insulin dependent diabetes |
| CHIR-99021 | NSD | Chiron Corp | | non-insulin dependent diabetes |
| | | CrystalGenomics and Yuyu | WO-2004065370 | diabetes mellitus (Korea) |
| CG-100179 | NSD | Cyclacel Ltd. | | non-insulin dependent diabetes, among others. |
| NP-01139, NP-031112, NP-03112, NP-00361 | 4-[2-(4-Dimethylamino-3-nitro-phenylamino)-pyrimidin-4-yl]-3,5-dimethyl-1H-pyrrole-2-carbonitrile | | | |
| | 4-Benzyl-2-methyl-[1,2,4]thiadiazolidine-3,5-dione | Neuropharma SA | | CNS disorders, AD |
| | 3-[9-Fluoro-2-(piperidine-1-carbonyl)-1,2,3,4-tetrahydro-[1,4]diazepino[6,7,1-hi]indol-7-yl]-4-imidazo[1,2-a]pyridin-3-yl-pyrrole-2,5-dione | Eli Lilly & Co | | non-insulin dependent diabetes |
| GW-784752x, GW-784775, SB-216763, SB-415286 | Cyclopentanecarboxylic acid (6-pyridin-3-yl-furo[2,3-d]pyrimidin-4-yl)-amide | GSK | WO-03024447 (compound referenced: 4-[2-(2-bromophenyl)-4-(4-fluorophenyl)-1H-imidazol-5-yl]pyridine | non-insulin dependent diabetes, neurodegenerative disease |
| NNC-57-0511, NNC-57-0545, NNC-57-0588 | 1-(4-Amino-furazan-3-yl)-5-piperidin-1-ylmethyl-1H-[1,2,3]triazole-4-carboxylic acid [1-pyridin-4-yl-meth-(E)-ylidene]-hydrazide | Novo Nordisk | | non-insulin dependent diabetes, |
| CP-70949 | NSD | Pfizer | | Hypoglycemic agent |
| VX-608 | NSD | | | Cerebrovascular ischemia, non-insulin dependent diabetes |
| KP-403 class | NSD | Kinetek | | Nuclear factor kappa B modulator, Anti-inflammatory, Cell cycle inhibitor, Glycogen synthase kinase-3 beta inhibitor |

-continued

Agent table

| Compound name(s) | Compound name (generated using Autonom, ISIS Draw version 2.5 from MDL Information Systems) | Company | Compound Reference | Indications |
|---|---|---|---|---|
| BYETTA (exenatide) | Exenatide: $C_{184}H_{282}N_{50}O_{60}S$ -Amino acid sequence: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ | Amylin/Eli Lilly & Co | | non-insulin dependent diabetes |
| Vildagliptin (LAF237) | NSD | Novartis | | non-insulin dependent diabetes - DPP-4 inhibitor |

NSD = No Structure disclosed (in Iddb3)

The TCF7L2 therapeutic agent(s) are administered in a therapeutically effective amount (i.e., an amount that is sufficient for "treatment," as described above). The amount which will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

In one embodiment, a nucleic acid (e.g., a nucleic acid encoding a TCF7L2 polypeptide); or another nucleic acid that encodes a TCF7L2 polypeptide or a splicing variant, derivative or fragment thereof can be used, either alone or in a pharmaceutical composition as described above. For example, a TCF7L2 gene or nucleic acid or a cDNA encoding a TCF7L2 polypeptide, either by itself or included within a vector, can be introduced into cells (either in vitro or in vivo) such that the cells produce native TCF7L2 polypeptide. If necessary, cells that have been transformed with the gene or cDNA or a vector comprising the gene, nucleic acid or cDNA can be introduced (or re-introduced) into an individual affected with the disease. Thus, cells which, in nature, lack native TCF7L2 expression and activity, or have altered TCF7L2 expression and activity, or have expression of a disease-associated TCF7L2 splicing variant, can be engineered to express the TCF7L2 polypeptide or an active fragment of the TCF7L2 polypeptide (or a different variant of the TCF7L2 polypeptide). In certain embodiments, nucleic acids encoding a TCF7L2 polypeptide, or an active fragment or derivative thereof, can be introduced into an expression vector, such as a viral vector, and the vector can be introduced into appropriate cells in an animal. Other gene transfer systems, including viral and nonviral transfer systems, can be used. Alternatively, nonviral gene transfer methods, such as calcium phosphate coprecipitation, mechanical techniques (e.g., microinjection); membrane fusion-mediated transfer via liposomes; or direct DNA uptake, can also be used.

Alternatively, in another embodiment of the invention, a nucleic acid of the invention; a nucleic acid complementary to a nucleic acid of the invention; or a portion of such a nucleic acid (e.g., an oligonucleotide as described below), can be used in "antisense" therapy, in which a nucleic acid (e.g., an oligonucleotide) which specifically hybridizes to the mRNA and/or genomic DNA of a Type II diabetes gene is administered or generated in situ. The antisense nucleic acid that specifically hybridizes to the mRNA and/or DNA inhibits expression of the TCF7L2 polypeptide, e.g., by inhibiting translation and/or transcription. Binding of the antisense nucleic acid can be by conventional base pair complementarity, or, for example, in the case of binding to DNA duplexes, through specific interaction in the major groove of the double helix.

An antisense construct of the present invention can be delivered, for example, as an expression plasmid as described above. When the plasmid is transcribed in the cell, it produces RNA that is complementary to a portion of the mRNA and/or DNA which encodes the TCF7L2 polypeptide. Alternatively, the antisense construct can be an oligonucleotide probe that is generated ex vivo and introduced into cells; it then inhibits expression by hybridizing with the mRNA and/or genomic DNA of the polypeptide. In one embodiment, the oligonucleotide probes are modified oligonucleotides, which are resistant to endogenous nucleases, e.g., exonucleases and/or endonucleases, thereby rendering them stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy are also described, for example, by Van der Krol et al., (BioTechniques 6:958-976 (1988)); and Stein et al., (Cancer Res. 48:2659-2668 (1988)). With respect to antisense DNA, oligodeoxyribonucleotides derived from the translation initiation site are preferred.

To perform antisense therapy, oligonucleotides (mRNA, cDNA or DNA) are designed that are complementary to mRNA encoding the TCF7L2 gene. The antisense oligonucleotides bind to TCF7L2 mRNA transcripts and prevent translation. Absolute complementarity, although preferred, is not required. A sequence "complementary" to a portion of an RNA, as referred to herein, indicates that a sequence has sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid, as described in detail above. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures.

The oligonucleotides used in antisense therapy can be DNA, RNA, or chimeric mixtures or derivatives or modified versions thereof, single-stranded or double-stranded. The oligonucleotides can be modified at the base moiety, sugar moiety, or phosphate backbone, for example, to improve stability of the molecule, hybridization, etc. The oligonucleotides can include other appended groups such as peptides (e.g. for targeting host cell receptors in vivo), or agents facilitating transport across the cell membrane (see, e.g., Letsinger et al., *Proc. Natl. Acad. Sci. USA* 86:6553-6556 (1989); Lemaitre et al., *Proc. Natl. Acad. Sci. USA* 84:648-652 (1987); PCT International Publication NO: WO 88/09810) or the blood-brain barrier (see, e.g., PCT International Publication NO: WO 89/10134), or hybridization-triggered cleavage agents (see, e.g., Krol et al., *BioTechniques* 6:958-976 (1988)) or intercalating agents. (See, e.g., Zon, Pharm. Res. 5:539-549 (1988)). To this end, the oligonucleotide may be conjugated to another molecule (e.g., a peptide, hybridization triggered cross-linking agent, transport agent, hybridization-triggered cleavage agent).

The antisense molecules are delivered to cells that express TCF7L2 in vivo. A number of methods can be used for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. Alternatively, in a preferred embodiment, a recombinant DNA construct is utilized in which the antisense oligonucleotide is placed under the control of a strong promoter (e.g., pol III or pol II). The use of such a construct to transfect target cells in the patient results in the transcription of sufficient amounts of single stranded RNAs that will form complementary base pairs with the endogenous TCF7L2 transcripts and thereby prevent translation of the TCF7L2 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art and described above. For example, a plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systemically).

Endogenous TCF7L2 polypeptide expression can also be reduced by inactivating or "knocking out" the gene, nucleic acid or its promoter using targeted homologous recombination (e.g., see Smithies et al., *Nature* 317:230-234 (1985); Thomas & Capecchi, *Cell* 51:503-512 (1987); Thompson et al., *Cell* 5:313-321 (1989)). For example, an altered, non-functional gene or nucleic acid (or a completely unrelated DNA sequence) flanked by DNA homologous to the endogenous gene or nucleic acid (either the coding regions or regulatory regions of the nucleic acid) can be used, with or without a selectable marker and/or a negative selectable marker, to transfect cells that express the gene or nucleic acid in vivo. Insertion of the DNA construct, via targeted homologous recombination, results in inactivation of the gene or nucleic acid. The recombinant DNA constructs can be directly administered or targeted to the required site in vivo using appropriate vectors, as described above. Alternatively, expression of non-altered genes or nucleic acids can be increased using a similar method: targeted homologous recombination can be used to insert a DNA construct comprising a non-altered functional gene or nucleic acid in place of an altered TCF7L2 in the cell, as described above. In another embodiment, targeted homologous recombination can be used to insert a DNA construct comprising a nucleic acid that encodes a Type II diabetes polypeptide variant that differs from that present in the cell.

Alternatively, endogenous TCF7L2 nucleic acid expression can be reduced by targeting deoxyribonucleotide sequences complementary to the regulatory region of a TCF7L2 nucleic acid (i.e., the TCF7L2 promoter and/or enhancers) to form triple helical structures that prevent transcription of the TCF7L2 nucleic acid in target cells in the body. (See generally, Helene, C., *Anticancer Drug Des.*, 6(6): 569-84 (1991); Helene, C. et al., *Ann. N.Y. Acad. Sci.* 660:27-36 (1992); and Maher, L. J., *Bioassays* 14(12):807-15 (1992)). Likewise, the antisense constructs described herein, by antagonizing the normal biological activity of one of the TCF7L2 proteins, can be used in the manipulation of tissue, e.g., tissue differentiation, both in vivo and for ex vivo tissue cultures. Furthermore, the anti-sense techniques (e.g., microinjection of antisense molecules, or transfection with plasmids whose transcripts are anti-sense with regard to a Type II diabetes gene mRNA or gene sequence) can be used to investigate the role of TCF7L2 or the interaction of TCF7L2 and its binding agents in developmental events, as well as the normal cellular function of TCF7L2 or of the interaction of TCF7L2 and its binding agents in adult tissue. Such techniques can be utilized in cell culture, but can also be used in the creation of transgenic animals.

In yet another embodiment of the invention, other TCF7L2 therapeutic agents as described herein can also be used in the treatment of Type II diabetes gene. The therapeutic agents can be delivered in a composition, as described above, or by themselves. They can be administered systemically, or can be targeted to a particular tissue. The therapeutic agents can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein.

A combination of any of the above methods of treatment (e.g., administration of non-altered polypeptide in conjunction with antisense therapy targeting altered mRNA of TCF7L2; administration of a first splicing variant encoded by a TCF7L2 nucleic acid in conjunction with antisense therapy targeting a second splicing encoded by a TCF7L2 nucleic acid) can also be used.

Methods of Assessing Probability of Response to TCF7L2 Therapeutic Agents

The present invention additionally pertains to methods of assessing an individual's probability of response to a TCF7L2 therapeutic agent. In the methods, markers or haplotypes relating to the TCF7L2 gene are assessed, as described above in relation to assessing an individual for susceptibility to type II diabetes. The presence of an allele, marker, SNP or haplotype associated with susceptibility (increased risk) for type II diabetes (e.g., an allele other than a 0 allele in marker DG10S478; a T allele in SNP rs12255372; an A allele in SNP rs7895340; a C allele in SNP rs11196205; a C allele in SNP rs7901695; a T allele in SNP rs7903146; a C allele in SNP rs12243326; an T allele in SNP rs4506565; a marker associated with the exon 4 LD block of TCF7L2, such as an at-risk haplotype associated with the exon 4 LD block of TCF7L2); is indicative of a probability of a positive response to a TCF7L2 therapeutic agent. "Probability of a positive response" indicates that the individual is more likely to have a positive response to a TCF7L2 therapeutic agent than an individual not having an allele, marker, SNP or haplotype associated with susceptibility (increased risk) for type II diabetes as described herein. A "positive response" to a TCF7L2 therapeutic agent is a physiological response that indicates treatment of type II diabetes. As described above, "treatment" refers not only to ameliorating symptoms associated with type II diabetes, but also preventing or delaying the onset of type II diabetes; lessening the severity or frequency of symptoms of type II diabetes; and/or also lessening the need for concomitant therapy with other drugs that ameliorate symptoms associated with type II diabetes.

Pharmaceutical Compositions

The present invention also pertains to pharmaceutical compositions comprising agents that alter TCF7L2 activity or which otherwise affect the Wnt signaling pathway or the cadherin pathway, or which can be used as TCF7L2 therapeutic agents. The pharmaceutical compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The agents are administered in a therapeutically effective amount. The amount of agents which will be therapeutically effective depends in part on the nature of the disorder and/or extent of symptoms, and can be determined by standard clinical techniques. In addition, in vitro or in vivo assays may optionally be employed to help identify optimal dosage ranges. The precise dose to be employed in the formulation will also depend on the route of administration, and the seriousness of the symptoms, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

Screening Assays and Agents Identified Thereby

The invention also provides methods for identifying agents (e.g., fusion proteins, polypeptides, peptidomimetics, prodrugs, receptors, binding agents, antibodies, small molecules or other drugs, or ribozymes) which alter (e.g., increase or decrease) the activity of the TCF7L2, which otherwise interact with TCF7L2 or with another member of the Wnt signaling pathway or the cadherin pathway (e.g., beta-catenin). For example, in certain embodiments, such agents can be agents which bind to TCF7L2; which have a stimulatory or inhibitory effect on, for example, activity of TCF7L2; or which change (e.g., enhance or inhibit) the ability of TCF7L2 to interact with other members of the Wnt signaling pathway or with members of the cadherin pathway, or which alter posttranslational processing of TCF7L2. In other embodiments, such agents can be agents which alter activity or function of the Wnt signaling pathway or the cadherin pathway.

In one embodiment, the invention provides assays for screening candidate or test agents that bind to or modulate the activity of TCF7L2 protein (or biologically active portion(s) thereof), as well as agents identifiable by the assays. Test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S., *Anticancer Drug Des.* 12:145 (1997)).

In one embodiment, to identify agents which alter the activity of TCF7L2, a cell, cell lysate, or solution containing or expressing TCF7L2, or a fragment or derivative thereof, can be contacted with an agent to be tested; alternatively, the protein can be contacted directly with the agent to be tested. The level (amount) of TCF7L2 activity is assessed (e.g., the level (amount) of TCF7L2 activity is measured, either directly or indirectly), and is compared with the level of activity in a control (i.e., the level of activity of the TCF7L2 protein or active fragment or derivative thereof in the absence of the agent to be tested). If the level of the activity in the presence of the agent differs, by an amount that is statistically significant, from the level of the activity in the absence of the agent, then the agent is an agent that alters the activity of TCF7L2. An increase in the level of activity relative to a control, indicates that the agent is an agent that enhances (is an agonist of) activity. Similarly, a decrease in the level of activity relative to a control, indicates that the agent is an agent that inhibits (is an antagonist of) activity. In another embodiment, the level of activity of TCF7L2 or a derivative or fragment thereof in the presence of the agent to be tested, is compared with a control level that has previously been established. A level of the activity in the presence of the agent that differs from the control level by an amount that is statistically significant indicates that the agent alters TCF7L2 activity.

The present invention also relates to an assay for identifying agents which alter the expression of the TCF7L2 gene (e.g., antisense nucleic acids, fusion proteins, polypeptides, peptidomimetics, prodrugs, receptors, binding agents, antibodies, small molecules or other drugs, or ribozymes) which alter (e.g., increase or decrease) expression (e.g., transcription or translation) of the gene or which otherwise interact with TCF7L2, as well as agents identifiable by the assays. For example, a solution containing a nucleic acid encoding a TCF7L2 can be contacted with an agent to be tested. The solution can comprise, for example, cells containing the nucleic acid or cell lysate containing the nucleic acid; alternatively, the solution can be another solution that comprises elements necessary for transcription/translation of the nucleic acid. Cells not suspended in solution can also be employed, if desired. The level and/or pattern of TCF7L2 expression (e.g., the level and/or pattern of mRNA or of protein expressed, such as the level and/or pattern of different splicing variants) is assessed, and is compared with the level and/or pattern of expression in a control (i.e., the level and/or pattern of the TCF7L2 expression in the absence of the agent to be tested). If the level and/or pattern in the presence of the agent differs, by an amount or in a manner that is statistically significant, from the level and/or pattern in the absence of the agent, then the agent is an agent that alters the expression of a Type II diabetes gene. Enhancement of TCF7L2 expression indicates that the agent is an agonist of TCF7L2 activity. Similarly, inhibition of TCF7L2 expression indicates that the agent is an antagonist of TCF7L2 activity. In another embodiment, the level and/or pattern of TCF7L2 polypeptide(s) (e.g., different splicing variants) in the presence of the agent to be tested, is compared with a control level and/or pattern that have previously been established. A level and/or pattern in the presence of the agent that differs from the control level and/or pattern by an amount or in a manner that is statistically significant indicates that the agent alters TCF7L2 expression.

In another embodiment of the invention, agents which alter the expression of TCF7L2 or which otherwise interact with TCF7L2 or with another member of the Wnt signaling pathway or the cadherin pathway, can be identified using a cell, cell lysate, or solution containing a nucleic acid encoding the promoter region of the TCF7L2 gene or nucleic acid operably linked to a reporter gene. After contact with an agent to be tested, the level of expression of the reporter gene (e.g., the level of mRNA or of protein expressed) is assessed, and is compared with the level of expression in a control (i.e., the level of the expression of the reporter gene in the absence of the agent to be tested). If the level in the presence of the agent differs, by an amount or in a manner that is statistically significant, from the level in the absence of the agent, then the agent is an agent that alters the expression of TCF7L2, as indicated by its ability to alter expression of a gene that is operably linked to the TCF7L2 gene promoter. Enhancement of the expression of the reporter indicates that the agent is an agonist of TCF7L2 activity. Similarly, inhibition of the expression of the reporter indicates that the agent is an antagonist of TCF7L2 activity. In another embodiment, the level of expression of the reporter in the presence of the agent to be tested is compared with a control level that has previously been established. A level in the presence of the agent that differs from the control level by an amount or in a manner that is statistically significant indicates that the agent alters expression.

Agents which alter the amounts of different splicing variants encoded by TCF7L2 (e.g., an agent which enhances activity of a first splicing variant, and which inhibits activity of a second splicing variant), as well as agents which are agonists of activity of a first splicing variant and antagonists of activity of a second splicing variant, can easily be identified using these methods described above.

In other embodiments of the invention, assays can be used to assess the impact of a test agent on the activity of a polypeptide in relation to a TCF7L2 binding agent. For example, a cell that expresses a compound that interacts with a TCF7L2 polypeptide (herein referred to as a "TCF7L2 binding agent", which can be a polypeptide or other molecule that interacts directly or indirectly with a TCF7L2 polypeptide, such as a member of the Wnt signaling pathway or a member of the cadherin pathway) is contacted with TCF7L2 in the presence of a test agent, and the ability of the test agent to alter the interaction between the TCF7L2 and the TCF7L2 binding agent is determined. Alternatively, a cell lysate or a solution containing the TCF7L2 binding agent, can be used. An agent that binds to the TCF7L2 or the TCF7L2 binding agent can alter the interaction by interfering with, or enhancing the ability of the TCF7L2 to bind to, associate with, or otherwise interact with the TCF7L2 binding agent. Determining the ability of the test agent to bind to TCF7L2 or a TCF7L2 binding agent can be accomplished, for example, by coupling the test agent with a radioisotope or enzymatic label such that binding of the test agent to the polypeptide can be determined by detecting the labeled with $^{125}I$, $^{35}H$, $^{14}C$ or $^{3}H$, either directly or indirectly, and the radioisotope detected by direct counting of radioemission or by scintillation counting. Alternatively, test agents can be enzymatically labeled with, for example, horseradish peroxidase, alkaline phosphatase, or luciferase, and the enzymatic label detected by determination of conversion of an appropriate substrate to product. It is also within the scope of this invention to determine the ability of a test agent to interact with the polypeptide without the labeling of any of the interactants. For example, a microphysiometer can be used to detect the interaction of a test agent with TCF7L2 or a TCF7L2 binding agent without the labeling of either the test agent, TCF7L2, or the TCF7L2 binding agent. McConnell, H. M. et al., Science 257:1906-1912 (1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

Thus, these receptors can be used to screen for compounds that are agonists or antagonists, for use in treating or studying a susceptibility to type II diabetes. Drugs could be designed to regulate TCF7L2 activation that in turn can be used to regulate signaling pathways and transcription events of genes downstream.

In another embodiment of the invention, assays can be used to identify polypeptides that interact with TCF7L2. For example, a yeast two-hybrid system such as that described by Fields and Song (Fields, S. and Song, O., Nature 340:245-246 (1989)) can be used to identify polypeptides that interact with TCF7L2. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used which includes a nucleic acid encoding a DNA binding domain and also TCF7L2, splicing variant, or fragment or derivative thereof, and a second vector is used which includes a nucleic acid encoding a transcription activation domain and also a nucleic acid encoding a polypeptide which potentially may interact with TCF7L2 or a splicing variant, or fragment or derivative thereof. Incubation of yeast containing the first vector and the second vector under appropriate conditions (e.g., mating conditions such as used in the Matchmaker™ system from Clontech (Palo Alto, Calif., USA)) allows identification of colonies that express the markers of interest. These colonies can be examined to identify the polypeptide(s) that interact with TCF7L2 or fragment or derivative thereof. Such polypeptides can be used as agents that alter the activity of expression of TCF7L2, as described in relation to methods of treatment.

In more than one embodiment of the above assay methods of the present invention, it may be desirable to immobilize either the TCF7L2 gene, the TCF7L2 protein, the TCF7L2 binding agent (e.g., another member of the Wnt signaling pathway or member of the cadherin pathway), or other components of the assay on a solid support, in order to facilitate separation of complexed from uncomplexed forms of one or both of the proteins, as well as to accommodate automation of the assay. Binding of a test agent to the protein, or interaction of the protein with a binding agent in the presence and absence of a test agent, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided which adds a domain that allows TCF7L2, TCF7L2 protein, or a TCF7L2 binding agent to be bound to a matrix or other solid support.

In another embodiment, modulators of expression of nucleic acid molecules of the invention are identified in a method wherein a cell, cell lysate, or solution containing TCF7L2 is contacted with a test agent and the expression of appropriate mRNA or polypeptide (e.g., splicing variant(s)) in the cell, cell lysate, or solution, is determined. The level of expression of appropriate mRNA or polypeptide(s) in the presence of the test agent is compared to the level of expression of mRNA or polypeptide(s) in the absence of the test agent. The test agent can then be identified as a modulator of expression based on this comparison. For example, when expression of mRNA or polypeptide is greater (statistically significantly greater) in the presence of the test agent than in its absence, the test agent is identified as a stimulator or enhancer of the mRNA or polypeptide expression. Alternatively, when expression of the mRNA or polypeptide is less (statistically significantly less) in the presence of the test agent than in its absence, the test agent is identified as an inhibitor of the mRNA or polypeptide expression. The level of mRNA or polypeptide expression in the cells can be determined by methods described herein for detecting mRNA or polypeptide.

This invention further pertains to novel agents identified by the above-described screening assays. Accordingly, it is within the scope of this invention to further use an agent identified as described herein in the methods of treatment described herein. For example, an agent identified as described herein can be used to alter activity of a protein encoded by a TCF7L2 gene, or to alter expression of TCF7L2 by contacting the protein or the nucleic acid (or contacting a cell comprising the polypeptide or the nucleic acid) with the agent identified as described herein.

Nucleic Acids of the Invention

TCF7L2 Nucleic Acids, Portions and Variants

The present invention also pertains to isolated nucleic acid molecules comprising human TCF7L2. The TCF7L2 nucleic acid molecules of the present invention can be RNA, for example, mRNA, or DNA, such as cDNA and genomic DNA. DNA molecules can be double-stranded or single-stranded; single stranded RNA or DNA can be the coding, or sense, strand or the non-coding, or antisense strand. The nucleic acid molecule can include all or a portion of the coding sequence of the gene and can further comprise additional non-coding sequences such as introns and non-coding 3' and 5' sequences (including regulatory sequences, for example).

Additionally, nucleic acid molecules of the invention can be fused to a marker sequence, for example, a sequence that encodes a polypeptide to assist in isolation or purification of the polypeptide. Such sequences include, but are not limited to, those that encode a glutathione-5-transferase (GST) fusion protein and those that encode a hemagglutinin A (HA) polypeptide marker from influenza.

An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid molecule comprises at least about 50, 80 or 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 5 kb but not limited to 4 kb, 3 kb, 2 kb, 1 kb, 0.5 kb or 0.1 kb of nucleotides which flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule can include a nucleic acid molecule or nucleic acid sequence that is synthesized chemically or by recombinant means. Therefore, recombinant DNA contained in a vector is included in the definition of "isolated" as used herein. Also, isolated nucleic acid molecules include recombinant DNA molecules in heterologous organisms, as well as partially or substantially purified DNA molecules in solution. In vivo and in vitro RNA transcripts of the DNA molecules of the present invention are also encompassed by "isolated" nucleic acid sequences. Such isolated nucleic acid molecules are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern or Southern blot analysis.

The present invention also pertains to nucleic acid molecules which are not necessarily found in nature but which encode a TCF7L2 polypeptide, or another splicing variant of a TCF7L2 polypeptide or polymorphic variant thereof. Thus, for example, the invention pertains to DNA molecules comprising a sequence that is different from the naturally occurring nucleotide sequence but which, due to the degeneracy of the genetic code, encode a TCF7L2 polypeptide of the present invention. The invention also encompasses nucleic acid molecules encoding portions (fragments), or encoding variant polypeptides such as analogues or derivatives of a TCF7L2 polypeptide. Such variants can be naturally occurring, such as in the case of allelic variation or single nucleotide polymorphisms, or non-naturally-occurring, such as those induced by various mutagens and mutagenic processes. Intended variations include, but are not limited to, addition, deletion and substitution of one or more nucleotides that can result in conservative or non-conservative amino acid changes, including additions and deletions. Preferably the nucleotide (and/or resultant amino acid) changes are silent or conserved; that is, they do not alter the characteristics or activity of a TCF7L2 polypeptide. In one aspect, the nucleic acid sequences are fragments that comprise one or more polymorphic microsatellite markers. In another aspect, the nucleotide sequences are fragments that comprise one or more single nucleotide polymorphisms in a TCF7L2 gene.

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

The invention also pertains to nucleic acid molecules that hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). In one aspect, the invention includes variants described herein that hybridize under high stringency hybridization conditions (e.g., for selective hybridization) to a nucleotide sequence encoding an amino acid sequence or a polymorphic variant thereof. In another aspect, the variant that hybridizes under high stringency hybridizations has an activity of a TCF7L2 polypeptide.

Such nucleic acid molecules can be detected and/or isolated by specific hybridization (e.g., under high stringency conditions). "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 85%, 90%, 95%). For example, certain high stringency conditions can be used which distinguish perfectly complementary nucleic acids from those of less complementarity. "High stringency conditions", "moderate stringency conditions" and "low stringency conditions", as well as methods for nucleic acid hybridizations are explained on pages 2.10.1-2.10.16 and pages 6.3.1-6.3.6 in *Current Protocols in Molecular Biology* (Ausubel, F. et al., "*Current Protocols in Molecular Biology*", John Wiley & Sons, (1998)), and in Kraus, M. and Aaronson, S., *Methods Enzymol.*, 200:546-556 (1991), The percent homology or identity of two nucleotide or amino acid sequences can be determined by aligning the sequences for optimal comparison purposes (e.g., gaps can be introduced in the sequence of a first sequence for optimal alignment). The nucleotides or amino acids at corresponding positions are then compared, and the percent identity between the two sequences is a function of the number of identical positions shared by the sequences (i.e., % identity=# of identical positions/total # of positions×100). When a position in one sequence is occupied by the same nucleotide or amino acid residue as the corresponding position in the other sequence, then the molecules are homologous at that position. As used herein, nucleic acid or amino acid "homology" is equivalent to nucleic acid or amino acid "identity". In certain aspects, the length of a sequence aligned for comparison purposes is at least 30%, for example, at least 40%, in certain aspects at least 60%, and in other aspects at least 70%, 80%, 90% or 95% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA* 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., W=5 or W=20).

Another preferred non-limiting example of a mathematical algorithm utilized for the comparison of sequences is the algorithm of Myers and Miller, *CABIOS* 4(1): 11-17 (1988). Such an algorithm is incorporated into the ALIGN program (version 2.0) which is part of the GCG sequence alignment software package (Accelrys, Cambridge, UK). When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, *Comput. Appl. Biosci.* 10:3-5 (1994); and FASTA described in Pearson and Lipman, *Proc. Natl. Acad. Sci. USA* 85:2444-8 (1988).

In another aspect, the percent identity between two amino acid sequences can be accomplished using the GAP program in the GCG software package using either a BLOSUM63 matrix or a PAM250 matrix, and a gap weight of 12, 10, 8, 6, or 4 and a length weight of 2, 3, or 4. In yet another aspect, the percent identity between two nucleic acid sequences can be accomplished using the GAP program in the GCG software package using a gap weight of 50 and a length weight of 3.

The present invention also provides isolated nucleic acid molecules that contain a fragment or portion that hybridizes under highly stringent conditions to a nucleotide sequence of TCF7L2, or the complement of such a sequence, and also provides isolated nucleic acid molecules that contain a fragment or portion that hybridizes under highly stringent conditions to a nucleotide sequence encoding an amino acid sequence or polymorphic variant thereof. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic polypeptides described herein, are particularly useful, such as for the generation of antibodies as described below.

Probes and Primers

In a related aspect, the nucleic acid fragments of the invention are used as probes or primers in assays such as those described herein. "Probes" or "primers" are oligonucleotides that hybridize in a base-specific manner to a complementary strand of nucleic acid molecules. Such probes and primers include polypeptide nucleic acids, as described in Nielsen et al., *Science* 254:1497-1500 (1991).

A probe or primer comprises a region of nucleotide sequence that hybridizes to at least about 15, for example about 20-25, and in certain aspects about 40, 50 or 75, consecutive nucleotides of a nucleic acid molecule comprising a contiguous nucleotide sequence of TCF7L2 or polymorphic variant thereof. In other aspects, a probe or primer comprises 100 or fewer nucleotides, in certain aspects from 6 to 50 nucleotides, for example from 12 to 30 nucleotides. In other aspects, the probe or primer is at least 70% identical to the contiguous nucleotide sequence or to the complement of the contiguous nucleotide sequence, for example at least 80% identical, in certain aspects at least 90% identical, and in other aspects at least 95% identical, or even capable of selectively hybridizing to the contiguous nucleotide sequence or to the complement of the contiguous nucleotide sequence. Often, the probe or primer further comprises a label, e.g., radioisotope, fluorescent compound, enzyme, or enzyme co-factor.

The nucleic acid molecules of the invention such as those described above can be identified and isolated using standard molecular biology techniques and the sequence information provided herein. For example, nucleic acid molecules can be amplified and isolated by the polymerase chain reaction using synthetic oligonucleotide primers designed based on the sequence of TCF7L2 or the complement of such a sequence, or designed based on nucleotides based on sequences encoding one or more of the amino acid sequences provided herein. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis et al., Academic Press, San Diego, Calif., 1990); Mattila et al., *Nucl. Acids Res.* 19: 4967 (1991); Eckert et al., *PCR Methods and Applications* 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), and self-sustained sequence replication (Guatelli et al., *Proc. Nat. Acad. Sci. USA* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be labeled, for example, radiolabeled, and used as a probe for screening a cDNA library derived from human cells, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a polypeptide of the appropriate molecular weight. For example, the direct analysis of the nucleotide sequence of nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Additionally, fluorescence methods are also available for analyzing nucleic acids (Chen et al., *Genome Res.* 9, 492 (1999)) and polypeptides. Using these or similar methods, the polypeptide and the DNA encoding the polypeptide can be isolated, sequenced and further characterized.

Antisense nucleic acid molecules of the invention can be designed using the nucleotide sequence of TCF7L2 and/or the complement or a portion, and constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

The nucleic acid sequences can also be used to compare with endogenous DNA sequences in patients to identify one or more of the disorders described above, and as probes, such as to hybridize and discover related DNA sequences or to subtract out known sequences from a sample. The nucleic acid sequences can further be used to derive primers for genetic fingerprinting, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways, such as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Additionally, the nucleotide sequences of the invention can be used to identify and express recombinant polypeptides for analysis, characterization or therapeutic use, or as markers for tissues in which the corresponding polypeptide is expressed, either constitutively, during tissue differentiation, or in diseased states. The nucleic acid sequences can additionally be used as reagents in the screening and/or diagnostic assays described herein, and can also be included as components of kits (e.g., reagent kits) for use in the screening and/or diagnostic assays described herein.

Kits (e.g., reagent kits) useful in the methods of diagnosis comprise components useful in any of the methods described herein, including for example, hybridization probes or primers as described herein (e.g., labeled probes or primers), reagents for detection of labeled molecules, restriction enzymes (e.g., for RFLP analysis), allele-specific oligonucleotides, antibodies which bind to altered or to non-altered (native) TCF7L2 polypeptide, means for amplification of nucleic acids comprising a TCF7L2 nucleic acid or for a portion of TCF7L2, or means for analyzing the nucleic acid sequence of a TCF7L2 nucleic acid or for analyzing the amino acid sequence of a TCF7L2 polypeptide as described herein, etc. In one aspect, the kit for diagnosing a susceptibility to type II diabetes can comprise primers for nucleic acid amplification of a region in the TCF7L2 nucleic acid comprising the marker DG10S478, the SNP rs12255372, rs895340, rs 1196205, rs7901695, rs7903146, rs12243326 and/or rs4506565, or an at-risk haplotype that is more frequently present in an individual having type II diabetes or who is susceptible to type II diabetes. The primers can be designed using portions of the nucleic acids flanking SNPs that are indicative of type II diabetes.

Vectors and Host Cells

Another aspect of the invention pertains to nucleic acid constructs containing a nucleic acid molecules described herein and the complements thereof (or a portion thereof). The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Expression vectors are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

In certain aspects, recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" or "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, "Gene Expression Technology", *Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al., (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture can be used to produce (i.e., express) a polypeptide of the invention. Accordingly, the invention further provides methods for producing a polypeptide using the host cells of the invention. In one aspect, the method comprises culturing the host cell of invention (into which a recombinant expression vector encoding a polypeptide of the invention has been introduced) in a suitable medium such that the polypeptide is produced. In another aspect, the method further comprises isolating the polypeptide from the medium or the host cell.

Antibodies of the Invention

Polyclonal antibodies and/or monoclonal antibodies that specifically bind one form of the gene product but not to the other form of the gene product are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the *Pharmacia Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The present invention is now illustrated by the following Exemplification, which is not intended to be limiting in any way.

Exemplification

Described herein is the identification of transcription factor 7-like 2 (TCF7L2-formerly TCF4) as a gene conferring risk of type II diabetes through single-point association analysis using a dense set of microsatellite markers within the 10q locus.

Methods

Icelandic Cohort

The Data Protection Authority of Iceland and the National Bioethics Committee of Iceland approved the study. All participants in the study gave informed consent. All personal identifiers associated with blood samples, medical information, and genealogy were first encrypted by the Data Protection Authority, using a third-party encryption system (18).

For this study, 2400 type II diabetes patients were identified who were diagnosed either through a long-term epidemiologic study done at the Icelandic Heart Association over the past 30 years or at one of two major hospitals in Reykjavik over the past 12 years. Two-thirds of these patients were alive, representing about half of the population of known type II diabetes patients in Iceland today. The majority of these patients were contacted for this study, and the cooperation rate exceeded 80%. All participants in the study visited the Icelandic Heart Association where they answered a questionnaire, had blood drawn and a fasting plasma glucose measurements taken. Questions about medication and age at diagnosis were included. The type II diabetes patients in this study were diagnosed as described in our previously published linkage study(10). In brief, the diagnosis of type II diabetes was confirmed by study physicians through previous medical records, medication history, and/or new laboratory measurements. For previously diagnosed type II diabetes patients, reporting of the use of oral glucose-lowering agent confirmed type II diabetes. Individuals who were currently treated with insulin were classified as having type II diabetes if they were also using or had previously used oral glucose-lowering agents. In this cohort the majority of patients on medication take oral glucose-lowering agents and only a small portion (9%) require insulin. For hitherto undiagnosed individuals, the diagnosis of type II diabetes and impaired fasting glucose (IFG) was based on the criteria set by the American Diabetes Association (Expert Committee on the Diagnosis and Classification of Diabetes Mellitus 1997). The average age of the type II diabetes patients in this study was 69.7 years.

Replication Cohorts

The Danish study group was selected from the PERF (Prospective Epidemiological Risk Factors) study in Denmark (19). 228 females had been diagnosed previously with type II diabetes and/or measured >=7 mM glucose. As controls, 539 unaffected (with respect to type II diabetes) females were randomly drawn from the same study cohort.

The PENN CATH study in the US is a cross sectional study of the association of biochemical and genetic factors with coronary atherosclerosis in a consecutive cohort of patients undergoing cardiac catheterization at the University of Pennsylvania Medical Center between July 1998 and March 2003. Type II diabetes was defined as history of fasting blood glucose $\geq$126 mg/dl, 2-hour post-prandial glucose $\geq$200 mg/dl, use of oral hypoglycemic agents, or insulin and oral hypoglycemic in a subject greater than age 40. The University of Pennsylvania Institutional Review Board approved the study protocol and all subjects gave written informed consent. Ethnicity was determined through self-report. 361 Caucasian type II diabetes cases were derived from this cohort. 530 unaffected (with respect to type II diabetes and myocardial infarction) Caucasian controls were randomly drawn from the same study.

The DNA used for genotyping was the product of whole-genome amplification, by use of the GenomiPhi Amplification kit (Amersham), of DNA isolated from the peripheral blood of the Danish and US type II diabetes patients and controls.

Genotyping

New sequence repeats (i.e. dinucleotide, trinucleotide, and tetronucleotide repeats) were identified using the Tandem repeats finder software(20) and tested for polymorphicity in 94 controls. The size in basepairs of the lower allele of the CEPH sample 1347-02 (CEPH genomics repository) was subtracted from the size of the microsatellite amplicon and used as a reference. SNP genotyping was carried using direct DNA sequencing (Applied BioSystems) or the Centaurus platform (Nanogen).

Statistical Methods for Association Analysis

For single marker association to type II diabetes, we used a likelihood ratio test to calculate a two-sided p-value for each allele. We present allelic frequencies rather than carrier frequencies for the microsatellites employed.

We calculated relative risk (RR) and population attributable risk (PAR) assuming a multiplicative model(16, 17). For the CEPH Caucasian HapMap data, we calculated LD between pairs of SNPs using the standard definition of D' (21) and $R^2$ (22). When plotting all SNP combinations to elucidate the LD structure in a particular region, we plotted D' in the upper left corner and p-values in the lower right corner. In the LD plot we present, the markers are plotted equidistantly rather than according to their physical positions.

Results

Locus-wide Association Study

We previously reported genome-wide significant linkage to chromosome 5q for type II diabetes mellitus in the Icelandic population(10); in the same study, we also reported suggestive evidence of linkage to 10q and 12q. To follow up the 10q locus, we used an association approach employing a high density of genotyped microsatellite markers across a 10.5 Mb region (NCBI Build 34: Chr10:114.2-124.7 Mb) corresponding to this locus. We identified and typed 228 microsatellite markers—i.e. to an average density of one marker every 46 kb (Table 1). All the markers were typed in 1185 Icelandic type II diabetes patients and 931 unrelated population controls.

TABLE 1

Location of the 228 genotyped microsatellites on chromosome 10 in NCBI Build 34 of the human genome assembly.

| Alias | START: Build 34 Chr10 location | END: Build 34 Chr10 location |
|---|---|---|
| D10S1269 | 114186051 | 114186276 |
| DG10S475 | 114389853 | 114390116 |
| D10S168 | 114410102 | 114410266 |
| DG10S478 | 114460845 | 114461228 |
| DG10S479 | 114475488 | 114475632 |
| DG10S480 | 114507574 | 114507829 |
| DG10S481 | 114542657 | 114542924 |
| DG10S1624 | 114545990 | 114546237 |
| DG10S1625 | 114568323 | 114568715 |
| DG10S488 | 114713594 | 114714008 |
| DG10S1630 | 114770344 | 114770609 |
| DG10S1631 | 114778307 | 114778598 |
| DG10S492 | 114811884 | 114812269 |
| DG10S494 | 114852114 | 114852280 |
| DG10S495 | 114879344 | 114879474 |
| DG10S496 | 114919414 | 114919678 |
| DG10S498 | 114964123 | 114964270 |
| DG10S500 | 115024471 | 115024854 |
| DG10S501 | 115045332 | 115045710 |
| DG10S508 | 115241356 | 115241602 |
| DG10S1634 | 115267106 | 115267460 |
| DG10S512 | 115357290 | 115357439 |
| DG10S514 | 115400157 | 115400338 |
| DG10S17 | 115463773 | 115464048 |
| DG10S1635 | 115519619 | 115519900 |
| DG10S520 | 115536945 | 115537130 |
| D10S554 | 115695920 | 115696071 |
| D10S1237 | 115784580 | 115784977 |
| DG10S535 | 115858565 | 115858720 |
| D10S1158 | 115937134 | 115937433 |
| DG10S1636 | 115966165 | 115966382 |
| DG10S540 | 115983225 | 115983471 |
| DG10S1637 | 116025219 | 116025491 |
| DG10S542 | 116054130 | 116054255 |
| DG10S1638 | 116062921 | 116063264 |
| D10S1776 | 116140681 | 116140897 |
| DG10S546 | 116141340 | 116141590 |
| DG10S547 | 116173634 | 116173887 |
| DG10S1639 | 116184720 | 116184898 |
| DG10S548 | 116202775 | 116203174 |
| DG10S550 | 116288175 | 116288560 |
| D10S562 | 116304948 | 116305132 |
| DG10S1640 | 116344030 | 116344279 |
| DG10S1641 | 116638155 | 116638540 |
| DG10S566 | 116866173 | 116866431 |
| D10S468 | 116869582 | 116869674 |
| DG10S567 | 116904174 | 116904433 |
| D10S1731 | 117001692 | 117001870 |
| DG10S573 | 117070087 | 117070192 |
| DG10S576 | 117153566 | 117153823 |
| DG10S578 | 117196538 | 117196813 |
| DG10S1644 | 117206992 | 117207391 |
| DG10S579 | 117226056 | 117226234 |
| DG10S580 | 117240674 | 117240858 |
| DG10S584 | 117336471 | 117336821 |
| DG10S585 | 117364742 | 117364845 |
| DG10S586 | 117385650 | 117385816 |
| DG10S589 | 117481892 | 117482165 |
| DG10S590 | 117508690 | 117508966 |
| DG10S591 | 117520912 | 117521057 |
| DG10S593 | 117567541 | 117567800 |
| D10S1748 | 117589638 | 117589885 |
| DG10S596 | 117629981 | 117630119 |
| DG10S597 | 117654759 | 117654928 |
| DG10S523 | 117691905 | 117692329 |
| DG10S598 | 117691905 | 117692156 |
| D10S1773 | 117708786 | 117708989 |
| DG10S599 | 117713714 | 117714115 |
| DG10S524 | 117713997 | 117714115 |
| DG10S600 | 117742602 | 117743019 |
| DG10S525 | 117742701 | 117742986 |
| DG10S1250 | 117861226 | 117861405 |
| DG10S604 | 117867801 | 117868010 |

TABLE 1-continued

Location of the 228 genotyped microsatellites on chromosome 10 in NCBI Build 34 of the human genome assembly.

| Alias | START: Build 34 Chr10 location | END: Build 34 Chr10 location |
|---|---|---|
| DG10S1293 | 117932494 | 117932721 |
| DG10S1144 | 117950298 | 117950606 |
| DG10S609 | 118014503 | 118014752 |
| DG10S610 | 118041410 | 118041787 |
| DG10S1252 | 118085912 | 118086081 |
| DG10S612 | 118092869 | 118093247 |
| DG10S613 | 118126058 | 118126312 |
| DG10S614 | 118150018 | 118150178 |
| D10S544 | 118164684 | 118164979 |
| D10S1683 | 118211053 | 118211180 |
| D10S1657 | 118287426 | 118287695 |
| D10S545 | 118299618 | 118299851 |
| DG10S1649 | 118306954 | 118307121 |
| D10S187 | 118317655 | 118317730 |
| DG10S1295 | 118375973 | 118376205 |
| DG10S624 | 118401694 | 118402073 |
| DG10S1203 | 118440472 | 118440835 |
| DG10S627 | 118514695 | 118515072 |
| DG10S1650 | 118521021 | 118521210 |
| DG10S1681 | 118522946 | 118523333 |
| DG10S628 | 118553693 | 118553836 |
| DG10S634 | 118566844 | 118567191 |
| DG10S639 | 118712208 | 118712596 |
| DG10S640 | 118743450 | 118743821 |
| D10S221 | 118766458 | 118766560 |
| DG10S1686 | 118766464 | 118766561 |
| DG10S641 | 118788135 | 118788401 |
| DG10S1651 | 118794961 | 118795267 |
| DG10S1255 | 118834290 | 118834438 |
| DG10S644 | 118857362 | 118857745 |
| DG10S1652 | 118862172 | 118862311 |
| DG10S1654 | 118954536 | 118954869 |
| DG10S1688 | 118972583 | 118972717 |
| DG10S1689 | 118987319 | 118987480 |
| DG10S1690 | 119004704 | 119004986 |
| D10S1425 | 119004742 | 119004920 |
| DG10S651 | 119030166 | 119030595 |
| DG10S1655 | 119044005 | 119044188 |
| DG10S1691 | 119078576 | 119078943 |
| DG10S1207 | 119094382 | 119094722 |
| D10S1693 | 119109493 | 119109731 |
| DG10S1258 | 119131611 | 119131788 |
| DG10S656 | 119177278 | 119177672 |
| DG10S1694 | 119177430 | 119177614 |
| DG10S1695 | 119204432 | 119204655 |
| DG10S657 | 119204769 | 119205174 |
| DG10S658 | 119223917 | 119224102 |
| DG10S1696 | 119243071 | 119243408 |
| DG10S1657 | 119282299 | 119282586 |
| DG10S1658 | 119290241 | 119290632 |
| DG10S661 | 119305067 | 119305226 |
| DG10S662 | 119317406 | 119317660 |
| DG10S663 | 119330718 | 119331131 |
| DG10S1699 | 119364904 | 119365188 |
| DG10S665 | 119396863 | 119397144 |
| DG10S1659 | 119412611 | 119412992 |
| DG10S667 | 119448478 | 119448736 |
| DG10S1701 | 119473676 | 119473914 |
| D10S1236 | 119473739 | 119473870 |
| DG10S669 | 119485378 | 119485552 |
| DG10S670 | 119505799 | 119505905 |
| D10S190 | 119510348 | 119510554 |
| DG10S1702 | 119510362 | 119510479 |
| DG10S1153 | 119526060 | 119526329 |
| DG10S673 | 119606691 | 119606963 |
| DG10S1305 | 119615268 | 119615484 |
| DG10S675 | 119659153 | 119659532 |
| DG10S1661 | 119663175 | 119663453 |
| DG10S1662 | 119700563 | 119700948 |
| DG10S1306 | 119703996 | 119704204 |
| DG10S1663 | 119783538 | 119783739 |
| DG10S1704 | 119783569 | 119783694 |
| DG10S631 | 119788517 | 119788678 |
| D10S1148 | 119803465 | 119803663 |
| D10S1150 | 119803465 | 119803662 |
| D10S503 | 119803476 | 119803653 |
| DG10S632 | 119811193 | 119811621 |
| DG10S681 | 119811347 | 119811621 |
| DG10S633 | 119833701 | 119833987 |
| D10S2473 | 119833724 | 119833869 |
| DG10S682 | 119838539 | 119838806 |
| DG10S683 | 119853558 | 119853862 |
| DG10S684 | 119880412 | 119880572 |
| DG10S685 | 119909682 | 119910062 |
| DG10S686 | 119923527 | 119923790 |
| DG10S687 | 119954835 | 119955083 |
| DG10S1212 | 119972358 | 119972707 |
| DG10S1261 | 119995566 | 119995727 |
| DG10S1350 | 120004924 | 120005036 |
| DG10S1 | 120030830 | 120031131 |
| DG10S693 | 120100794 | 120101005 |
| DG10S1263 | 120132349 | 120132528 |
| D10S542 | 120417003 | 120417230 |
| DG10S1664 | 120444685 | 120444808 |
| DG10S1163 | 120506796 | 120507066 |
| DG10S703 | 120538236 | 120538484 |
| DG10S704 | 120570334 | 120570593 |
| DG10S706 | 120642052 | 120642312 |
| DG10S708 | 120699520 | 120699811 |
| DG10S709 | 120723780 | 120724158 |
| D10S1701 | 120849161 | 120849428 |
| DG10S716 | 120893782 | 120894153 |
| DG10S1669 | 120969521 | 120969659 |
| DG10S720 | 121016792 | 121017048 |
| D10S1792 | 121042408 | 121042574 |
| DG10S722 | 121070320 | 121070693 |
| DG10S1181 | 121101362 | 121101685 |
| DG10S724 | 121117025 | 121117286 |
| DG10S1670 | 121162511 | 121162898 |
| DG10S726 | 121217327 | 121217580 |
| DG10S1167 | 121247552 | 121247838 |
| DG10S729 | 121283257 | 121283429 |
| DG10S730 | 121318865 | 121319131 |
| DG10S731 | 121342622 | 121342893 |
| DG10S1278 | 121384227 | 121384464 |
| DG10S734 | 121425229 | 121425633 |
| DG10S735 | 121446549 | 121446695 |
| DG10S1185 | 121466936 | 121467248 |
| DG10S1129 | 121472295 | 121472600 |
| DG10S1085 | 121494260 | 121494657 |
| DG10S1327 | 121526700 | 121526830 |
| DG10S1271 | 121559895 | 121560066 |
| DG10S741 | 121638254 | 121638391 |
| DG10S1087 | 121647884 | 121648273 |
| DG10S1359 | 121713760 | 121713892 |
| DG10S1120 | 121726128 | 121726519 |
| DG10S1671 | 121750886 | 121750993 |
| DG10S1673 | 121823695 | 121823925 |
| DG10S749 | 121841816 | 121841997 |
| DG10S1134 | 121901381 | 121901668 |
| DG10S1674 | 121931406 | 121931809 |
| DG10S755 | 121976143 | 121976435 |
| D10S1757 | 121989325 | 121989539 |
| D10S209 | 121995173 | 121995376 |
| DG10S757 | 122029990 | 122030248 |
| DG10S1283 | 122045222 | 122045429 |
| DG10S1191 | 122071761 | 122072115 |
| DG10S761 | 122141102 | 122141322 |
| DG10S1678 | 122146312 | 122146535 |
| DG10S762 | 122167889 | 122168135 |
| DG10S763 | 122185793 | 122185925 |
| DG10S1284 | 122207287 | 122207508 |
| DG10S1137 | 122220809 | 122221073 |
| DG10S766 | 122257534 | 122257929 |
| DG10S767 | 122283871 | 122284250 |
| DG10S1361 | 122318975 | 122319081 |

TABLE 1-continued

Location of the 228 genotyped microsatellites on chromosome 10 in NCBI Build 34 of the human genome assembly.

| Alias | START: Build 34 Chr10 location | END: Build 34 Chr10 location |
|---|---|---|
| DG10S1680 | 122390160 | 122390294 |
| D10S1230 | 122407279 | 122407403 |
| DG10S772 | 122421708 | 122421845 |
| DG10S775 | 122463781 | 122463941 |
| DG10S777 | 122524358 | 122524547 |
| DG10S779 | 122580228 | 122580603 |
| DG10S784 | 122719087 | 122719236 |
| D10S1483 | 122948181 | 122948324 |
| D10S587 | 124728937 | 124729112 |

Single marker association analysis with the microsatellite markers identified association with DG10S478 (Table 2 and the FIGURE).

TABLE 2

DG10S478 Association to Type II Diabetes in Iceland

| Allele | Affected freq (n = 1185) | Control freq (n = 931) | RR [95% CI] | Two sided P |
|---|---|---|---|---|
| 0 | 0.636 | 0.724 | 0.67 | $2.1 \times 10^{-9}$ |
| 4 | 0.005 | 0.002 | 2.36 | 0.12 |
| 8 | 0.093 | 0.078 | 1.21 | 0.090 |
| 12 | 0.242 | 0.178 | 1.48 | $4.6 \times 10^{-7}$ |
| 16 | 0.022 | 0.015 | 1.53 | 0.076 |
| 20 | 0.001 | 0.003 | 0.39 | 0.17 |
| X | 0.364 | 0.276 | 1.50 [1.31, 1.71] | $2.1 \times 10^{-9}$ |

Six alleles are observed with this tetra-nucleotide repeat, with alleles 0, 8 and 12 accounting for 98% of chromosomes in the population controls. Allele 0 showed a protective association (Relative Risk (RR)=0.67; P=$2.1 \times 10^{-9}$) relative to the other alleles combined. This P-value is two-sided and takes into account that some of the patients are related to each other. DG10S478 is located in intron 3 of the transcription factor 7-like 2 (TCF7L2-formerly TCF4) gene on 10q 25.2. This marker is within a well defined LD block of 74.9 kb (based on the CEPH Caucasian HapMap Phase II) that encapsulates part of intron 3, the whole of exon 4 and part of intron 4 (the FIGURE).

When DG10S478 was genotyped in the CEPH Caucasian HapMap families, it became clear that allele G of SNP rs12255372, is observed to be nearly perfectly correlated with allele 0 of DG10S478 ($r^2$=0.95, P=$5.53 \times 10^{-38}$), and allele T of rs12255372 is correlated with other alleles of DG10S478. Moreover, the risk conferred by alleles 8 and 12 of DG10S478 do not differ (P=0.3). Hence it is natural to collapse all the non-0 alleles of DG10S478 into a composite allele which will be referred to as allele X. Allele X has frequency of 27.6% and 36.4% in controls and patients respectively. Assuming a multiplicative model (16, 17), compared to the risk for non-carriers, allele X has an estimated RR of 1.50 per copy carried.

Replication of the DG10S478 Association to Type II Diabetes

To verify the association of DG10S478 to type II diabetes, the microsatellite was genotyped in a Danish type II diabetes cohort of 228 cases and 539 controls. The Danish cohort was selected from the PERF (Prospective Epidemiological Risk Factors) study in Denmark (19). This female type II diabetes cohort had been diagnosed previously with type II diabetes. The association observed in Iceland was replicated (Table 3).

TABLE 3

DG10S478 Association to Type II Diabetes in Denmark

| Allele | Affected freq (n = 228) | Control freq (n = 539) | RR [95% CI] | Two sided P |
|---|---|---|---|---|
| 0 | 0.669 | 0.740 | 0.71 | 0.0048 |
| 4 | 0.002 | 0.004 | 0.59 | 0.62 |
| 8 | 0.070 | 0.048 | 1.49 | 0.091 |
| 12 | 0.239 | 0.190 | 1.34 | 0.032 |
| 16 | 0.020 | 0.018 | 1.12 | 0.78 |
| X | 0.331 | 0.260 | 1.41 [1.11, 1.79] | 0.0048 |

The composite at-risk allele X has a frequency of 26.0% in controls and 33.1% in type II diabetes cases, giving an estimated RR of 1.41 (P=0.0048).

Subsequently, the microsatellite was genotyped in a US Caucasian type II diabetes cohort of 361 cases and 530 controls from the PENN CATH study. This study is a cross sectional study of the association of biochemical and genetic factors with coronary atherosclerosis in a consecutive cohort of patients undergoing cardiac catheterization at the University of Pennsylvania Medical Center. Type II diabetes was defined as a history of fasting blood glucose ≧126 mg/dl, 2-hour post-prandial glucose ≧200 mg/dl, use of oral hypoglycemic agents, or insulin and oral hypoglycemic in a subject greater than age 40. The association observed in Iceland was also replicated in this population (Table 4).

TABLE 4

DG10S478 Association to Type II Diabetes in the United States

| Allele | Affected freq (n = 361) | Control freq (n = 530) | RR [95% CI] | Two sided P |
|---|---|---|---|---|
| −4 | 0.001 | 0.000 | — | — |
| 0 | 0.615 | 0.747 | 0.54 | $3.3 \times 10^{-9}$ |
| 4 | 0.003 | 0.004 | 0.73 | 0.72 |
| 8 | 0.085 | 0.049 | 1.79 | 0.0029 |
| 12 | 0.256 | 0.180 | 1.57 | $1.2 \times 10^{-4}$ |
| 16 | 0.040 | 0.020 | 2.07 | 0.012 |
| X | 0.385 | 0.253 | 1.85 [1.51, 2.27] | $3.3 \times 10^{-9}$ |

The composite at-risk allele X has a frequency of 25.3% in controls and 38.5% in type II diabetes cases, giving an estimated RR of 1.85 (P=$3.3 \times 10^{-9}$). Combining the results from all 3 cohorts using a Mantel-Haneszel model (NOTE 3) yields an overall two-sided P of $4.7 \times 10^{-18}$.

The association of the composite at-risk allele to type II diabetes in three populations constitutes strong evidence that variants of the TCF7L2 gene contribute to the risk of type II diabetes.

After establishing beyond doubt the association of the allele X to type II diabetes, we investigated the mode of inheritance more closely. The dominant model and recessive model can be rejected as the heterozygous carriers clearly have increased risk relative to the non-carriers (P<$1 \times 10^{-6}$) and reduced risk compared to the homozygous carriers (P<0.0001). The multiplicative model provides a better fit, but there is evidence that the risk of the homozygous carriers relative to the heterozygous carriers is greater than that of the risk of the heterozygous carriers relative to the non-carriers. Table 5 provides model-free estimates of the relative risks of the heterozygous carriers and homozygous carriers compared to the non-carriers.

TABLE 5

Model-free estimates of the relative risks

| Cohort | 00 | Genotype Relative Risk | | PAR |
| --- | --- | --- | --- | --- |
| | | 0X [95% CI] | XX [95% CI] | |
| Iceland | 1 | 1.41 [1.17, 1.70] | 2.27 [1.70, 3.04] | 0.21 |
| Denmark | 1 | 1.37 [0.98, 1.90] | 1.92 [1.13, 3.26] | 0.17 |
| USA | 1 | 1.64 [1.23, 2.19] | 3.29 [2.13, 5.07] | 0.28 |
| Combined | 1 | 1.45 [1.26, 1.67] | 2.41 [1.94, 3.00] | 0.21 |

The three cohorts have similar population frequency for the at-risk allele, but the RR estimates vary; with the strongest effect seen in the US cohort and the weakest in the Danish cohort. While there is no reason for the RR to be identical in the cohorts, it is noted that the differences in the estimated relative risks do not quite reach statistical significance (P>0.05). Combining the results from the cohorts assuming common relative risks, the heterozygous carriers and homozygous carriers are estimated to have relative risks of 1.45 and 2.41 respectively compared to the non-carriers (Table 5). Assuming a population frequency of 26% for the at-risk allele, heterozygous and homozygous carriers make up 38% and 7% of the population respectively. Hence, this variant has enough predictive value to be of clinical use. The corresponding population attributed risk is 21%, which is substantial from a public health point of view.

It should also be noted that allele X is in excess in impaired fasting glucose (IFG) individuals (fasting serum glucose between 6.1 and 6.9 mM). The composite at-risk allele X has a frequency of 27.7% in 1393 controls and 37.1% in 278 IFG cases, giving an estimated RR of 1.54 (P=1.36×10$^{-5}$).

Association of SNP Markers within Exon 4 LD Block of TCF7L2 with Type 2 Diabetes.

In Table 6 we list microsatellite and SNP markers residing within the exon 4 LD block of TCF7L2. The table contains publically available SNPs, as well as SNPs discovered by sequencing the entire LD block region. The table furthermore provides polymorphic microsatellite markers residing within the block.

Table 6. Polymorphic markers residing within the exon 4 LD block of TCF7L2 (between markers rs4074720 and rs7087006, positions in Build 34 co-ordinates:

rs4074720 (B34: 114413084)-rs7087006 (B34: 114488013)= 74929 bp. Sequence identification references are indicated as appropriate, referring in each instance to the SEQ ID number for the amplimer containing the polymorphism, and forward and reverse primers, as disclosed in the Sequence listing.

A. Public SNPs (Including all Hapmap Ethnicities)

| Public Alias | Chromosome 10 B34 location | Base Change | Sequence ID NO: |
| --- | --- | --- | --- |
| rs4074720 | 114413084 | A/G | |
| rs4074719 | 114413145 | C/T | |
| rs4074718 | 114413204 | C/T | |
| rs11196181 | 114413605 | A/G | |
| rs11196182 | 114414744 | C/T | |
| rs4603236 | 114414765 | G/T | |
| rs7922298 | 114414856 | C/T | |
| rs17747324 | 114417090 | C/T | |
| rs7901695 | 114418675 | C/T | 17-19 |
| rs11196185 | 114420079 | C/T | |
| rs4132115 | 114420083 | A/C | |
| rs4506565 | 114420628 | A/T | 14-16 |
| rs7068741 | 114420845 | C/T | |
| rs7069007 | 114420872 | C/G | |
| rs7903146 | 114422936 | C/T | 11-13 |
| rs11196187 | 114424032 | A/G | |
| rs7092484 | 114425520 | A/G | |
| rs10885402 | 114426284 | A/C | |
| rs12098651 | 114426306 | A/G | |
| rs6585198 | 114426824 | A/G | |
| rs7910244 | 114427209 | C/G | |
| rs12266632 | 114429546 | C/G | |
| rs6585199 | 114429758 | A/G | |
| rs7896811 | 114431304 | C/T | |
| rs6585200 | 114433196 | A/G | |
| rs6585201 | 114433370 | A/G | |
| rs4319449 | 114433993 | G/T | |
| rs12220336 | 114434854 | A/G | |
| rs7896091 | 114436550 | A/G | |
| rs12354626 | 114437016 | A/G | |
| rs7075199 | 114437307 | C/G | |
| rs7904519 | 114438514 | A/G | |
| rs13376896 | 114441336 | A/C | |
| rs10885405 | 114442257 | C/T | |
| rs10885406 | 114442311 | A/G | |
| rs11196192 | 114446874 | G/T | |
| rs6585202 | 114447390 | C/T | |
| rs7924080 | 114451599 | C/T | |
| rs7907610 | 114451677 | A/G | |
| rs12262948 | 114452313 | C/G | |
| rs12243326 | 114453402 | C/T | 8-10 |
| rs12265110 | 114453606 | C/T | |
| rs7077039 | 114453664 | C/T | |
| rs11196198 | 114456472 | A/G | |
| rs12775336 | 114459590 | G/T | |
| rs7904948 | 114459672 | A/T | |
| rs7100927 | 114460635 | A/G | |
| rs11196199 | 114460704 | A/G | |
| rs17685538 | 114462058 | C/G | |
| rs11592706 | 114463573 | C/T | |
| rs7081912 | 114463678 | A/G | |
| rs7895340 | 114466112 | A/G | 23-25 |
| rs11196200 | 114466525 | C/G | |
| rs11196201 | 114467894 | A/T | |
| rs11196202 | 114470254 | A/G | |
| rs11196203 | 114470447 | A/C | |
| rs11196204 | 114470518 | A/G | |
| rs11196205 | 114471634 | C/G | 20-22 |
| rs10885409 | 114472659 | C/T | |
| rs12255372 | 114473489 | G/T | 5-7 |
| rs12265291 | 114474827 | C/T | |
| rs7904443 | 114475774 | A/G | |
| rs11196208 | 114475903 | C/T | |
| rs7077247 | 114476658 | C/T | |
| rs11196209 | 114477314 | A/G | |
| rs4077527 | 114477628 | A/G | |
| rs12718338 | 114477634 | C/T | |
| rs11196210 | 114478558 | C/T | |
| rs7907632 | 114481823 | A/G | |
| rs7071302 | 114482114 | G/T | |
| rs12245680 | 114484778 | C/T | |
| rs11196213 | 114486141 | C/T | |
| rs4918789 | 114486394 | G/T | |
| rs7085785 | 114487050 | C/T | |
| rs7085989 | 114487326 | A/G | |
| rs7087006 | 114488013 | A/G | |

B. Novel SNPs Discovered and Subsequently Validated in the Exon 4 LD Block of TCF7L2 (Amplimers Below):

| deCODE Alias | Chromosome 10 B34 location | Base Change | Sequence ID NO: |
|---|---|---|---|
| SG10S405 | 114418658 | C/T | 26-28 |
| SG10S428 | 114421901 | A/C | 29-31 |
| SG10S422 | 114457824 | A/G | 32-34 |
| SG10S427 | 114463480 | A/T | 35-37 |
| SG10S408 | 114466074 | A/T | 38-40 |
| SG10S409 | 114471574 | A/C | 41-43 |
| SG10S406 | 114471618 | C/G | 42-44 |
| SG10S407 | 114473534 | C/G | 45-47 |

C. Polymorphic Microsatellites Within the Exon 4 LD Block of TCF7L2 (Amplimers Below):

| Microsatellite | C10 B34 Start | C10 B34 End | Sequence ID NO: |
|---|---|---|---|
| DG10S2164 | 114460344 | 114460627 | 48-50 |
| DG10S478 | 114460845 | 114461228 | 2-4 |
| DG10S479 | 114475487 | 114475632 | 51-53 |

TABLE 7

Amplimers and primers for selected markers within the exon 4 LD block of TCF7L2

>DG10S478
TTCAGGCCATTGGTGTTGTATATATTTCAAGATTTGCTCACAGGTCCAAA
GCTTAACTTAAGCTCCCTGAGACATATCATAAAATATGATTTGGGGAAAA
ACCCTAATGGGCCATGATCAGAACATTATTATTCAACAAAGGATGAAATG
CTTAAGCCAAGATGGCCTTCTTTCTTTCTTTCTTTCTTTTTTTTA
ATGAAAGTTGAGCAGACTCCCGTCCAACAGTTTTCAATGTAGGAATTCCC
ACAGCCCCATTTGATTGCAGTTTGTTGAAAAGTTTAATGTTTTGTAGGC
AATTCATAATTTCCACATTGAACAGCCTGAGAGGAAGAGAGCTGGAGCCC
ACTGTTGTTTTGTAGTGGGATGGTGGGAACTTT
(SEQ ID NO:2)

Primers:
F: TTCAGGCCATTGGTGTTGTA
(SEQ ID NO:3)

R: AAAGTTCCCACCATCCCACT
(SEQ ID NO:4)

>rs12255372
TTGTCCCTTGAGGTGTACTGGAAACTAAGGCGTGAGGGACTCATAGGGGT
CTGGCTTGGAAAGTGTATTGCTATGTCCAGTTTACACATAAGGATGTGCA
AATCCAGCAGGTTAGCTGAGCTGCCCAGGAATATCCAGGCAAGAATKACC
ATATTCTGATAATTACTCAGGCCTCTGCCTCATCTCCGCTGCCCCCCGC
CCCCTGACTCTCTTCTGAGTGCCAGATTCAGCCTCCATTTGAATGCCAAA
TAGACAGGAAATTAGCATGCCCAGAATCCACGTCTTTAGTGCACTCTCTC
CCCAGCTCCAAACCTGTTACTGCTTGTGTTCAACATCTCAGTAAAGCTCA
ACAACATCGACCCATT
(SEQ ID NO:5)

Primers:
F: TTGTCCCTTGAGGTGTACTGG
(SEQ ID NO:6)

R: AATGGGTCGATGTTGTTGAG
(SEQ ID NO:7)

>rs12243326
GCTGTGAAATCCCCTGTGTAGTGGGAAGAAGAAATAGCAAATCTTAGCTG
CCTTGGACCTGATATAATTATTTGTCTTCATTTACATGGTTYATCCTTCA
AGGTTGAATAAATGATGTGGGAGCTAGTCAAGGGGCTTTAGGTATGTGAT
TTCATGCCTACTTTTTTTTAGGTAGAGAAACTGAGGTCACAGGGTACTAG
AGAATGGACTCTAAGATTCAGGTTTCTGAATTGCCTGTGGTTTTGTTGAC
TCAACTGCTCTTCTGTTGTTTTTTAGCCACATGCCTTGAAACAGTCCTCT
TTCCCATGTTTCTTCATCAGCACCATTAACCCAAGGTATACTGTCCTCTC
TTATCTTTCACAAGGTCTTGGAGTTCCCATGCCTTTGTAAGCATCCCTCC
CCGAGATTCAGCACCAACCAAAATCACATTTGGAAAAATTGCTTGTTTCC
CAAGAAGCTTTGGAGGATATGATTTTGTATAGAACGGGTTCACAGGTTTT
CTGTTCATTCTTCTATGGTGGAGTGTGTGTGTATGTGACTCTGTCTTCTC
TCCATTCC
(SEQ ID NO:8)

Primers:
F: GCTGTGAAATCCCCTGTGTAG
(SEQ ID NO:9)

R: GGAATGGAGAGAAGACAGAGTCA
(SEQ ID NO:10)

>rs7903146
AAGGGAGAAAGCAGGATTGAGCAGGGGGAGCCGTCAGATGGTAATGCAGA
TGTGATGAGATCTCTGCCGGACCAAAGAGAAGATTCCTTTTTAAATGGTG
ACAAATTCATGGGCTTTCTCTGCCTCAAAACCTAGCACAGCTGTTATTTA
CTGAACAATTAGAGAGCTAAGCACTTTTTAGATATYTATATAATTTAATTG
CCGTATGAGGCACCCTTAGTTTTCAGACGAGAAACCACAGTTACAGGGAA
GGCAAGTAACTTAGTCAATGTCAGATAACTAGGAAAAGGTTAGAGGGGCC
CTGGACACAGGCCTGTGTGACTGAGAAGCTTGGGCACTTCACTGCTACAT
TTCATCTCTTCGCT
(SEQ ID NO:11)

Primers:
F: AAGGGAGAAAGCAGGATTGA
(SEQ ID NO:12)

R: AGCGAAGAGATGAAATGTAGCA
(SEQ ID NO:13)

>rs4506565
CTGATGAGGGTAGGGAGCATCTGTCTGCAGCTTCATCTTCATTGTCTAGG
GGCTCCAGAAATATCTGTGAGTAAATAAGTTATTTAATCTTTGCCTCAAA
TTTCCAGTGACTGTAGGGATATAGCTGTGAGCCTCTAGGAGCTGAGATTT
TTTAAATTTCCCACTTAAACATTTATTTAAAAATTTTGTGCTCAGCATGG
ACTAAGGACTTTACATTCATTAACTCATTTACAGCTTGATCCTATGCGGT
GGGCATTCATTTACAGAGGATCCCATTTTACAGGTGAGGAAGAGGCCAGC
TAGGGGTGCAGCCTAGGTTAGTATTCTAGAGCTCATCAGGCTGTGTTGTC
CCCAGTGAAAGAATAAGCAAAGAAGTGAATGTTGTGCATTGAGAAAAATG
ACTCTCGGAGGAGGATGAGCCTCTCGGATATGGCGACCGAAGTGATWTGG
GGCCCTTGTCAAGGGTCTCTATTATGGCATCAAGAAAAGATGCTGCTTTC
GGTGATGCCCGAGGAGAGCCTCAATATTTTACATGGGAAACCTAAAAAAG
GGGCCATGTTGTGGTCTCTGCACCTAAGA
(SEQ ID NO:14)

Primers:
F: CTGATGAGGGTAGGGAGCA
(SEQ ID NO:15)

R: TCTTAGGTGCAGAGACCACAAC
(SEQ ID NO:16)

>rs7901695
TATTTAGAAACCATAAAATCCACCTATTTGAGGTGTACAATTGAGTGATT
TTCTGTATAGTCACAGATCTGTGCAGTCATCCACACCCTCTAACTCCAGG
ACATTTTCCTCACCCCCGAGGAGAAACCTCCCTTACCCATTAGCAGTCAC
TCCTCATTTCCTCTCCCCCCAGCCCCTGGCAATCACTGTGGATTTGCCTG
TTCTTGACATTTCATATAAATGGTATCATAAAATCTAYGGGCTTTTGTGT
CTGTCTGCTTTCACTTAGCATACGGTTCTCAAGGTTCATCCAGTATTGTA
GCATCTATCAGTATGTCATTCCTTTTTATGGCCAAATAATATTTTTATTGT
ATGGATAGACATTTTGTTTATTCATTTATCTGTTTTGGTTATTATGAGT
AACACTACTATGAACATTTTGCACAAATTTTTGTATTGACATGTTTTCAT
TTCTCCTGGGTATAGTCCTATGAGTGGAATTGCTGG
(SEQ ID NO:17)

Primers:
F: TATTTAGAAAGCATAAAATCCACCTAT
(SEQ ID NO:18)

R: CCAGCAATTCCACTCATAGGAC
(SEQ ID NO:19)

TABLE 7-continued

Amplimers and primers for selected markers within the exon 4 LD block of TCF7L2

>rs11196205
TTGTCTCCTTTTGTTTCTGCTACTGTGAATGATCCTGTGATGATCATCTT
TGTGTGTAAATCTTTGTCCCCTCGCCCCCTCCCCTTTTATTATTTTCTTG
GGATAGACCCCAGGACAAAAGGTAGAAAAGAACAAAGTGTTAAAAAATTT
CTTGATACATAGCCACAGATTATTTTCCTGAAAGTTCTCAACATTTATAA
CTACSAGCAGTATGTAAGAGAGTTATGGTTGGAATGATTTTAATGTCTCT
GGGGAATTTAACAACAAAAAAACTTTAGGCTTCTTTGGAGAGAGACATGC
CCTTAACTCCACCCCGCCCTAGAACAGAGACCCAGCCCATCCAAGTCAGC
CTCCCCAGGTCCTCCACCTTCAAAACAGGCAAACGAAATCATTTCTTGAA
TAATTGGTAGGCTTCAAGGTCAGATGTT
(SEQ ID NO:20)

Primers:
F: TTGTCTCCTTTTGTTTCTGCTAC
(SEQ ID NO:21)

R: AACATCTGACCTTGAAGCCTAC
(SEQ ID NO:22)

>rs7895340
TCAGGGACAGTGCATAGGTGTAAAGAAGTTGCTGGTTGGGGGTTCTAATG
CAGGTTTCTCCAAAAGTGAATGCCCTGTTAAAAAAAAATTCTTAACAAAT
ATACAGAGATTTTTTTTTTAAAAAAGTGTGACAGTTCTAGACACCTAGAG
AGTAAAARTGAAGAAGCCTGTTTTCAGGTTTCCCGCCTCCCTGAATTTCCC
AGCATGGTCCAGGCTTTGAAATTTATTTATCTGCTTTTGGCAATGGTTGA
TGGGAATTTCCCACATTTATTTTTTAGCTACAGAGAAAGGACATTATCTT
TAAAATCTCTTCGTTGTTCTCTCTTTGA
(SEQ ID NO:23)

Primers:
F: TCAGGGACAGTGCATAGGTG
(SEQ ID NO:24)

R: TCAAAGAGAGAGAACAACGAAGA
(SEQ ID NO:25)

>SG10S405
TATTTAGAAACCATAAAATCCACCTATTTGAGGTGTACAATTGAGTGATT
TTCTGTATAGTCACAGATCTGTGCAGTCATCCACACCCTCTAACTCCAGG
ACATTTTCCTCACCCCCGAGGAGAAACCTCCCTTACCCATTAGCAGTCAC
TCCTCATTTCCTCTCCCCCAGCCCCTGGCAATCACTGTGGATTTGCCTG
TTCTTGACATTTCATATAAAYGGTATCATAAAATCTATGGGCTTTTGTGT
CTGTCTGCTTTCACTTAGCATACGGTTCTCAAGGTTCATCCAGTATTGTA
GCATCTATCAGTATGTCATTCCTTTTTATGGCCAAATAATATTTTATTGT
ATGGATAGACATTTTGTTTATTCATTTATCTGTTTTTGGTTATTATGAGT
AACACTACTATGAACATTTTGCACAAATTTTTGTATTGACATGTTTTCAT
TTCTCCTGGGTATAGTCCTATGAGTGGAATTGCTGGGTCATATAATAAAT
AACTGTTTAACATTTTGGGGAGCTGCCAAACTTTTAAAACCTTGGGTTCT
GTGATGTACCAGTTGTGTTAGGCA
(SEQ ID NO:26)

Primers:
F: TATTTAGAAACCATAAAATGCACCTAT
(SEQ ID NO:27)

R: TGCCTAACACAACTGGTACATC
(SEQ ID NO:28)

>SG10S428
TGCCAGGGGTTTTATGGTTAATTTTCCTCCATTATGAGGGTTGACTCAGC
CTTGGGTATTAGATGTCTTTGAGAATCCAGGGTTCAAATACCACAGCTGG
TAGAATGTTTCTCAACTTGGAGCCAATCTCCATCTACTGAAGGTACGCTG
GTTTAGACAGACAACAGGGACATCAGCATTTTAAAAAGCGGTGGAAAAAG
TTTGCTTGTCTTGATTGGAGCCATGACATTTTATTTTGAAATTTCAAATA
ACATGAAGGGAGGTTTGGAGCGGTTTTTGGTTTATCCAAAGGGCAGTGGA
TTGAAGGCTGAGAAACACCAGGCTGAATGGGAGAGGGGTTGGGGTCCCCC
TGTGAGATAGTGAAACAATGGTAGTGCCATCCAATGATAGGCACTTTTCT
GTCATTCAGAAGCAGAAAGGGGGCCAGAGGCCCATTGGCCTTACTGGGMA
GTAAGCTGTAGAGCTGCTGCCTTTTCGTGAAAGGGTTGACACCAACCTTC
TCCCCCAGGAAGAGTGACCAGGGACCTGAGGGGCATGGTCGAGCAGATGA
CAGCCTTTGTAAAACATCTCC
(SEQ ID NO:29)

Primers:
F: TGCCAGGGGTTTTATGGTTA
(SEQ ID NO:30)

R: GGAGATGTTTTACAAAGGCTGTC
(SEQ ID NO:31)

>SG10S422
TTGGTAGAGATGGGGTCTCCTAGGCTGGTCTTGAACTCCTGGRCTCAAGC
AATCTTCCTGCCTCAGCCTTCCAAAGTACTGGGATTACTGGCGTGGGCCA
CCATGCCTGGCTTGAAATTTTTCTATGGCTTTATTCTTTCTCCAAGTACA
GAGTCTACCCAACCTTCTGAGATCTTTGGTTTTCTTTTCCTAGGTAACTA
TAGTACATACTTATTTATGTTAAACAACAGCAATCACACATTTCTTTTTC
TATACAGTCATGCTTTATAGGCAAATAAAGCCTCCGTCTTAGGCTTTCTG
GATTTTTTCAAAAGATGCAATTCCTGGAGTATGTTTTTACTTAGAGCAAA
GCAGCCTAGTCTCCTATACCTTCTGCATCTGCAGAAAAGTTGGTTAAACA
GACTTTGTAATGATGCCCCTTACAATTCTGAAGGGACTTGTGAAATAGTT
TCACAGAGTTTCAGTGTTAGGTATATTTGATCAATGCTAACTTTTGGAAA
ACTTTGGTGCCTGTATGATTCAGAGGGTAGGGCAGAATATTAAATTAATC
ACAACTTCTTGTATTTTAACCATTCTGGGTAAATTGGGATTCCGTGACGC
CCAGGCAAAATTAT
(SEQ ID NO:32)

Primers:
F: TTGGTAGAGATGGGGTCTCC
(SEQ ID NO:33)

R: ATAATTTTGCCTGGGCGTCA
(SEQ ID NO:34)

>SG10S427
TATCTTATATCCCCTCCAAGCATTCATTAACTGATGGATTAGTGAGTTGG
CCTTGGAGAAGCATAAAGGCTCGTCTCCATGTGCTTCTAAGCATTGTGTCT
AAGTTCTGTTTGGTTTCCTGAGTGAAACTGTCTTAATGTTACCAACAGAA
GTTAAATGCCTAAGAGWTTCTTATACATGGGTCGAGTACCTCTGTGACTG
GGCAAGCCACCTCACCTCATTTTACCTTGTCTGCAAAATGAGGAACTGGG
TCAACTCATCGTTCAAATCTCACTGAAAGCTAATTGATCGCTTTTGACAG
AAGTAGCTCCCTTGGGCCGTATATTTATTTCCTAGCTTGGAGGAAGGTGG
GGACAGACAGAATTGATGTACACCTTTATTTTTATCTCTATGGTAAACCT
GTGCATACTAAAGCATTCCTCTGGTCTTTTGAGATGAGTGTATACATTGT
GTCTGGCCCTGTGCATTTTTTACCAAGAAGTAAGTTTTGTTGAGTAAACT
TGGGTTGTATGAAGAACTGCATGCTCACCGTACTCAAGTAGCTTTTGCTA
CCTAAAGGACAGCTGCTCATATGTACTTGACTTCCTTTAAAGTGAAGGAT
GATGACATTTGAAAAACGGAGGTTGAAAAGGAG
(SEQ ID NO:35)

Primers:
F: TATCTTATATCCCCTCCAAGCATTC
(SEQ ID NO:36)

R: CTCCTTTTCAACCTCCGTTTT
(SEQ ID NO:37)

>SG10S408
TTGAGCATGTGTTATTTAATGAGTTATACCTCTGTCATATGTGTGTTT
ATATCACAAATAACTTATTTTTATAAAACCATATTTTGAGTCATCATTT
GTGACAATGTCTTCTTTTCTCTGGTATAAATGAGGCATGTAGAAAGAAGA
TTGACATTTGCTAGAAGCTTCCCCTTTCCTCTAACTCCACAATAAAATGG
ATGCTCATAATTACATCTGCTCCTATAAGGTCAAGATTTCAGGGCTGGAA
GTGACCTTAGATCATTTAGGCCCAACTTGCCCTCAGGAAAGGAAACTGAG
GCCCAGAGATGCCTTAAGTGAATTGCCCAATGTCACACGCTGAGTCAGTG
GCCAGAGCAAGGCTTGGATCCAGTTCTCTGCTCCCTTTCCAGAGCCTTGT
GATGTCTTCTCTCCTACAGGAGGTGAAAATAACTGCTGTGGCTGGTTCTG
TTTTGCTGACTGTAAATTGGGTCATGGTCAGGGACAGTGCATAGGTGTAA
AGAAGTTGCTGGTTGGGGGTTCTAATGCAGGTTTCTCCAAAAGTGAATGC
CCTGTTAAAAAAAATTCTTAACAAATATACAGAGATTTTTTTTTWAAAA
AAGTGTGACAGTTCTAGACACCTAGAGAGTAAAGTGAAGAAGCCTGTTTT
CAGGTTTCCCGCCTCCCTGAATTTCCCAGCATGGTCCAGGCTTTGAAATT
TATTTATCTGCTTTTGGCAATGGTTGATGGGAATTTCCCACATTTATTTT
TTAGCTACAGAGAAAGGACATTATCTTTAAAATCTCTTCGTTGTTCTCTC
TCTTTGAGTGAGGAGAGAAGATGTAAAGGAAATGCTGGCAGTGGTTCAGAGTGGA
CACAGCCCCTGTGTTTGTGGCATAGGCTCTGTGGGCCCCATGCCAGGGAG
CAGTACCCCCGTGTAAAGGAGTGGGGGGTTTGTCCATTTGGATAGAGCAAA
GATCCTCCACCTCAAATCCCACAAGAACAGTTGCCACAACCTGGGCCCTA
AGCATCTCATTTTCCTATGTAGAAATTAATGATCTGGAGGAGATGGCAAA
ACATTCCTTCCAGAGCCTGTGTGGATTTTGG
(SEQ ID NO:38)

TABLE 7-continued

Amplimers and primers for selected markers within
the exon 4 LD block of TCF7L2

Primers:
F: TTGAGGATGTGTTATTTAATGAGTTA
(SEQ ID NO:39)

R: CCAAAATCCACAGAGGCTCT
(SEQ ID NO:40)

>SG10S409
TAGTGCTCAGTATTTCCAACGTTCTGTTTATTTAAGATGAAAATTGCTGT
AGTTAATAAGCACTTCCCCATGTCATTAAAATGCTTAAGGATTTTTAATG
ACCACATAACAGTCCATAATATGATTAAACCCCAATTTACTGAATCAATG
CCATATTGTTGGGTCTTTAGATTGTCTCCTTTTGTTTCTGCTACTGTGAA
TGATCCTGTGATGATCATCTTTGTGTGTAAATCTTTGTCCCCTCGCCCCC
TCCCCTTTTATTATTTTCTTGGGATAGACCCCAGGACAAAAGGTAGAAAA
GAACAAAGTGTTAAAMAATTTCTTGATACATAGCCACAGATTATTTTCCT
GAAAGTTCTCAACATTTATAACTACGAGCAGTATGTAAGAGAGTTATGGT
TGGAATGATTTTAATGTCTCTGGGGAATTTAACAACAAAAAAACTTTAGG
CTTCTTTGGAGAGAGACATGCCCTTAACTCCACCCCGCCCTAGAACAGAG
ACCCAGCCCATCCAAGTCAGCCTCCCCAGGTCCTCCACCTTCAAAACAGG
CAAACGAAATCATTTCTTGAATAATTGGTAGGCTTCAAGGTCAGATGTT
(SEQ ID NO:41)

Primers:
F: TAGTGCTCAGTATTTCCAACGTTCT
(SEQ ID NO:42)

R: AACATCTGACCTTGAAGCCTACC
(SEQ ID NO:43)

>SG10S406
TAGTGCTCAGTATTTCCAACGTTCTGTTTATTTAAGATGAAAATTGCTGT
AGTTAATAAGCACTTCCCCATGTCATTAAAATGCTTAAGGATTTTTAATG
ACCACATAACAGTCCATAATATGATTAAACCCCAATTTACTGAATCAATG
CCATATTGTTGGGTCTTTAGATTGTCTCCTTTTGTTTCTGCTACTGTGAA
TGATCCTGTGATGATCATCTTTGTGTGTAAATCTTTGTCCCCTCGCCCCC
TCCCCTTTTATTATTTTCTTGGGATAGACCCCAGGACAAAAGGTAGAAAA
GAACAAAGTGTTAAAAAATTTCTTGATACATAGCCACAGATTATTTTCCT
GAAAGTTCTSAACATTTATAACTACGAGCAGTATGTAAGAGAGTTATGGT
TGGAATGATTTTAATGTCTCTGGGGAATTTAACAACAAAAAAACTTTAGG
CTTCTTTGGAGAGAGACATGCCCTTAACTCCACCCCGCCCTAGAACAGAG
ACCCAGCCCATCCAAGTCAGCCTCCCCAGGTCCTCCACCTTCAAAACAGG
CAAACGAAATCATTTCTTGAATAATTGGTAGGCTTCAAGGTCAGATGTT
(SEQ ID NO:44)

Primers:
F: TAGTGCTCAGTATTTCCAACGTTCT
(SEQ ID NO:42)

R: AACATCTGACCTTGAAGCCTACC
(SEQ ID NO:43)

>SG10S407
TGCTATGTCCAGTTTACACATAAGGATGTGCAAATCCAGCAGGTTAGCTG
AGCTGCCCAGGAATATCCAGGCAAGAATGACCATATTCTGATAATTACTC
AGGCCTCTGCCTCATCTCCGCTGSCCCCCCGCCCCCTGACTCTCTTCTGA
GTGCCAGATTCAGCCTCCATTTGAATGCCAAATAGACAGGAAATTAGCAT
GCCCAGAATCCACGTCTTTAGTGCACTCTCTCCCCAGCTCCAAACCTGTT
ACTGCTTGTGTTCAACATCTCAGTAAAGCTCAACAACATCGACCCATTAC
TTAGGCCTCAAACCTTGGGTGGCATCGTCGATTGCTCTTTTCTTTCATAC
CCCACATTCAACCCATCAGCCCATCCCACAGGCCCAAGTGTGTCCTCTCT
ACCTTCAAAGCGTGTGTGGCATCCACCGCTTATCACCACCTCTGCCATTA
CCACTGGAGTCCAGTGCCATCATCTCTCACTTGGATGTGGCCAGAGTGTC
TTTGCTGGTCTCCTTCTTGCTTCCTACCTTTGTAACAGCCTATCATCTAT
CTCTGGTCTCCATAGCTCACTCCCATACTTTGAGAGGGCCTTTGAAAGCC
TTAGACAGATCATATCACAGACCTCTATACTGAAAGTCGGG
(SEQ ID NO:45)

Primers:
F: TGCTATGTCCAGTTTACACATAAGG
(SEQ ID NO:46)

R: CCCGACTTTCAGTATAGAGGTCTG
(SEQ ID NO:47)

>DG10S2164
CCATCTGTGGAGCAGAGTCACTGAAAGGAAATACTGGAAATACTGGAAGC
CACTTGGTGTTTTATCAAGGATGTGAGGTTTCCTGGCAACTTTGTCGCCA
TATCATCATCATCATCACCATCATCATCATCATCATCATCATCATCATCA
TCATCATCATCATCATCTGCCCTTTAAGTTTTCTGCTTGTTTAGAAAAGA
AATTTATACAGAGCCCCCAGTAGCAGCTGTAAGGGGGCAGGTTCTTGGAG
CAGCCCATCCTCAACATTCTTGCTGCTGATGGAA
(SEQ ID NO:48)

Primers:
F: CCATCTGTGGAGCAGAGTCA
(SEQ ID NO:49)

R: TTCCATCAGCAGCAAGAATG
(SEQ ID NO:50)

>DG10S479
TCCACGCAGAGAGGATCTAAATCTGGCTCTTTGCAATTGCCTTCATACAT
GTGCATACACACCACACACACACACACACACACACACACACACACACACA
CAGACACATACATATGCACACACCCCGACTCAATGGAGGACCCTC
(SEQ ID NO:51)

Primers:
F: TCCACGCAGAGAGGATCTAAA
(SEQ ID NO:52)

R: GAGGGTCCTCCATTGAGTCG
(SEQ ID NO:53)

To further investigate the possibility that other marker alleles in the exon 4 LD block of TCF7L2 exhibit a higher correlation with type II diabetes than allele X, we used the DG10S478 genotype data generated in the HapMap CEU samples. The five SNPs from HapMap Phase I with strongest correlation to DG10S478 were, in descending order, rs12255372 ($r^2$=0.95), rs7903146 ($r^2$=0.78), rs7901695 ($r^2$=0.61), rs11196205 ($r^2$=0.43), and rs7895340 ($r^2$=0.42). We genotyped these five SNPs in the three cohorts and the correlations between the five SNPs and DG10S478, the latter treated as a biallelic marker, were very similar to that observed in the CEU samples. All five SNPs showed association to type II diabetes. While some SNPs showed slightly higher estimated relative risks and lower p-values in one or two of the cohorts, none exhibited stronger association to type II diabetes than DG10S478 when the results for all three cohorts were combined using the Mantel-Haenszel model. However, although rs11196205 and rs7895340 clearly have weaker association to type II diabetes, compared to allele X (RR=1.56, P=4.7×10$^{-18}$), the strength of the association to type II diabetes for allele T of rs12255372 (RR=1.52, P=2.5× 10$^{-16}$) and for allele T of rs7903146 (RR=1.54, P=2.1×$^{-17}$) are comparable.

Following the subsequent release of HapMap Phase II in October 2005, two additional SNPs were identified that show strong correlation to microsatellite DG10S478–rs12243326 ($r^2$=0.961) and rs4506565 ($r^2$=0.716). The alleles associated with susceptibility to type 2 diabetes will be C for rs12243326 (C/T SNP) and T for rs4506565 (A/T SNP).

It should be noted that among those haplotypes that carry the C allele of rs7903146, those that carry the A allele of rs10885406 have an estimated relative risk of 1.06 compared to those that carry the G allele of rs10885406, but the difference is not statistically significant (P=0.22).

In an attempt to replicate and refine this association with type 2 diabetes, we genotyped DG10S478, rs12255372 and rs7903146 in a large additional Danish cohort, consisting of 1111 cases and 2315 controls and in a more genetically diverse West African cohort, consisting of 618 cases and 434 controls derived from the Africa America Diabetes Mellitus study(23). In the Danes, all three variants were strongly associated with disease risk, as previously observed in Iceland. However, the association of allele T of rs7903146 (Relative Risk=1.53, P=4.06×10$^{-4}$, PAR=24.4%) was noticeably stronger than that provided by the other two variants. In the West African study group, after adjustment for relatedness and ethnic origin, we replicated the association of allele T of rs7903146 to type 2 diabetes (Relative Risk=1.45, 95% C.I.=1.20-1.76, P=0.000146, PAR=22.2%), but not in the case of the other two variants. This suggests that allele T of rs7903146 is either the risk variant itself or the closest known correlate of an unidentified risk variant. The exclusion of the markers DG10S478 and rs12255372 as at-risk markers in the West African group was possible because unlike in populations of European ancestry, where the T allele of rs7903146 occurs almost exclusively on chromosomes carrying both allele X of DG10S478 and allele T of rs12255372, in West Africans the T allele of rs7903146 occurs with both alleles of DG10S478 and rs12255372. This is consistent with the observation that T is the ancestral allele of rs7903146, whereas allele X of DG10S478 and allele T of rs12255372 are both different from the chimpanzee reference sequence. More generally, this finding is also consistent with the expectation that relatively diverse populations, such as those of West Africa, provide the means to refine association signals detected in regions of strong linkage disequilibrium in more homogeneous populations.

Discussion

In this study we describe the identification of a novel candidate gene for type II diabetes within the previously reported 10q linkage region(10), encoding transcription factor 7-like 2 (TCF7L2—formerly TCF4) on 10q25.2. We show that it confers risk of type II diabetes in Iceland, Denmark and the US with similar frequency and relative risks. While the variant does not explain a substantial fraction of the familial clustering of type II diabetes, the population attributed risk of at least 20% is significant from a public health point of view. Compared to the non-carriers, the relative risks of heterozygous carrier of the at-risk composite allele (approximately 38% of the population) and homozygous carriers (about 7% of the population) are 1.45 and 2.41, respectively. Hence, this variant has enough predictive value to be of clinical use.

We report the variant as a type II diabetes-associated microsatellite, DG10S478, within the third intron of the TCF7L2 gene. The TCF7L2 gene product is a high mobility group (HMG) box-containing transcription factor which plays a role in the Wnt signalling pathway. This pathway is considered one of the key developmental and growth regulatory mechanisms of the cell; it is mediated by secreted glycoproteins, known as Wnts, which initiate many signalling cascades within target cells upon binding to a cognate receptor complex, consisting of a member of the Frizzled family and a member of the LDL receptor family, Lrp5/6(24). Wnt signaling uncouples the central player in this pathway, β-catenin, from the degradation complex and translocates it to the nucleus where it transiently converts TCF factors from repressors into transcriptional activators(25). The β-catenin protein is also important for mediating cell adhesion through its binding of cadherins(15).

The NCBI RefSeq for TCF7L2 contains 14 exons. However, Duval et al(26) showed that TCF7L2 has 17 exons, of which 5 are alternative; in addition, it was reported that three alternative splice acceptor sites are used. This study also demonstrated the alternative use of three consecutive exons located in the 3' end of the TCF7L2 gene which change the reading frames used in the last exon, leading to the synthesis of a large number of TCF7L2 isoforms with short, medium, or long COOH-terminal ends.

Similar to TCF7L2, five of the six positionally cloned genes for the rare Mendelian forms of Type II Diabetes, namely maturity-onset diabetes of the young (MODY), are transcription factors(27). Additional transcription factors have been implicated in the pathogenesis of type II diabetes, including peroxisome proliferator-activated receptor gamma (PPARγ)(7) and the forkhead gene family(28, 29). Noble et al described a missense mutation (C883A) in the related TCF7 gene in type 1 diabetes(30). However, it is not clear if TCF7 and TCF7L2 operate in the same pathway with respect to the pathogenesis of diabetes.

Mutations have been described in the TCF7L2 gene, including the deletion of an A in an (A)9 coding repeat (exon 17)(26, 31-33) and a number of mutations in colorectal cell lines(26). DG10S478 resides within a clearly defined 74.9 kb LD block (CEPH Caucasian HapMap Phase II) that encapsulates exon 4 and flanking intronic sequences 5' and 3' to the exon. It is possible that DG10S478 is the causative variant itself; it is also possible that DG10S478 is a surrogate for an underlying variant that affects transcription, splicing or message stability. Such a variant is likely to be in strong LD with DG10S478, i.e. the variant resides within the exon 4 LD block of TCF7L2

Several lines of evidence suggest an enteroendocrine role of this gene in the pathogenesis of type II diabetes. Firstly, TCF7L2 has been implicated in the development of colorectal cancer(34) and small-molecule antagonists of the oncogenic TCF/β-catenin protein complex have been already described (35). In addition, TCF7L2−/−mice, which die within 24 hours after birth, lack an intestinal epithelial stem-cell compartment (36). Variants of the TCF7L2 gene could influence the susceptibility to type II diabetes through altering levels of the insulinotropic hormone glucagon-like peptide 1 (GLP-1), one of the peptides encoded by the proglucagon gene whose expression in enteroendocrine cells is transcriptionally regulated by TCF7L2. In concert with insulin, GLP-1 exerts crucial effects on blood glucose homeostasis(12). GLP-1 analogs and inhibitors of dipeptidyl peptidase IV are currently in clinical development.

The references cited in this specification are incorporated herein in their entirety.

REFERENCES

1. A. F. Amos, D. J. McCarty, P. Zimmet, *Diabet Med* 14 Suppl 5, S1 (1997).
2. P. Zimmet et al., *Am J Epidemiol* 118, 673 (November, 1983).
3. W. C. Knowler, D. J. Pettitt, M. F. Saad, P. H. Bennett, *Diabetes Metab Rev* 6, 1 (February, 1990).
4. B. Newman et al., *Diabetologia* 30, 763 (October, 1987).
5. A. H. Barnett, C. Eff, R. D. Leslie, D. A. Pyke, *Diabetologia* 20, 87 (February, 1981).
6. A. L. Gloyn, *Ageing Res Rev* 2, 111 (April, 2003).
7. D. Altshuler et al., *Nat Genet* 26, 76 (September, 2000).
8. A. L. Gloyn et al., *Diabetes* 52, 568 (February, 2003).
9. Y. Horikawa et al., *Nat Genet* 26, 163 (October, 2000).
10. I. Reynisdottir et al., *Am J Hum Genet* 73, 323 (August, 2003).
11. R. Duggirala et al., *Am J Hum Genet* 64, 1127 (April, 1999).

12. F. Yi, P. L. Brubaker, T. Jin, *J Biol Chem* 280, 1457 (Jan. 14, 2005).
13. S. E. Ross et al., *Science* 289, 950 (Aug. 11, 2000).
14. E. A. Jansson et al., *Proc Natl Acad Sci USA* 102, 1460 (Feb. 1, 2005).
15. W. J. Nelson, R. Nusse, *Science* 303, 1483 (Mar. 5, 2004).
16. C. T. Falk, P. Rubinstein, *Ann Hum Genet* 51 (Pt 3), 227 (July, 1987).
17. J. D. Terwilliger, J. Ott, *Hum Hered* 42, 337 (1992).
18. J. R. Gulcher, K. Kristjansson, H. Gudbjartsson, K. Stefansson, *Eur J Hum Genet* 8, 739 (October, 2000).
19. Y. Z. R. Bagger, B. J.; Alexandersen, P.; Tanko, L. B.; Christiansen, C, *J Bone Miner Res* Suppl 1, 1 (2001).
20. G. Benson, *Nucleic Acids Res* 27, 573 (Jan. 15, 1999).
21. R. C. Lewontin, *Genetics* 50, 757 (October, 1964).
22. W. G. Hill, A. Robertson, *Genetics* 60, 615 (November, 1968).
23. C. N. Rotimi et al., *Ann Epidemiol* 11, 51 (January, 2001).
24. C. Prunier, B. A. Hocevar, P. H. Howe, *Growth Factors* 22, 141 (September, 2004).
25. J. Huelsken, W. Birchmeier, *Curr Opin Genet Dev* 11, 547 (October, 2001).
26. A. Duval et al., *Cancer Res* 60, 3872 (Jul. 15, 2000).
27. S. S. Fajans, G. I. Bell, K. S. Polonsky, *N Engl J Med* 345, 971 (Sep. 27, 2001).
28. C. Wolfrum, E. Asilmaz, E. Luca, J. M. Friedman, M. Stoffel, *Nature* 432, 1027 (Dec. 23, 2004).
29. J. Nakae et al., *Nat Genet* 32, 245 (October, 2002).
30. J. A. Noble et al., *Diabetes* 52, 1579 (Jun, 2003).
31. A. Duval et al., *Cancer Res* 59, 4213 (Sep. 1, 1999).
32. A. Duval et al., *Oncogene* 18, 6806 (Nov. 18, 1999).
33. H. R. Chang et al., *Cancer Lett* (May 16, 2005).
34. N. A. Wong, M. Pignatelli, *Am J Pathol* 160, 389 (February, 2002).
35. M. Lepourcelet et al., *Cancer Cell* 5, 91 (January, 2004).
36. V. Korinek et al., *Nat Genet* 19, 379 (August, 1998).

While this invention has been particularly shown and described with references to preferred embodiments thereof, it will be understood by those skilled in the art that various changes in form and details may be made therein without departing from the scope of the invention encompassed by the appended claims.

---

The invention claimed is:

1. A method of detecting an increased susceptibility to type II diabetes in an individual, comprising analyzing a test sample from the individual for a marker selected from the group consisting of DG10S478, rs12255372, rs7895340, rs11196205, rs7901695, and rs7903146, wherein the presence of a non-0 allele in DG10S478, a T allele in rs12255372; an A allele in rs7895340; a C allele in rs11196205; a C allele in rs7901695; or a T allele in rs7903146 is indicative of an increased susceptibility to type II diabetes.

2. The method of claim 1, wherein the increased susceptibility is characterized by a relative risk of at least 1.2.

3. The method of claim 2, wherein the relative risk is at least 1.3.

4. The method of claim 3, wherein the relative risk is at least 1.4.

5. A method of detecting an increased susceptibility to type II diabetes in an individual, comprising analyzing marker rs7903146 in a test sample from the individual, wherein the presence of T allele in marker rs7903146 is indicative of increased susceptibility to type II diabetes.

6. A method of detecting a decreased susceptibility to type II diabetes in an individual, comprising analyzing a test sample from the individual for a marker selected from the group consisting of DG10S478, rs12255372, rs7895340, rs11196205, rs7901695, and rs7903146, wherein the presence of a 0 allele in DG10S478, a G allele in SNP rs12255372; a G allele in rs7895340; a G allele in rs11196205; a T allele in rs7901695; or a C allele in rs7903146 is indicative of a decreased susceptibility to type II diabetes.

7. The method of claim 6, wherein the decreased susceptibility is characterized by a relative risk of less than 0.8.

8. The method of claim 7, wherein the relative risk is less than 0.7.

9. The method of claim 6, wherein the marker is DG10S478.

10. The method of claim 6, wherein the marker is rs7903146.

11. A method of detecting an increased susceptibility to type II diabetes in an individual, comprising analyzing a test sample from the individual for marker DG10S478, wherein the presence a non-0 allele in DG10S478 is indicative of an increased susceptibility to type II diabetes.

12. The method of claim 1, wherein the non-0 allele in DG10S478 is selected from the group consisting of: a −4 allele, a 4 allele, an 8 allele, a 12 allele, a 16 allele, and a 20 allele.

13. The method of claim 11, wherein the non-0 allele in DG10S478 is selected from the group consisting of: a −4 allele, a 4 allele, an 8 allele, a 12 allele, a 16 allele, and a 20 allele.

* * * * *

UNITED STATES PATENT AND TRADEMARK OFFICE
CERTIFICATE OF CORRECTION

PATENT NO. : 7,585,630 B2 Page 1 of 1
APPLICATION NO. : 11/454296
DATED : September 8, 2009
INVENTOR(S) : Struan F. A. Grant It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 306 days.

Signed and Sealed this

Fourteenth Day of December, 2010

David J. Kappos
*Director of the United States Patent and Trademark Office*

SEQUENCE LISTING

<160> NUMBER OF SEQ ID NOS: 53

<210> SEQ ID NO 1
<211> LENGTH: 74930
<212> TYPE: DNA
<213> ORGANISM: Homo sapiens

<400> SEQUENCE: 1

```
cttgtgtagg aactcacgct ttgtttattc agcaatcatt cctccagaaa taaccttaat    60
agcaacaaga aaaagaata ggtgtttttt gagctctatc tgccagtttc tctatatatg    120
gacattatat attgcaacat aacactcaca atgcctttaa acatcatccc cgttatacag   180
ataagaaaac agaatttcaa agaaggtagg ggacttgccc agggatacat agctagcaag   240
tggcagcgct ggattgagtc tgggccttgt ctgaggctcg ggtcctgtca tgctctgcgg   300
ttgctatgtt gacatgcaaa gggagaggca gctgctggga gtctaggtgg gtttctcttt   360
gagaatgcta acgtgaaccc tcaaggtgaa tcagaatcct tttgcaagtg aataatcaga   420
tgtaggttcc tgtgtctccc tgtaaaatga aagcctcttt tttccaaggt ccagtataga   480
cctgaagctg ggttactctg gaatttccct ctctggctgg agtgactgag gccttgcacg   540
tgacattggt gaggactcgc agcctcaggt ctggcttccc ttagcaaccc cccttttcctg   600 tctctgcctc tggagttcac cattaaaaaa aaaaaagaa aaaaagccaa aacactttat   660
aaagttacat gctgggtttc ttctatgtcc tagaaactgt cttaattcat cttcccctt    720 actcttatat gagcaggaag aaaaaaaaat tgctagtcaa tgctaataat tatggcatgt   780
aatgtaattg gaagtgtttc actgacatgc tcatgagagt ttgcggcttc atcttcaggc   840
tgggatgtag cactagactt gccttgagtg tctgcacaag cctttgatgc aggtagacca   900
tattataaat aggcgcgttg ctatggtgag gatggcagtc cttgcttgct gtgggtaacc   960 tttttctacct tctcggacac tgttttaaaa cacagcagcg tgatagcatt tcatttaatt   1020
tggaccaagg tggggtagat gaaatgttga gatttagatc taaaatgttg ttgtggtgtt   1080 tcaggggtt ctggctcacc tagtactatg gaagattttg cagattgggc ttcctcatga    1140
```

```
tttatttaga aatagatttt ctaatagatg gggtgagggg agggtggtgg gcagaaggct      1200
gggctttctt ctcttccccc tcctcctttc attgagcgct tctgcgaatg tgttggcttt      1260
gatgccccag gagctcatac agtgaaatgg aagttcaggt tggcacgttg cagaaatgat      1320
tattcctggt agtacgtttc ccattactgt taataatata aagacaattg cctgcctctc      1380
aggactcctg cacgtggcta cagtcatttc ttcatggaat tagacacata gcagtgggga      1440
ccaggagtgt tttattagtg attgtcctcc tgcaagtttc cagggtatct cagcttagac      1500
acatgaatta ttttttcctg ttgcttggag ggtactttt taattatatt cattcaataa       1560
cagagcagtt caggtttgta aaatatttt tctcccccaa ccttttcccc agcatacatc       1620
cccgtcccgt aagtttctgg gcagagacaa tctcaggaac ctaaaggttg ctaaaaaatt      1680
agctagttgg ccaggcgcat gactcatgcc agtaatccca gcactttggg aggctgaggt      1740
gggtggatcg cttgagccca gaaattcgag accagcctag acaacatggc aaaaccctgt      1800
ctctacaaac aaaacaaaat ctagctgggc atggtggtgc atgcctgtag tcccagctac      1860
tggggaggct gaggtgggcg ggcgattgag ctcaggaggt ccaggctgca gtgagccgtg      1920
attgtgccac tgcactgcag cctggatgac tgagtgggac cctgtctcaa taataaataa      1980
ataaataaat aaaaaataaa aaaaattagc tagccaagct gcttataggt cttttacatg      2040
gccaagccac tttctcacct ttaaaatggt aataacgttt ccgtactcat ctcaatgggt      2100
tttgagtgcc aagacagacc gtttgatgga agccctctgg ggagaaaaat gctacccaag      2160
acaggctttt caattggaga ctgatccatt ggtgttttgg tcagttggtg ttgaaatccc      2220
tattttccca gctcaggact gcctctctcc ctggaactct tcccgaggtg agttctgcag      2280
ccttccttgg gaactctcag cctctggatc ccttcttgcc aggtggagtg gacatgccaa      2340
agttgtgggc cagactcgga ctgcctggct tgtctcagca cctttgggga cccacttccc      2400
ctctctggga actggggaag ctaacagaga tcttgctagg ggggtggaat cctgtatcca      2460
tgtgaggttg tacccccagg ctcctgagtg gtttgaaagt ggggaaccct ggccgggcgc      2520
ggtggctcat gcctataatc ccagcacttt gggaggctga ggcgggcgga tcacaaggtc      2580
aggagatcga accatcctg gctaacacga tgaaaccccg tctctatgtg cgtggtggct       2640
ggcacctgta gtcccagctg ctcgggagtc tgaggcagga aatggcgtg aacccgggag       2700 gcggagcttg cagtgagccg agatcgcccc actgcactcc agcctgggcg acagagcgag      2760
actccatctc aaaaaaaaaa agaaagaaaa aaaaagaaag tggggaaccc ctcccccagg      2820
atgagaagag ccatggggtg agtctctgcc accgccaagg ggagtcaggc tcagaggctg      2880
ctacagggac agccagctct ctttagatgg tccccaccat ctagtcaggg cttgttacat      2940
atggagcaga gacagcgcag gctgctgctg ttttcctgga gaaggcccct gtcggtctgt      3000
tcagctgtag ctgaccttc ctccttgtgc tttttgggga gggagccttg gaaggagtag       3060
ggcacgtggg gcactctgct tcccggcccc acactggcga acctatggat tctgcctctg      3120
attcctgagg aaacatcact gtgaaggtgg aatgagccac atacagaggt ggctgttggg      3180
gccggggagg ggtgaaacgc ccccaggtgt acattgcac caaaagccag gctgcatata       3240
gacctcagga tgggctggct tttctatta tttagaagta tttccagagg gtaacctcat       3300
tggctacaaa gcatgtctga acaagagctc cgttgttcat tcccagccct gttaccctgg      3360
caggatgcag actccaggcg gcctgttggt caggccttgg actcagagag cagtgaagcc      3420
tgaggagggg tgggggcag aggcgtgagt ggtctagggc ctcagtccct ccaggacacc       3480
ccttgccaag cgcagagaaa gctctgccca tccgtcccct caggcagtgg gattgggcaa      3540
```

```
cctgggaagc agtgaatgtg cgtcggtagc atagattcca ttccgcacgc caccctcgcc    3600
tccgccccccc agccctggga gggatgcatg ccctccggga gacacccaga cccgacagag   3660
aggcctttgt tggagctgga ggtgagaatc tgtgggcgtt gggattcctg ggttcgagtt    3720
ccagctcact gccaattgcc cgagtgctgg gcgaacattt ctggaatcaa aaggagtgca    3780
gcctgcccag cagggcctac gggagccgga ggctgcaggg tgctaagatt gcgttatctt    3840
taccaagtgc ccggagctcc tgggagggaa gagagagtcc taggactcag gataggaggt    3900
ggttggagtt tctcgaggaa gactccatgc tttggttctg gccctggaa accctcctg      3960
aggactggac ctccaagcag accccctctg tgactccgga atgcagtgtt actctcttat    4020
attttctttt cttttttttt ttttgagacg gagtctcact ctgtcaccca ggctggagtg    4080
cagtggcacg atctcggctc actgcaacct ccgcctccg agttcaagcg attctcctgc     4140
ctcagcctcc caagtagctg ggattacagg tgcctgacac cgcgcctggc taatttttg     4200
tattttttagt agagatgggg ttttaccatc ttggccaggc tggtcttgaa ctcctgacct   4260
cataatccac cgcctcggc ctccgaaagt gctgggatca caggcgtgag ccaccgcacc     4320
cggccactgt cttgtatttc taacgtcccc ctgactttc tgatcatgta attcttaact    4380
ttctcaaaac tgagatttgt cacgtgtcct ctccccactc catttgtga atcagagtct     4440
tccaggggca ggacctggag aatgggtctt tattaacaca catgtgaaaa tgcttttgcc    4500
agcaaggcgc ggtggctcat gcatgtaatc ccggcacttt gggaggccga ggcaggcgga    4560
tcacttgagg tcagcctggc caacatggta aaaccctgtc tctactaaaa atacaaaaat    4620
tagctgggtg tggtcgtggg cacctgtagt cccacctact cgagaggctg aggcatgaga    4680
atcactggaa cccaggaggt agaagttgca gtgagccgag atcacaccac tggactccag    4740
cttgggtgat agagtgagac tctgtctcaa aaaagaaaa aaaaagaaa atgcttttgc      4800
catgggctgt ctcctgcttc tgctttgcat tgggcctctg tacctaggtt gcaagattcc    4860
tcagggtgca cctgggctta tcgttatctg taagttatcc cagcaagcac ttaaaacaca    4920
gtgttggacg atgaatcccc tctacaagag agggacaggg caaaaacgac acctcttgcc    4980
tcgcaagctg tcttgggcca aacctcaggt ctattctttc ttttttttga agtagtggc     5040
tgggcacggt ggcttacgcc tgtaatccta gcactttggg aggccaaggc gggcggatct    5100
tgaggtcagg agttcgagac cagcttggcc aacatggtaa aactccatct ctactaaaaa    5160
tacaaaaatt agctgggcgt ggtggcgcat gcctgtagac ccagctactc aggaggctga    5220
ggcaggagaa tcacttgaac ctgagaggca gaggttgcag ttagctgaga ccatgccatt    5280
gcactccagc ctgggcggca gagcgagact ctgtctcaaa aaaaaaaaa aagaaagtag    5340
cagctctact gagatattta gaaaccataa atccaccta tttgaggtgt acaattgagt     5400
gatttctgt atagtcacag atctgtgcag tcatccacac cctctaactc caggacattt     5460
tcctcaccccc cgaggagaaa cctcccttac ccattagcag tcactcctca tttcctctcc   5520
ccccagcccc tggcaatcac tgtggatttg cctgttcttg acatttcata taatggtat     5580
cataaaatct atgggctttt gtgtctgtct gctttcactt agcatacggt tctcaaggtt    5640
catccagtat tgtagcatct atcagtatgt cattccttt tatggccaaa taatatttta    5700
ttgtatggat agacattttg tttattcatt tatctgtttt tggttattat gagtaacact    5760
actatgaaca ttttgcacaa attttgtat tgacatgttt tcatttctcc tgggtatagt    5820
cctatgagtg gaattgctgg gtcatataat aaataactgt ttaacatttt ggggagctgc    5880
```

```
caaactttta aaaccttggg ttctgtgatg taccagttgt gttaggcagc acagcaaaat   5940
gtgacttttg attgccagaa acaatattta aaaagtggtt ataaaaagtg gtttgggagg   6000
ctgaggcagg aggatcactt gagcccagga gtttgagacc agcctgggca acatagtgag   6060
accctgttaa aaaaaagaa ggccaggcac agtggctcat gcctgtaatc ccagcacttt    6120
gggagactga ggcgagcaga tcacctaagg tcaggagttc agaccagcc tggccaacat    6180
ggcgaaaccc catctctact aaaaatacaa aaattagcca ggcctggtgg tgggcgcctg   6240
taatcccagc tactcaggag gcttgaggca ggagaatcgc ttgaacctgg gagactgagg   6300
ttgcagtgag cggagatcat gccattgcac tccagcctgg gcaacaagag cgaaactgtg   6360
tctcaaaaca aatgaaaaga aaaggctgtc atgttagatc caccctcctc ctcagggaa    6420
cccctgggct gctctctggg tagagatggg aacccaggcc tcgggccagt gagtggaagg   6480
aaactttggg atgattgact tgggactggg ctagaggtga agaatctccc agtaggcaaa   6540
gttcggcctt acgttttttt gtttcaagca aaccacatca ttacccacag aggccattgg   6600
tgagatattt gtaagtctcc tgacagtggc tggagttcgt tgcttggttg ttgtttctct   6660
gtctcagccc tggagatggg agtgaccacc tgctctctct ggacagaggc tgtccacgtt   6720
catgcaattc cttggacacc ggtggtgcag cgggaggcgt aactgggagt gggagaccct   6780
gaactgtgcc ggttcttgca gagtatcact gtgacttcag gcgagtcacc ccacatcagg   6840
cagctcagaa caagggattg atctagaagg acctttcacc tgggctattc tgtgactcaa   6900
attatcttct cctaagccca ctactgcctg gtgtgttggt taaattagcc taaaggtcat   6960
tccctcggag aggccctctg ggaaacctcc ctttcctgag agtcactgct tgctggcgcc   7020
tgccctggg gttccttcag agtcgtgatc atgcccggc tcttcctttt atttggcagt     7080
cccttccctt ccccatccct gatgagggta gggagcatct gtctgcagct tcatcttcat   7140
tgtctagggg ctccagaaat atctgtgagt aaataagtta tttaatcttt gcctcaaatt   7200
tccagtgact gtagggatat agctgtgagc ctctaggagc tgagattttt taaatttccc   7260
acttaaacat ttatttaaaa atttttgtgct cagcatggac taaggacttt acattcatta   7320
actcatttac agcttgatcc tatgcggtgg gcattcattt acagaggatc ccattttaca   7380
ggtgaggaag aggccagcta ggggtgcagc ctaggttagt attctagagc tcatcaggct   7440
gtgttgtccc cagtgaaaga ataagcaaag aagtgaatgt tgtgcattga aaaaatgac    7500
tctcggagga ggatgagcct ctcggatatg gcgaccgaag tgatatgggg cccttgtcaa   7560
gggtctctat tatggcatca agaaaagatg ctgctttcgg tgatgcccga ggagagcctc   7620
aatatttac atgggaaacc taaaaaaggg gccatgttgt ggtctctgca cctaagatac     7680
taaaggaaat attttatgga gagatgcaac atgtcaggcc ttggagggaa accccaggat   7740
ccagatggtt gcactctcaa accagggccc cctcacctt ggccttcagc atttagtgtt    7800
ggaaccaata gcataagctt tggtcaggac ctttgatgga agccacagtg ctcattagtg   7860
accacggttg actaccttct ctctcctaag ctgacttctg gagggcacct gggatttccg   7920
gccagtgatc agtgctggtg aagcctgaag gccaatgtgt aggtttagct gttcagtcag   7980
aacccaaaag gggccaaaga gatggtttcc ttcaacctcc actgagggaa gtgaaagtca   8040
tggttcgtta aaaggctgag ctgggaccag agtctagggt tctagaggtg ggaatttcta   8100
cagctttggg ggaccttgca agggcatttg ctcttctggg actgcaggga gactgtgctt   8160
ctcagagatg ttagcatttg gcttggggag agagaggaaa ggagaggttc atgctccgcc   8220
atgatggtgg aaagtgatgt tggtgtggtg aggagctgag ctgaattcta agtggttcca   8280
```

```
gggaattaac aatgttcctg cccaagtgtc ctgttccccc acaaactaat gaggcagcag    8340
gtgtctgaag agaaacattg cagaatgtct gccaggggtt ttatggttaa ttttcctcca    8400
ttatgagggt tgactcagcc ttgggtatta gatgtctttg agaatccagg gttcaaatac    8460
cacagctggt agaatgtttc tcaacttgga gccaatctcc atctactgaa ggtacgctgg    8520
tttagacaga caacagggac atcagcattt taaaaagcgg tggaaaaagt ttgcttgtct    8580
tgattggagc catgacattt tattttgaaa tttcaaataa catgaaggga ggtttggagc    8640 ggttttggt ttatccaaag ggcagtggat tgaaggctga gaaacaccag gctgaatggg     8700
agaggggttg gggtccccct gtgagatagt gaaacaatgg tagtgccatc caatgatagg    8760 cactttctg tcattcagaa gcagaaaggg ggccagaggc ccattggcct tactgggcag     8820
taagctgtag agctgctgcc ttttcgtgaa agggttgaca ccaaccttct cccccaggaa    8880
gagtgaccag ggacctgagg ggcatggtcg agcagatgac agcctttgta aaacatctcc    8940
ctggtctcat cagcgatatt cgtcctgcct tccttctgag taatttccat cttaggactg    9000
gagtcaggtg gagcaagatt ccatgttggt ttctgttggg cctagagtgt cacactgaga    9060
cctaatttca tactttatga attctagtac tgctctcgaa ggtaagagcc gtcctctttg    9120
gctgaaggtt tttgcctgca accttgcatt gtaatccagt gacacctgac gtatctgtaa    9180
atttcttcaa atttctaagt gtattacaac cccgtgtgca aaagatgatt aattaattgc    9240
cttgacagta aaacaaaaaa caaaaaaaag gtgtgggggt atatggtatc cctgatttac    9300
tatagaagat gcagagagtg aagggagatg aggtggggag gaggggccca ggttctggtc    9360
ctactttttt tttttttttt ctaaagagat ggagtcttac catgttggcc agtctaggct    9420
tgaactcctg gcctcaagag gtgctctcac ctcagcctcc caaagtgctg ggattatagg    9480
cgtgagccac cgagtttagc ccaggttctg tttcttgctt agtcactttc tgtttgaaca    9540
aaattggaat ttccttttg gatctgtttc tttaattgta aattgaatcg gactaaaacc      9600
tttccaattt tttcacatgt gaagacatac acaaagtttt tattggaggg ttgcacatgt    9660
gaaagaaaaa gggagaaagc aggattgagc aggggagcc gtcagatggt aatgcagatg      9720
tgatgagatc tctgccggac caaagagaag attcctttt aaatggtgac aaattcatgg      9780
gctttctctg cctcaaaacc tagcacagct gttatttact gaacaattag agagctaagc     9840 acttttaga tactatataa tttaattgcc gtatgaggca cccttagttt tcagacgaga     9900
aaccacagtt acagggaagg caagtaactt agtcaatgtc agataactag gaaaaggtta     9960
gaggggccct ggacacaggc ctgtgtgact gagaagcttg ggcacttcac tgctacattt   10020
catctcttcg ctataaacat tttagctttt tgtgtttgct gactggcaac aatacatagt   10080
gaaagttcta ataatttgta atgcttttgc atgtctttgt attttttcttg gttatcacat  10140 cacatcaaat taagatactg atcagcagtg tgagaggtta tttttccatg tcctcttcat   10200
tagtgttagc ttgtggatgg atttgaggct ctctgtgctt tcccccagc aaagtgaata     10260 ccagactttc ctattaaaaa aagtatttta ttttcagag acagggtctc attctgtctc     10320
ccaggctgga gtgcagtggc acaatcatag cccactgcag cctccaactc ttgggttcaa   10380
atgatcctcc tgcctcagcc tctcttaagc agtgcctttc cccattctca tgggactttc   10440
caatccatga gatactttgc tgcagggaag ccctgtctgt ccaggcctgt gtaatagacg   10500
acttcacatg gtcctgtgtt gttgtttgcc ttctgtgtgg ctaagtttcc atgacctggt   10560
ggcttggaag ccccatccct gatttgtggg agaggcaggg aggcaccttg tagcgcacta   10620
```

```
ggcgttgggc ctgaacaagt ctgtgtgctt ccaatgtctt tgtggggagg tttacgagtc   10680
cttcttatta tataatagta tcttgtctta gcttggtgcc tttcttctca gaagcttgag   10740
gcactctgca gataccatct caatttgctt tctgggagga ggagaggaag ctacccaaaa   10800
gatgaagttc tctgtgaggg gcttgaacac aggttgatag cgttgctggt tagttattct   10860
catggtgtgg atgaaaaatg gaatacgctg aaatttcagt tactcgtcac aaaaataagg   10920
cgtatgtaga aaacatcctg ggctaagggt ttgcatgctt ctagaacttc ctgttactta   10980
atggctgttg agtataaacc tcgggaacag tggggatcct tggagacccc aaataacttg   11040
tatttgtggt tactcctgtc ttgtctatca atacccctgt ctatatcgtg ttagaactag   11100
gacacacaga ctggattcag aagctggcct ggggtttagg agaacatggg acctaatcct   11160
ggccatctcg atttacctcc tggatcttgt tttctcatct gtaaaatgaa ttggggtgtg   11220
gactgtttat ggcctgtagg atgctagccc tgagaatttt ctccagatat tctacggtta   11280
agtaatttta ggggacactg tctaagcagt tgcctcttgg agaatgaaga tgttcattag   11340
gatattgaag gctctgagaa gtcctaaagt taaagaaaat ctgcaatgtt ctttgtggga   11400
ccgaataatg caacctggga aatgagggat tagatgacac ttgagtagcc ttccagatct   11460
gagacgagtc tcactctgtt tgtttactcc atctgtgatg ggtgtaggca ccatcttggg   11520
gagcaagctg tgatagagag ggaacaatac cttgttaatg tttgtctaat tcactaccca   11580
ggtgcatggt agtgaattag acactacttt gtaggttctg gagggaagaa gaaaagacga   11640
gacctgcctg gactggggct tgagaccact gtcaaataca agtacagttg tacaactggt   11700
agggagtggg tcatagtatg gccggtcttt ttaaaggtga ggaattctta ggcccagaaa   11760
ggcaaagtga cagatcctgg atttaaccag cagcccagat ttgaggccta gcacatagca   11820
aagcaccata gctattcaat agctgccaag tgggagtttg gatgatggct ttcctggaca   11880
gcgaaagcag tgatgtttgc ttaggatggc ctttggcagt gctgctgtta tccttaccac   11940
tggcaagcca tctcacgggc ccggagggga gggcaaggaa tcctaattct gtgagaaggc   12000
tctgggtaca tgagtgtgag atatggatac cctaggctct gcccctgaag acagtggcat   12060
cggatttact gcactattcc agtcggacag gcaccttaat ttttctcttt ctgggtgttt   12120
gatatggttg ggtcctattt cttctcctcc aaacccgct agggccattc cccacccttt   12180
cacttcccgg ccttccactg cagtctctaa ggattctgct tcatctttat gtgtgaacag   12240
ggttttgaca acatgatta actgggtatt tttggaaggc tcaggaggaa cgcagagtgc   12300
tccggagggc aggcctggag tcaggaatgc ttcctgcaac ctgttcgtgc agtgagcgtg   12360
tcttcctcgc cctgcccttg gctgggaat gtgctggctt ggagggcagg agagtgacag   12420
gcggtttgag aactccggc tctcccgtct tcggatggct cctgtgaaag cagggcctga   12480
aacttttatc gtcactgctg caggtgaaag actttcattt ggctgtagtg gtccaacaaa   12540
gagtatttta tttatgtgtt ccaagcccct taaaaattct tttagggcac atcagtgggg   12600
agttaataga aactttgaaa taagaaaaat gcctgcaggg taagtagaac cccagccagc   12660
cagctccgag ttctgtgctg ttagctggta ggttggttct cagagaagtg gctggctggc   12720
tgggttacgg agcccacatc tctaatgcct tagtgttcaa tcattaagtg gattttttt   12780 tttcccttct cttcttttgg tttggaggga ggactactct aaactttact cagggcaggg   12840
tagctcctga aagggctccc taacctttct ggtttatgac acaaagaaag tttggaggta   12900
ctgggataag agatggcttg ggtgacccc ctatcatgcc ccctaacaca tacacagcaa   12960
accaaaccaa ctcaccccttg atcatactcg ttgttttacac gaagggaatt tttattgtct   13020
```

```
tgtgagtgtt gagtgatgat taaacagaag agatgtgact ccaagcctgg cttcactaag    13080
atagtcttgt ttgtttcttt tcctccaaag taatttccta aagaattaaa agccccttttg   13140 aaacccagca ctaccttgtc tctgattatc agcataggca ggaagggctt ttaaggtctg    13200
agcccagctg tttagaggct acgagacgtg aggcaaatcc tggtatctct ctttgggcct    13260
cagtttcttc atctgtgaaa tggcacagta ctaccctcca ccaaggatga tgatgagaat    13320
taaatgggat gacaggtttc atccccagct cctgttctta ggaaggaaaa actgtgactt    13380
atgaagcctg taggttgtgt tcaggtttgt atgaggcctc ggacttcata caaaggtatc    13440
aaagtggcaa accctgatcc agatgttttc agttcagtca gctggtcctt gagcctgttg    13500
tgtgccagat atcctgacca aagaagctag atgggagctg ctgtgttgtt ccttggggct    13560
gctggatgca agttgtttag gtcggcggtt ttcaaatgct ggtgattttg ctcaccagag    13620
gacatttggc aatgtctaga gacatttagc atggccagtc attgggaggt actcctggca    13680
tctcgtgggc agaggctaag gatgctattg aacatcctgc aatgcccagg acagccccct    13740
gtgacaggag tcatccagcc caacatgtca ctagtgctgc agtggagaag ccctggctgt    13800
gtgtgggggt gtgtgtgtgt cctcttctac atttgataag gtaactcaca cttgctgccc    13860
ccatgatcgc tgtgggggat gcttatctat gccccagtcc tggtgttggt tgatgggaac    13920
atcaagattc aggcaagatg gaaaatagcc cttagaacta gcaggaaaag aatctccttt    13980
catttgtcta gaggttctgt taaagtgcct ttgcttctat tttgagactt gttcttaaaa    14040
aaaatgcgga tatgaaagaa aataaaaacc acattatccc tccacttttt cttggaggag    14100
gatgtgttga agaagtcaaa gttcaccatc cctttagata gaatcatttt gaacaatttc    14160
atatgtcaat acattttgct catctctaaa tttcattttta gagcctgtgg tgttctgtgc    14220
atggatatgt gtgcgtgtat gcacacaaaa ataaaaggaa atatttattc ttatgaataa    14280
gtatagaaat aaattaattt ttggaatctc aaactatcag agacttatgt ataaccaga    14340 ggcaggcctg attatgtatg ggcaaagcat ttgtgaacaa tgtctccatt gtataacata    14400
caaaacaagc ttttcttcca cattggatat gcaagtcggc cttctccaat aagggcctgt    14460
ctctttccaa ctcccccac ctcccacctt tgagcaaaca ttatttattg tggctgatgt     14520
gtgatcaggt cttgatttgg ggcctctttt tgatgccttc tctttgtggg atctcaccca    14580
cgtgcccctg gagacccttt ggctgccagg gcctttgttt cccagccacc catgtggtgc    14640
cagtagtgtc tgctttgtag cgagctgtcc ccagagcctc agcatggctt ggggatggtc    14700
tctgaggttg ggcttggatc cctcccactt ttgggctcag aaagaatgac tgccctctat    14760
ttccctgtcc ctgccctctc ttatcctgtt tccagcccg catcatgtta tctttgcttc     14820
ttgtaactta ccaaacgatt tatgggcaag taggggaggt gaagagggaa ctcatctatc    14880
aagataacct actttgtgcc aaccactgag catagcaatt gtcccttctc cagccctctg    14940
aggaccgtgg atgggattct catgaaatga acaggtgag gaacttttct tttagggaac     15000
ttgcttgagg tcccacaggc agcgagtatc aatcaacgtc aggatctgag ccctgttctg    15060
ttcggctgaa aatatactcc ctgagatggt gtaggccacc atggctttca gcaggctctg    15120
tgcttggtgg aaggaagctg gaagctgtgt acacacccac ggggaacagg gaccatagag    15180
gagcaccttt tgagtgcaga acctggcgaa acatacacct ttagagggat tttaggtacc    15240
cttgaggctg ggagaatcaa gcagagctaa gtttcccatt ggggtgtcac agactgaaga    15300
aacagagccc taggtagcac agggaagttg attgcccagt atcagttagt ttggctttaa    15360
```

```
tgactgagaa gagattccac cagttcattg aagagagggc ggacttttta ttggaggaaa    15420
gaagagtgcc tgtaagtaga gaagtctccg gggtgtagtg ctgtttgggg caggaagaac    15480
agtgtgagcc actgtggaga gaaagcccaa agagtcttgg cagggcaggg agtaggatgg    15540
atttgaagcc agaggaagta tggggtctct gtagactcca ggcaagccat gttaatattt    15600
taggaagccg tgatggagct gcagatgggt gtggaagtta agtttaact gttcattcac     15660 cagtccttcc cctggagaat gtgcagcacg tggacagtgg aactttaagg tccttggctt    15720
gtatttcaca cccaagagat gaataggtcc aggtatgtca tagaccagac taatgaaata    15780
acaaatttct tttcaaaaat tttacttttt gtaggaaagc ttctctgtct ggcatttttc    15840
ttctcccagt tgtgactcaa tcttaaacgt cttcagacaa ttagcataaa atttcccaca    15900
gtgaattgac gtatactttt gagggttcca tttctttttt attttttttt tcttttgaga    15960
tggagtttct cgtcacccag gttggagtgc aatggtgcca tcttggctcg ctgcaacctc    16020
cgcctcccgg gttcaagcga ttctcctgcc tcagcctcct gagtagctgg gatgtcaggc    16080
acccgccacc atgcccggct aattttcgtg tgttttagta gagatggggt tccaccgtgt    16140
tggccaggct ggtcacaaac tcccgacctc aggcaatccg cccgcctcgg cctcccaaag    16200
gctgtgatta caggtgtgag ccactgtgcc cagcctaggg ttccatttct taaccectcc    16260 ttctgatgcc tcagaaagtc ttgctctgta agcctcttgt agctgcctcg gttcagggga    16320
agggggaggc ttttgtttta ggaccgtcca gaccatagac acatttcctg gcacctagca    16380
cgtgttgggt caaacaggaa tgatgaatgc atgcatgaat gaggttctta gcgctgaaga    16440
cggtgtcata ggtggtctac cacgccgcct gatcattcca atggcccatt atgaatgtgt    16500
gtgctgcagg gccctcccac gatcccgtca gcactgtgca tgttgtgggg aggtgctggg    16560
agaaagactg ggtctcagaa gatgggttag aggtgggtcc ttctctgctg ctggctagca    16620
gggtagctgt ggaggggtgc cccatcttgc tggtcttaaa ttttctcact gtaggcaggg    16680
agcatgacct ggctgaattc taagtccttt tctactctga ggttcattgt gggtgtgacc    16740
tgctgggctc agctctggct ttgggagaca ccctctcccc ttgatctcga caacccctta    16800
gcagagccca gtggctccta cagtgccctg agctgcttgc ccgaaggatg cggttgtggt    16860
tatctcaccc cctgccaccc tgtttgcgca agggtttgag attgtgtggc ccctccttgt    16920
acttcggggt gaggcttgct ccagaaaggt ggtctgcaaa ggggttggct gggggggagg    16980
aggaagtcat tctccaagtg tttgtcctca tcgttatccc aaattgcttg cctggaataa    17040
ggaaggaaag aaaaaaaaat actcttgagt ggtttgggcc aggattttag ctgatggatc    17100
tggtagttcc ctctgtcaga tttgtttct ttgaactgtc tgggccggtc acagtgtcat     17160
tgtttaaatg tggaatgtag gtgttctgtg ttctgggaaa taaaaaccaa aactggtcca    17220
ggggatccac agaggtaaga aaagaacatt ccaataggaa tgtttcagaa ccaggagggg    17280
aggagagaaa aacggctctg ttggtctcct agaggaagaa cttgttagat ttggggagag    17340
tcaggataaa tttgaccccta agagtctctg attccttta gagactttc ttataagaaa     17400 taaaatggaa cttgggagag gcggcaactt gggaaacagc acattctgcc gtaatgaaag    17460
tcgtcccata agaatttctc tatcccttta gccaaatttc tgtttctaaa aggggaaaag    17520
gggctagaga taggcttgtt tgttttctta gttgaatctt acttttgta tttccagccc      17580 attctgcagg gtaagaacaa gcacagcccg agggctcact cagtgtgatg ttctagagcc    17640
tggctctgcc tcaatccctc acgctggagg atcaggcagc aggggccagt gatggatttt    17700 ttttcttcc tttcctcccc tattaatatt tactgaggta taaattacag caaagtgcgc      17760
```

```
agacctaggt atctaggact gtgaggtttt cctgtgttac ctgtgtaacc acgacccaga    17820
tcaagataag gaacttttct ggcatctcag aggctcttcc tgctcccttt cagactccgt    17880
ctcccagaag gaactacttc tgattcctat agccatagac tgaattttct tttccaactt    17940
catatgcata ggatcatcat gggtgtttta attttaattt catgtctgct tgccactccc    18000
aaatggaaat gtgttggcat ctctggatgt ttcttcataa gaaacatgcc ctgtggggca    18060
aagcccagga cagggctgtg ctgctgctgg aagtcctgtg cagctggcca gcctctgctc    18120 accctccgg ccacgctggc actttcagct tctccagcct cctgcccttc ccacttccag     18180
tcctgcacct gctgtcctca ctgatgcacc tgccttttc cttccgtcct ttatgtggca     18240
cacccttaag ggagacatct tcctgtctgt gttttgcacc ctcttaaaac tacattcctt    18300
tcccttcagc attggcatct ctgtccttgt gtattacctg ggatgactat tcagttaaca    18360
aatgctttct tcctaggctg tgagcccaag tttgttggat gattggatgg gggcacgttg    18420
tgtgagagaa ggatcatggg gtagcatctg gctctcttag aggtgtgtgg gggcgtgtga    18480
tgcctgccaa ggcgctttcg ttctggggggg ttctgtgtgt ttgaagcact tgggttgtgt    18540
gtccctgagg cctccgtcac gggcaacctc attccttctc tagcctccat cccctgcccc    18600
ctgcccaccc caggcctctg gagctggctc ccttttcctgc tcactctctt ttggccagga   18660
ttttaacata tatcacaggc tggtaggcta agagcttggg acttcccctc accacactca    18720
aagcctttga tcttttgctt tggaggtaac atcaaaagga aggctgagga agacagccag    18780
gctgtgaagt tcaacgttca agttaatagc ttgactgaag gttgtgctgc gttgtggcag    18840
catcaccgag gctggagtaa acagagtgat tctgccacat tttcctggaa atgcacccca    18900
atattggaag agggcttctt ttacattcgg aatgaattca ggctgtagtc agagctgctt    18960 ttcccttttcc ccatttttcct tggaagtgtg aaaacttggg ggagaagatg tttgtaggag   19020
ggcatgatga ggggtagagg aagcccaaag agaggatctg gggaggggaa gccccatggg    19080
atgagactct gaagttatcc ttgccccgat tccgggactt gctatctgcc tgccttttgg    19140
cgtggtgtct ctgtgccct gactgttcct gatttagcga ggtgtttctg aattctgatg    19200
gaattcaaag aagcctgggc aggcaggcag cttgacttgg ggcttgggga agcgtgcagc    19260
ccagacatag cagcgatgag agggcctcag ggctgagggc tgagatgaga atttcatcac    19320
atgcaaaagt gaaagcgacc catcgtcttc tccacttgat ctcttgctga gctttgcaga    19380
cactttggtt gttgtttaat ttaacatttt ctgcaatgct cctttttttca gatttttcatc   19440 caaagctctg tatgagaggt tttcaaaccc attttggccc tgattctatt tggcatacga    19500
ttcaactctg gggatggtca tcttccccac acctgcgttg ggtaccttttt tggtgtatgc    19560 tcagagcatc cttggacatc ttcctggtca gtgtccagca tcgtgaagct gcccttttagc   19620 ctctcagtgc cccagatac acctgtctct ctgcgtagcg gcactcagcg tcacctttct     19680
gtggggtctt gagaccctga tgatatcagc actatgctgc cagaattccc cttggattct    19740
ttagtgtggc ttctcaagca tcccttatcg ctataacgcc ttcatggttt ttggcataac    19800
tgtatactac ctgtgctatt atttatttga tgcattcaaa catttgattc atttatttaa    19860
actcagtctc actgtaatcc ttaattaaca cctgtgaaat tataggtttg atgtgctact    19920 tatttatta ttttttaata cacattagta taatcccgta acggctaaag taacactttg     19980
tactgcctaa aaccatgctt gggagcgcca cagtttgaga aagtgcttag ccttcctttc    20040
cctcctttag tgacttgtgg tttggggcat ctgttgactc ctagggctcc cttgttcatc    20100
```

```
tttctgttcc taagctcagg gattagttgc tcaacccagg tgtggcctca aaattctgct   20160
catggaatag cctcaggctt ctataaatct catctttttt gttttgtttt gttttgtttt   20220
ttgagactga gtcttgctct gttgcccagg ctggagcaca gtggcgcaat ccactgtaac   20280
cattgcgttc tgggttcaag cgatcctccc atctcagact cccaagtagc tgggactgta   20340
ggctggtacc accaggcccg actaattttt aaatttttg aagagatggg gtctcactat    20400
attgcccatg ccggaagtct agttttatag tgatgagaat tcatctgggg tccaaggggc   20460
cctcctgtgt tgcttcctgt gctcccctct aaataaagat actccttcca agttgtcctg   20520
attttcaggt catcaccatt ttttgagctg gatggggaag ttggcctgga gcagccttcc   20580
ctgtctccga gttgcattac ctcctgagag gtctcagcaa atcactgcca tctcttgatc   20640
agagttgctg gcaagagtcc tctgtggttc taggttttca gccctggaga ctctcgcctg   20700
cattcattat acatgtcctt tggtgccttt gttgaaaggc atctcctgcc accgaagggt   20760
gtgggcttct ggaaattctc agaaaacaca atatgccagc ctccagggat gggtctccaa   20820
agcttcagga acatatcctg gggtgttgag gaaacaccca ccttaaaatg ttcctcaagg   20880
gggaatgtta ctgcttgccc taaccctctt gagctgatgc tcacatgacg tccctgagat   20940
gggcttcttt tttgcccgta cttaaagctg taaagggcca ttgtcaaatt tgtttagctt   21000
ctcaattcat gttccttaga ggatggtaaa ttaaagttag cattcctgga cagagccttt   21060
catacattga agacaacccg gtgagtctca aggggagagg taagggagag atgaaaggtt   21120
ttctccaggc ctgttcggca gcatggactg ttcttttagg taattaaggg agaccataaa   21180
agacaattgt gtgagtccat ttacctttca cttgggggtc ttaagtcttt ggttgggctt   21240
ctttaaccct gtgtgtcacc cacgggctcc tatgggtgct gttttcattg ttccgttatc   21300
tagttggctg gaacacacct tgggggattg gagaatggag ttctgggggc tttgggaact   21360
ttgagttttc ctgcaatgtc ctatagaagc ttgagtctgt gattcctggg cagggccttc   21420
tcctagttga gtgagattgg tggggcaggg cagccagtta gggggtcatg ggagcaggtg   21480
tggaaaaggt tatatgtctt agtaattctt tgtgacaatc accctcattc attgatatct   21540
tcttcctatc atgtattagg gcagtggttc ccccaatgtg ctgcacatta ggttcacctg   21600
gagagctttt ataaaaatgc caatgcccgg ggcccacttt ggggaggagcc aggcatcagt   21660 aatttcaaag gtctctaaat gatttacagt ttgggaatca ccgtatgagg atagtaagct   21720
ctgagtccta tgcgttctgt gccgaacacc catgaagcag tcttccaagc attttacctg   21780
catcatctca attctcacac tgttaaggag atagacagta tcatctccat tttgtagaca   21840
agacaactga atctcagaga ggtttaagtc tcaggacacc aaggtcatta ttaatcaggg   21900
ggactgtgat tgctcccttt ataaaatgta ggagatattg tggagtacgg ttgagaaacc   21960
attgcaatag ttttcttact ttgttaagaa attaggctgg gcgtggtggc tcaggcctat   22020
aatcccagca cattgggaat ccgaggtgga cagatctctt gagctcggga gttccagacc   22080
agcttgggca acagggtgaa acccatctc gactaaaaat acaaaaatat agccgggcc    22140 tggtggtgtg cacctgtagt ctcagctact gagaggctga ggtgggagg atcacctgag    22200 tccggctgca gtgagctggc attgtgccac tgtactccag cctgggcaat gagagtgaga   22260
tcctgtctca aaaaaagaa aaaaaggaa attagtggtg gaaggtgact ttgcatctgg     22320
gcgtatctgc ctgcagagtt ggtgtcctta ccttgaagaa accctgcttt agttggagta   22380
tccttaatgt ttagtggcag gagggagga gtggttcctg ggagactgga acaaaatatg    22440
gtacctgaat gcttaaggct tggcagatga gcagtcattt tcttacacag agcttaggaa   22500
```

```
agggcatcca ggtagaggaa tcagcatgaa caaaagcaca gggccataga gttctcagaa   22560
ggaaagatgg ggttaaccgg agccaagcca gagatctggt ggtagtgggg ggtttccaag   22620
ctagaatggt tgtgtggtat tctgtcctca ggggctttga actctgtgtg ctaatgaggc   22680
ctcaaattct ctggggctct ggttaaaatg tagattctga tatcagttgg cttgggtggg   22740
gccttgcatt tctgtaagcc cttagcagtt gcactgctgc tactaccgtg agtattgctg   22800
ttgagcatta ctaccttgag tattgctgtc aagtgttact accttgagta ttgctgttga   22860
gtattactgt cgaattttac taccttgagt gttgctgttg agtattacta ccttgagtgt   22920
tgctgttgaa tattactact ttgagtatta ctgttgagca taaccacttt gagtattgct   22980
cttgagtatt accaccttga gtattgcttt tgagtgctac tgccttgagt atcgctgttg   23040
agtattgcta ccttgaatat tactgttgag tattaccacc ttgagtattg ctcttgagta   23100
ttaccacctt gagttttgtt cttgagtatt gctaccttga gtattgctgt tgagcattac   23160
taccttgagt attgctgttg agcattacta ccttgagtat tgctgttgag cattactacc   23220
tcaaggattg ctcttgagct ttaccgcctc aagtattgct cttgagcgtt actgcctcga   23280
gtattgccgt tgagtattac tcccttgagt attgccattg agtttagtcc tgtgagtatt   23340
gctgctactg cgccttggca atggttttca aactttgcaa cacatcagaa tcacttggga   23400
aacctttaaa attctaacgc ccaggtcaca tcccattcca actagatcag aacatctggg   23460
gaatgcgagc catgcaccag tagttataaa acctgcccag gtgattccaa agtgtgggaa   23520
cctttgagaa gcactgcttt aggggttgga atagtcctgg ctgaattttta atcagggaag   23580 actgactgct ccgtttatga aacgtaggag agtggagcag ggttgagaaa ccatcgggat   23640
agtgttctta ctttgttacg tgagcaatat ttgttgagtc tctgtggtgg gttctagggg   23700
ttcagaggac agcagtgtgc tgctaggatg gtggtctgaa ctagtggaaa ggcactcaaa   23760
ggaagaaaga cagaattcta agaggagagg aattttagga aggagatacc caggactttt   23820
gaattacagg taatttgatc agaacccaaa actgaaatgt ctctgctctg tgatgaaagg   23880
gtttgctggc attgagtaag gagctgcagg aaggccttta acttgtctcc aggtctctta   23940
acagctttgt catttacata caagcacctg cctggctaaa ccattcattt ctgtagcttc   24000
cttctggatc tgtctaggga atatttgctt tgcatatttt ggggttatct taagtgtttg   24060
aaggaaccaa atatttttc ttaaaaataa cactcaaatg tagttcacat gattaatttt   24120
gactgatttg tgagaatcag taagtgctga ctgactgagg cgccccacac atccggcttc   24180
cttctgttac tctacgcgtg ttgctgaaac ttaacgaacc catgtggggt cttctcgcct   24240
ggtgcagtcc ggcccagtat tcatactgag gtttgcagtg ggagaaagga aggtatttat   24300
ttgtaggtca ccaagcaggg caaatccagc agctcacgct taagacctga cctctcccat   24360
ggtttataag caagtggttt tttttttttt tttttttttc agactgagtc ttgctctgtc   24420
acccaggctg gagtgcagtg gcgtgatctc agctcactgc aacctccgcc tcccaggttc   24480
aagcgattct cctgcctcag cctcctgaat agctgggact acaggcgtgc gcccccacac   24540
ctggctaagt tttgtctttt tagtagagat ggggtttcac catgttgccc aggctagttt   24600
ccagctcctg acctcaagtg atcctcctgc cttgacctcc cagagtgctg ggattacggg   24660
catgagccac agtgcctggc ctgtaagcaa gtgttttaa agaaaggggt aaattttagg   24720
gaaacagaag ttctaggcaa aatggtaaat taatacaggg aggtaagaca ttggtttggc   24780
ctaaaaagat gggatatttt gaagtggggg ctcataggtc ataagtggat ttaaagattt   24840
```

```
ttttggtttg taattggtta aggaagataa gctttgatta aagatttggg gtcagcagaa   24900
agaaatgtta ggtctggctc gtgggcatgt ctttttctag gcccctcctt ggaaagaact   24960
ttagagcaaa gaaaggcagt tggagcttag tccccacttt ctcctgatct gaggtctacg   25020
gaccactgga tccatttggt ggggtccatc tttctgaaaa acaagtcagg gacatgtatt   25080
gagatgatat tattggtatt tatagggaac caaacaacgc cccatgactc tttttggct    25140
attgttttaa gccactgttt ttttttgttt attgagttgt taacttattt tttaaagcta   25200
gctagctgcc tggaatttct ttagaaggaa ctgaagtttt taaaaatttt tatgttgggg   25260
ggtattgccc tgcaggcccc taaaggggt ccctgcgctg tctcaaaact tggatgcaaa    25320
aagaagttga gttaacacag gaggacaggg gtagacgcac caagggcatg tgcctcgagt   25380
gcgtggtcct tattaagaag ggtggttaga cagggaatgg gttagttccc aggtcggcat   25440
tcagctgaaa cagtgatggt taaaattctg aaaaatgtcc acgctctgca ttctcttcct   25500
aacacccagg acccagtaac tataaagccc cctaccctgg ggcatagcag ggggcttcag   25560
ggacccatga gaaggtcatc tgctgctagt tacactcctt ctgggacctg atttagacag   25620
tttggtggta gttttgcgag ggttaatttc agggccaagg atgcttctag aatggaaata   25680
ccttcttgac attgggagct ttattggttg attatgtcaa tgtgagaatt caggaagccc   25740
agtgctaatc ctccatccta aaaggagtag attggctggg cgtggtggcg catgcctgta   25800
atcccagcac tttgggaggc cgaggggcg cggatcacct gaggtcagga gttcaagacc     25860
aacatggcga aaccccgtct ctactaaaaa tacataaatt agccaggtgt ggtggtgggc   25920
gcctgtaatg ccacctactc gggaggctga ggcagggaga attgcttgat cccaggaggc   25980
ggaggctgca gtgagccaag attgtgccac tgcctccag cctgggcgac agagcgagac    26040
ttcatctcac aaaacaaac aaacaaacaa acaaaaacta aaaggagatt tcctccttct     26100
gtcctttatg ggagacttca accttgggaa agtctggaat ccttggacat tagaaattct   26160
gaagttttgg ctggctgtag tggctcatgc ctataatccc agcacgctgg gaggccgagg   26220
caggtggtca cttaggccag gagtttgaga ccagcctggc caacatggtg aaaccccatc   26280
tctactaaaa atacaaaaat tagctgggcg tggtagcgga cgcctgtaag cccagctact   26340
tgggaggctg aggcaggaga atctccagaa cctatgaggt ggaggttgca gtgagctgag   26400
atcacaccat tgcactccag cctgggcaac agaacaagat tccgtttcaa gaaagcagaa   26460
actctgaaat ttttgcctgt ccaggccaca tcaatcccat tcctctgctg tctctgcagg   26520
attctgtgag gaataattag ttaatgtttg cagagcactt tgaaatcctc agatgaaagg   26580
caccggagaa gcacaaagta ttattattta ttattagctt gccccagaat ggaggcgcat   26640
gaggccctgg cagctccctg cctcgtgcca ggtgtgatcc tcctgctggg ctttcctgc    26700
ctgatgagct ttttttttt tttttttttt gagatcaggt tcagctctgt cgcccaggct    26760
ggagtgcagt ggcatgaaaa cagttcactg cacacagctc actgcactgc agcctcaaac   26820
acctgggctc aagcaatccc cctgcctcag cctcccaggt aactgggact atatactaca   26880
ggcatgcgcc accactcctg gctaattaaa aaaaattttt ttttgtagag atgggggtct   26940
cactatgttg cccaggctgg tctcaaactc ctgggcctca agatgccaa aggttcacac    27000
cttggcctct caaagtgctg agatgacagg cgtgagccac tgtgcctgtg tcaattgat    27060
tttctttatt aaagaaacat ggaagaaagt gaaggatgag aatcagtaac gtaacgtgtg   27120
cttcagattg tggacaagtg atgtgaagga aacacattgg tcccactgtg gtgacagagc   27180
aggggtttcc ttacctggca aggttgcggc tgccattcct tggggtctgg ggttaagacc   27240
```

```
atctgcctga gggtaacgca gtaataaatc agtactaaag ggcgtactaa agtactgtat    27300
tgctaggcta ggccatgctt ggtgtatttt tttttttttt taattgagac ggagtcttgc    27360
tttgttgccc aggctggagt gcagtggtgt gatctcggct cactacaacc tctgctgccc    27420
agtttcaagt gattctcctg ccttagcctc ctgagtagct gggattacag gcacgtgcta    27480
ccatgcttgg ctagttttaa aatatttta gtagagattg gttttgccg tgttgtccaa     27540 gctggtctca aactcctgac ctcaagggat cagcccacct cggcctcccg aagtgctggg    27600
attacaggca tgagcctggc tggtgtattt gttttaaatt taaagtttac taaatttaat    27660
gatatctggg gaatcagctt gcttcctggg gatctggatg tacttgaggt gagagggtgg    27720
ggattcagaa ttatcctttc tatcgcagca tgttctggat tgattcatgt aggtctcaag    27780
tgtgtgtaat atttcatttc tttgtgcaat tttggcatgc cgaggcgggc accctgaagc    27840
tccggcagag cctggagaca gagtgggag ctctccgctc tttcccttcc ttcatcccag      27900
ctgacttcga ctggaattga attcatcagc tgctggagag ttgttttatt tgccctgctg    27960
gtggagaggg aggaaaggaa catcatgggg ccaggctttt tttttttaaa ggaaagattt    28020
gatttacttt ccccttagt agcatgatgg gcacctgcac ccgccagcta atcagaagcc      28080
actgtcccct gaatgcctcc gctgccacc agatcctgac agcatcccac gcggagcac       28140 tctcgtgtgc ccctggcagc ttctgctgcc tggcagttct ctaaacttgc tggtgtctct    28200
ctgcccggag gctcagaaac ccagaggact gaccacttct tgaggctcat gtccagtttg    28260
caaagagccc ccagcaagca gagaagggga tttttgtacc agcgatatct cttctccact    28320
cctcaacaca ctcctttcca ctctgtctcc tataaacatg gaacagccag gaatactcaa    28380
atcctagcct gtcatgaagc caaaaattga tagagatcta ctgtccagaa tgatttctta    28440
tagtgaccct gtgtttagtt ggtaagactt tcttaaacca tgagggattc tggtcccaca    28500
gggcagtaat atctggggca gagcctgaga cttttctcat tgatttcctc tgtgagccag    28560
gagtgactgc tctgatgcag ggtgctgtgt ggttggtaga agctggcgtt atcccatttt    28620
acccacgagg aaacaaatga ccagtggtgg agcgggagct cagcatccca tgtgcccact    28680
tcctcctcgg gtggactttt cacctgccca tgccgtcttc tttgcaaact ttactgcagt    28740 gacgagaca tctttaaata caaattcttg ggggaaccct gtgttccttg gctggagcct     28800
ggctgggaag gaggagggag cagagggctc tcttgggtgt ggcctattgc agttgagcca    28860
gggaaaggct ggtccactgg agacaccctc tctggtcacc gcagacttcc tgccctccat    28920
ccagtgtcct tctacttgca ggatgtgtgc ccagcagaga gaatctctga gccatgtca    28980 ttattgggat aacattcctg tcccagtcac cttatttctc agaaaaagga caatgggaaa    29040
caagttttta ttgaatccta tgctgggcct attaatgggg tctcttactt ttcatagcag    29100
cactgcaaac agagttacgt ttctattcat tttatggatt agaaagctga gatccagagc    29160
gggcagatgt aaacctgggg tctttaaaat gcatcctttt tgcaaacaaa taaacttagt    29220
gtattaaaag ggctggagag agcagagtaa ggtaacattt gggtggtcag catgtagttc    29280
tgggtcccca cagtggagat ggcacagtgc tgggtgctgg gggaactatg gtcactaaga    29340
gacactgaat aatttaatgc atgccctga ttccatcact gactgttgag gtaacacata      29400
catttatatt gtcagtggtg gtgatgatta catgagctgc gtaaagcgtt tgaccagtgc    29460
ctgcacataa catagtaggt gctcaataaa gatcacccac tcttaagagg tgggaggagg    29520
tgaagtcatc tttctgggga gtgttgccct gttgttctct gctgcattct ttctgtcctt    29580
```

```
tgggctccga gaatgctggg ttgggcagtg tgagtggtct tctcaggcct ctgtgacatg   29640
ttgctttcat gaaaggttcc cctctagcca aagactgagt ggtccttgca ggctttctcc   29700
tgagtccttt ttttttttt tttttttttt ttaaagacag agactctgtt gccagattgg    29760
agtgcagtga cgcggtctcg gctcactgca accgctgcct cccaggttca agcaatctac   29820
aaaatgcatc tataaaatga tgcatcagcc tcctgagtat ttgggatcac aggtgcccac   29880
taccatgcct gggtattttt ttgtattttt agtagagaca gggtttcacc ctgttgacca   29940
gtttggtctc aaactcctga cctcgagtga tccgcctgtc ttgacctccc aaagtgctgg   30000
gattacaggc gtgagccact gcacctggcc tctctcctga gtccttttgt ttgtgcctgc   30060 tttgggatt ccctctggct ggggtggact gccgggatct gtttgtccag tgtacatttc    30120
ctggtcacct agcaccggcc agctgcggtg ctggaggaa cagggcctgg ctctgggagg    30180
cagctgggag agtcaggaag tgaagaaagt tcttgtgggt gtgatggtgg aaacccaagc   30240
agcgtccaga gggagcacaa gagggaggga caaatcttgg gagggtcccg ggccaatggg   30300
acccagtgta agaaattgca cctgtcctgg cagatagaga aggtggaagc agtgaatggt   30360
agagcatcct cactcttctc tctgccagca agcacctttg gggaagtcct cacgacagg    30420 aatgtcgtgt gtcttggctt gagatgtcaa agaaacatgt tggacacacc atggtgacag   30480
agcaggagtc tcttaacccc ggcgtggttg aggctgccgt tctggtggga tctgggtca    30540 gtcaggggtt aacagtcgct cctgcttgcc tgattgacac agtaataaag gcagtgacac   30600
caaactaggt ctcaggaatg tgtcctcgtt agaaagactc actaatggtt gtgggggggt   30660
ggcccatgag tccttctggg tggtggcgag aagtagggga ccctttgggc tttgccttt    30720 ttggtcatag gacttcactc cacagacata attgaaccgt tgggtttctg cagccaaatt   30780
caaatgtcac caatcttggt caccccttc atctcttggg tcctctgtaa gttatagcta    30840
tctgatagtt tactgaaaaa taaactgaaa atatgtttta aattgtactt tcgatttaaa   30900
ataatgttta gagacaaaaa aaagggtcc aatccacttg gagaaaagca ttgtcaaagg    30960
tggttgattt ttttctttg ctgttttaaa gtggtaagtg gatgagtgtt ttggatatat    31020 tgattttca ggtgtgcagg cggtcacatg aacagctgac atttttttt ttttcatgtg    31080 gacttcagcc agtcttgaca cctgccccctt aacgaaaagt aaaccatcgc cttgtttgac   31140
agtttaagtg cagtgatacg gatggaggca ggtttacgtt atgttaaagg cttgacaacc   31200
cagaaccccc ctgttggttt ctttgttgta acctttgagc cggtggcctg ctgaaatgtc   31260 accttttgccc ttcttaaaa gcaggaataa taggtggtga gtgggtggat gcctcttaaa   31320
atactggaaa gtgctgtggc ccgagggtaa gcttttaga agtgagtgtg tgtgttgtgt    31380
tgttttaatt aatgaatctt ctgggcctga agataatgag gtcagtgagg gcagccatgc   31440
tgcctcacag ctcaccttag ggtccttgtt gtccagaacg tgcctgacct actggagggg   31500
cctgggaatg cttctttgat tgacgtgggt aggaagacag atgtggcggc ctccatgctg   31560
atgggaggca gctgggaaga aggtcatggg caccatctca ggagtggcag agccacctcc   31620
ccctctcctc accccgtgtg tctggattct tccagctgtg tggtccttct tcctgcctgg   31680
aaatgagcat cctgcagagc tcggctcctg ttcacaccct cctcctaacc ccctactctc   31740
cctctccctt tcatccaggg ctggaggacc agatgggctt tacctgatgg agtgtgctt    31800 gctgacatgg tgcaaagagc caattcctgg ttgcaaagag gcagctgggt gcagaggcgg   31860
ggtgcattcc tgtaataata ataacttgtg tttttataat actttacagt ctaagtactt   31920
ttcaaatact tgacctcatt tagttctcac cacagccctc tgaagggata ttactattac   31980
```

```
cttcattttta tagatgcgtt aaccagggct tgttttggga ggtagagggg gtgtgagggg    32040
gacagagggg agggaaccag tgttgaatga attctgaggc cctgccaaag cagccagcta    32100
gctaggtgtt gttaatgga ctctttgcat ctacagaatg agggaggtgg gatgagggga    32160
aattatttca caataactga aggtcggaga gactaactct ctgctcattg tcacacagca    32220
gttgagtgcc agctgggatt tgtcacccag gtcacctgac tcctaagccc tgtgatcgtt    32280
ctcttctgtc tctagtatac ccagcataat gcccggcaaa gtgctggcat caataaatat    32340
ttgtcgaatg ttaaatgagg cttaaagaga accattcatg cttggcacag ggcacagtg     32400 agacaaacat gtttcctgcc ctcgtaacct tcgcttccaa attctgtgac cttgggcggg    32460
ttgcctgagc tcttttccag ctcagtttcc tgaaaactca tccggaaaat gggtaaaata    32520
tcagagtgca ttctgtatgg taagactgca aatgttagat gattctgcta cttattattg    32580
ttttcttttt ctcaccacac accttcccct ttttatgtaca cctcctagga agtaagtttc    32640
tgataacata ctgcattgtt ggataacagc aacaaaaagc acttcctgac attattgccc    32700
aaatcaccaa atgaggcaat taccaacttt ggaataagaa tagcaacggt ggtaagagct    32760
gacatttctt gagcgcttgc catatgctgg gtgtactact ataagctgct gcctgcaatt    32820
atgatttggg aacaactctg aaagtagtta cctcccattt tatagaagag taaactgagg    32880
ttcagagagg ttaagtaacc cccccagggt ctctcaggaa gtagttggtg gcctgggatt    32940
caaacaccag aattggtctg acttcccact ctttaaacca cactcaaaac tgaactctcc    33000
acgtgtgtgt gttctgggca ttttcgcatc tcccttggct tgttgacagc gtggactttt    33060
gctttcccat tctcatagaa catggccagt gcaggaggag gaaatccaca ctggtctttg    33120
gactgaacca gaggctggcg atggtcccga aacagggtgc caagtggctg acccttgttt    33180
ttatgccttg cgctggtaag cttggggcac caggagttct ttgaatttct ctttcttgac    33240
tgtccacgcc ttctttaggc aatcttttaa caggctatgt tttaaatctt attgacatct    33300
ctgaagaaag aggaggaaaa aaaaatcaag acatggcctt agagaagtga caggttttct    33360
ttgagatttt gttttctgtt ttccttttta ttttgtgcac attgcaaaac ctctttggga    33420
tgatgatttc gtgtggtttc ttggtagccc ttgggcagct gctgccaggt tcacccaaa    33480 tgcattgtga cccctgttt cgtgggacgg ctttgcctcc acatggctga ttgtgctctg    33540
tgtgtccgct gtgggcagag tgtgattgta agaatcagaa ttctgctggg cttgcaagca    33600
tttaaaaaat ctctataagt ttgagaactg gttggaaggg agagatgcag cgacttagaa    33660
cacccggcct gcagctgagc ttccgtgtgc ctgggaggag cccatatgga gaaacaggaa    33720
aattccactt caccagaaag ctggggaaat gagtgggagt aggggccagg ctggttaact    33780
aggaagactt ttggtcactc tgctttactt agcctaaagt gttcatttcc cccttaagcg    33840
gtggttaata cgcgtatctg cagatttact ttttggatga tttaaaatct tgcaacatct    33900
caagggattg tatcctgatg atactgatta tattaataac aagataatag cttataatat    33960
aatagctagc aattaccaag cacttacctt acaccaggta caatgccagg catttgatcc    34020
ttacacgaac tctgagagat ggctgtttgt attcccattt tacagatgag ggaagctgtg    34080
ctgagagagg tgagttcatt tgcccaagct cacccacttt gagatggtct gcttttatat    34140
cctcttagcc caattctttt ggatgtcagc acttggcatg tattaggcac tggataagtg    34200
ttttgttgaa tgaacaaaat gatgaacttg gatttgaac ccaggtctga gctggctttg     34260
agtcttcaga atagtaggtc caattagtgg agtggggget cagtagtcca aagggaaagg    34320
```

```
agcaaggaga cattgtgggg gccgagaaga gggcttctgg ggtgtttcct gggcacattg   34380
gcattaaagg catagtgtga agtgccattc aagaccatgt gctggattag tgttttcct    34440 ctccacttga ggtgcttgcg attggctttg tgccccggtg tctgcaaagt gagttgggct   34500
gaactcagga agaccttttg gttgggatga ctgtgtattc acctgcacct gagtagggac   34560
tgagtttcac ttgccagttt taccgcagca agacctcgtt aagttggctt cctctcattt   34620
aggcatttgg gaaactttag gcggctggag tttaattctc aaggcaaagc ccctttttcaa  34680 gggacatgaa gaaaggcaga gggatatatt taaaatacct gaatgaactg tttctttttc   34740 ttttttatttt ttgagatgga gtctccctct gtcacccaag ctggagtgca gtggcacgat  34800
ctcagctcac tgcaaccttc acctcccagg ttcaagcgat tctcctgcct cagcctcccc   34860
agtagctggg actgcaggtg tgcaccacca cacccagcta attttctat tgttttattt    34920 tatttttattt atttttttaat tttttttttg agacggagtc tcgctctgtt gcccaggctg  34980
gagtgcaatg gcgtgatctc ggctcactgc aagctccacc tcccgggttc atgccattct   35040
cctgaatcag cctcccaagt agctgggact acaggcacct gccaccacac ccggctcatt   35100
ttttgtattt ttagtagaga tggggtttca ccatgttggc caggtctctt gaccttgtga   35160
tccgcccgcc tcggcctccc aaagtgctgg gattacaggc gtgagccact gcgacttgca   35220
tgtagacagt aatggcaggt cactatcagt gggtctgtta atcaggtgtc caacctggtg   35280
ctgggcttgg tggctcatgc ctgtaatcct agcactctgg gaggccaagg cgagtggatc   35340
atctgaggtc aggagtacaa gaccagcctg gccaacatag taaaacccca tctctactaa   35400
aaatacaaaa attagctagg catggtggga tgcatctgta gtcccagcta ctcaagaaga   35460
tgaggcagga gaatggcttg aacctgggag gcggagattg cagtgagcca agatcatgcc   35520
actgcactcc atccagcctg gacaacaaag cgagactctc acaacaaaac aaaacaaaca   35580
aacaaacaaa caaaaagtca cttgcttctt ttttgcttg cttatggaca taaaccctgt    35640
aaactatctc atacatcatg ggagtgagtt tgcagtgggt agactgctat tcacaaactc   35700
atatacatcc tatgaaggag tacaggttaa ataaccatta tccaaaatgc ttggggctga   35760
aagtgttttg gattttttaat ttttttcaga ttttggaata ttcgcatata cataatgaga   35820
tatcctgggg atgggaccca aatctgaaca ggaaattcat ttatgtttta tataaaccct   35880
tttttttttt tttttttttg agacagagtt tcacgcttgt tccccaggct ggaatgcagt   35940
ggtgtgatct cggctcactg caacctctac ctcccaggtc gaaacgattc tcctgcctca   36000
gcctcctgag tagctgagat tacaggggct tcccaccacg cacagctaat ttttgtattt   36060
ttagtagaga tgaggtttca ccctgttagc caggctggtc tcgaactcct gacctcaagt   36120
gatccacccg ctttggcctc ccaaagtgct gggattacaa tgtgagccac tgtgcatggc   36180
cttatataaa ccttaggtaa ttttatacaa tattttaaat aattttgtg catgaaacag    36240 agttttgact gcattttgac tgtgactcct cacttgaggt caggtgtaga cttttccact   36300
tgtggtgtca aatttcagat tttgaagctt tatataatga gatagggtct tgctctgttg   36360
cccaggctga agtacggtgg cacaatcaca gctcactgca accatgacct cctgggctca   36420
agtgatcctc ccatctcagc cacctgagta gctgggacta caggcatgca ctgtgactgg   36480 atttttttttt tttttttttt tttgagacg gagtctggaa tctcaagtct cgctctggtg   36540
cccaggctgg agtgcaagtg gcgcgttctt ggctcactgc aatctccgcc tcctgggttc   36600
aagtgattct cctgtctcag cctcctgagt agctgggatt ataggcgtgt gccaccactg   36660
ctggctaatt tttgtagttt tagtagggtc ggagtttcac tgtgttggcc aggttggtct   36720
```

```
tgaactcctg aactgaagtg atctgcccac cttggcctcc cagagtgatg ggattatagg    36780
catgagccac cgtgcccagc cttggctaat tttttatatt ttttgtagag acagggtttc    36840
gctatgttgc ccaggttggt cttgaattcc tggactcaag caatctgccc accttggcct    36900
cgcaaagtgc tgggattaca ggtgtgagtc accgctcctg gcctgaagca ttttggattt    36960
ttgggttaga gttgcacagc ctttactgtt attatcctga tgttattatc cacattttac    37020
aggcaaggat ctggaggcgt agagaggtaa aatcattttt tcaaagcccc agaagtacta    37080
agccgcagat tctgaatttg aactcaggca ttctgggtca gaattagtga ggttttaagt    37140
taattttttt ttttttttta gatagagtct tgctctgtta cccagggtgg agtgacagtg    37200
gtgctatctc ggctcactgc aacctctgcc tcccgggttc aagtgattct cctgcctcag    37260
cttctagagt agctgggact acagacatgt gccaccacgc ctggctaatt tttgtatttt    37320
tattagagat ggtgtttcgc cacgttggcc aggctggtct tgaactcctg acctcaggtg    37380
atctaaccac ctcggcctcc agaagtgctg ggattacagg cgtgagccac tgcgcctggc    37440
ctaccccctg tcgcccaggc tggagtgcaa gtggcacagt ctcggctcac tgcaacctct    37500
gcctcccagg ttcaagcgat tctcctgcct cagcctcctg agtagctggg attacagata    37560
cccaccacca tgcctggcta atttttttttt tttaagtatt tttagtagag acagagtttc    37620
aacaagttgg tcaggctcct cttgaacttc tgacctcatg atctgcctgc ctcggcctcc    37680
caaagtgctg ggattacagg catgagccac catgcctggc ctaagtttgg ttttttaacca    37740 tgctgctttt tctagaccct tctgtcagcc agctccacaa tggtgaatca gggagttagg    37800
tccgtctgta agagagggcc caggagctgg gtcagatagg taaagagaca ttccttagtt    37860
cttatcctct gctaccaagc catttcttgg gatcaagccc tctttggcct gtgtcattcc    37920
acctccatta agttcagcct tctttccttc tttccacatc tttccactgc tgttgaaaac    37980
ttgagacctg aaatcccatc tcctgaattc ctgggagctc tagaagtgga gatgccagg    38040 ttctgtggtc agagctggtt gggattacaa ataaaccaaa gcctgggaaa ctttcttgct    38100
attaatagcg cagacctttt ggggagggaa tacccaaact cgatgctgtt ggaattgatt    38160
ttgcctgtct agatgacata ctaatgagct aagtggttag cttcggatca ttattgctct    38220
ttcccaagcc aagttctttt aaagactaaa accacaaaag cagagaacga gttgggttag    38280
agaggcatag tggctgggtc cagagaaggg agagtggtca gccctggcct taaacatgag    38340
aaaataaagg tggtccttgc tttggaatga gttagtggtg ctgactaatt caactggttt    38400 ttcttttttct ttttggaagt ggaatttgat ttggtgtctg gattttgata gggccattta    38460
tatttcttca gcactttttg gttcttgcag aaagttacat tcctagttcc tcaactgctt    38520 atttctttt ggttttgaa gcaggaattt gatttggtgt ctgggttttg ataggggtgt    38580
ttatgtttca tcaatgtctt ttggttcttt cagcgtttct ctccttgtct gtcatgtgtc    38640
agagagggtg cctgtcaacg attctctctc tccagggaga aagtctttct taaaacagcc    38700
ctaagatcct tatctcctca aatcacccac tttgatgata atatccattg ttctcttctc    38760
tgcttcttgg catattctag tcagtctatg tatacaatta aaaaaacaaa acagccctct    38820
gtgtccaaag tgcttggaat atcccagtgt ttcacaggag actttggaag tggacaaaac    38880
tgtatttcct tccccaaatg aggttattgt gctcgaaata tctcctggta gtttattaaa    38940
ggaaaccgca ggcaggggta agagaggcag tttctacagc ctgcaaccct attatcttgc    39000
ctcttctttt cgaccctcct tcctccctct cctcttctct cccccccctca ccctattcaa    39060
```

```
cccagcccca catgtcatgc cgtccccagg aggtagccct gcagccctgc ttctctggga    39120
tggtctgttc ttgccacccg tcccatggaa cgtgaagaag gaatttgggg tgtggacttc    39180
cttgagtgac taggattaga cccgtcgggt ctgcagtcag acgagaagcg tgtgggcaaa    39240
gggaactatt gtgtgaggct tctctggaca gaaagcctgc cttcatcttt tactgtgcct    39300
aatggacaat tgagacattc agcttatgtc tgaaaggaaa gtgggccggg atggtctagc    39360
agacctccca gatgaaggct tgtaggagga gcaaatagag acaaggatta ccaacagggg    39420
gaacaactgg ggcagagtcc tgggagagaa tgtttatttc cttgctctct aggagggatt    39480
tggaaagagc cataatcctg ggttaggagt aatttgttac agcaagatga tacttgagtg    39540
acaggctgct tctggctgag gcagcaagac ttgcatgcag ggggtcgtg gggcctccag     39600 aaggtcagcc tcccgtaaat cttcaccctg gctttggggt tgttcctcc ccaagcaaaa     39660 ttaaccagag gcactgctga cctttgggct tcctgggtgt agcgttacga agcatctcca    39720
catgtttgtc acagctagaa tttgacaata aaaatttgga cagggagacc ctgccagagc    39780
cactgacctc tttccaatgt gacaagggga aaaaaacaa aaggaaaacg cagcacgggg     39840
tgcggtttca gttgaagttg gaggacacgg agcccagcct gtctcgcatt tgctgtctat    39900
gtagactcac taaagcaagt taattcattg ctctttgacc gccaagtctt tcgttgtctt    39960
ttgttgttgt ggaatggggg aaagaaatac agaatgggga ggagaaccta attagaaaaa    40020
tcaagccttg agagctccca gccatggaga agaaaggga tttttttagaa gttgtgatt     40080 taatatctgc tgcaatctga tgattcatgg atttaaaata acccttccag gtcaccagga    40140
ccctgttact tgctggcttt gtacctctca aaggtcattt gttggcttcg tctcttaaca    40200
atttccatgg tagacctaaa atttctggct gtgaaatccc ctgtgtagtg ggaagaagaa    40260
atagcaaatc ttagctgcct tggacctgat ataattattt gtcttcattt acatggttta    40320
tccttcaagg ttgaataaat gatgtgggag ctagtcaagg ggctttaggt atgtgatttc    40380
atgcctactt ttttttaggt agagaaactg aggtcacagg gtactagaga atggactcta    40440
agattcaggt ttctgaattg cctgtggttt tgttgactca actgctcttc tgttgttttt    40500
tagccacatg ccttgaaaca gtcctctttc ccatgtttct tcatcagcac cattaaccca    40560
aggtatactg tcctctctta tctttcacaa ggtcttggag ttcccatgcc tttgtaagca    40620 tccctcccg agattcagca ccaaccaaaa tcacatttgg aaaaattgct tgtttcccaa     40680
gaagctttgg aggatatgat tttgtataga acgggttcac aggttttctg ttcattcttc    40740
tatggtggag tgtgtgtgta tgtgactctg tcttctctcc attcctcttt tttttttttt    40800 tttttgaga tggaatttcg cttttgtggc ccaggcttga gtgcaatggc gtgatctcgg     40860
ctcactgcaa cctccacctc ctgggttcaa gcgattctcc tgtctcagcc tcgcaagtag    40920
ctaggattac aggcatgcgc caccacgtcc agctaatttt tgtattttta gtagagatgg    40980
agtttcatca ctttggtcag tctggtcaca caaactcctg acctcaggtg atccaaccgc    41040
ctcggcctcc caaagtgctg ggattacagg tgtgagccac cgcgccaagc ctccccatcc    41100
ccttttatct cttaaatgaa tgtggtcacc atcaaagatg gtgcctgact cttttttgtt    41160
ttcagttcat cttaaattca catataattc acacgtcata aaatgtaccc atttaaggtg    41220
tacagttcag tggttttta gtctatttag tatatttaca agattgtaca aacataccag     41280
tatcttaata ttttatcat ccccaaaaga aacactgtaa ccctagcagc cagtctctac     41340
ccgccttccc catagctcct ggcaatcact aatttacttc ctgtctctat gaatttgcct    41400
attttggtta tttcatataa aaagaatcat acaccatgaa actttcttca tctgccttga    41460
```

```
agttagcata ttttcaaggg ctaccatgtt gtggcatgtg tcagtactcc atttgttttt   41520
attactgaat agtattccat tttatggctg taccgcattt tagttatcca gctatcggtt   41580
gagacttggt gcattcttat cccagaacat accatattca gctcccagtg acacccacat   41640
tcattcctgg gctgctcctt gtcttccagc tattttcctg gtctcctgtt gcctctgcct   41700
acttcagcat gctgtagaga catgggtagt aactaaaaca ttccaattaa ctgcattgta   41760
cttggccttt ttataagaag cagtaattag aaaatatggt ggccacaaga ttgatattaa   41820
agtgaaagat tgtaaatact tttctgcctg aaggtagatg gcctctggcc tgcctcttag   41880
tgggaggttc ttccaggagc ttgcaagcat ccattatttg ttagtcatca gcttagcggc   41940
caaggagcat tagcctgtct tgctctgtct gctgaagact ctgagagaca tgggagggca   42000
agggctgctc cttttgaatt cttccaatgt cttcatgtcc tttaacctcc tggcttaggg   42060
acttgtgtgc tggtggtgga gctgacattt gtttggaatc cacagccctt tgggtgggac   42120
tcaatcttgg ggttgcctga agactttgag atggctaggt ctgggcctct tttggtcact   42180
atggaacaag actgtctcag aggccagagt ctgtctcacc agctccctgt cttgggactg   42240
caccattgca gggtctttgc cctcccctgg agatttctct tcctgcctgg gcacccattg   42300
gccattctgc ccgtaagctc agtagggtgt aggcaaaaga gttctggcct ggaagtacca   42360
aagtcctgcg ttctggtttc agtccctcat aactgtgtat aactaagtca cttagttttc   42420
tgtgcctcac tttcttctgt tttaagatgg atttggagat tattggcttt gaccacctaa   42480
aaaggatgta gtgacaatca atttagaggt ctaaagagc ctttgaggaa gtaaaatgga   42540
atcttcaaat ggactacatg ctgattattg acactgccct agcactgata gttgatgttg   42600
actgatggtc agaattgctt ggcaagttgg aaaaagtac gtacagatcc tgggccacta   42660
ccaagtttca tttaacagat ctggagtgca tcaggaaaaa agtccctcta aacaagccag   42720
caaggtttgg atactgtgca accttttttt tttttttttt ttccttttga gatggagtct   42780
ggctctgttg cccaagctgg agtgcagttg cacaatcttg gctcactata acctctgcct   42840
cccaggttca gcaattctc ctgctttagc ctcccgagta gctggcataa caggcgcctg   42900
ccaccacacc cagctaattt ttatattttt tggagagatg gggtctcacc atgttggcca   42960
ggctggtctc gaactactga cctcaaagtg atccgcccac ctctgcctct taaagtgctg   43020
ggattacagg catgagccac tgtgtctggc cctacttacc ttctttgtgt taattcctgc   43080
accattgatt agcttattgt cccattgact gtgtctttag atgacttctc tgggcctcag   43140
aatatctagt ccatagctga cacagagcat ctgtttaatg gtaaatgctg caggaatcca   43200
tgcattggag tagaaagagt tttagatcat gttcctcatt tcttgctaca gacttaggca   43260
aagcgtggag aagaggttgt ccaatgaaga aatgaagtga catgccaggt cagtggcaga   43320
gctaggcctg gaaaataggt ttccagactc ttcccttct accatacttt tcctgggagt   43380
acgcactcgt aatttgaaga gcgacttttg ggagagggtg gaaggaaggc ctgggcctca   43440
gcctaagggg cccattggtt gtgagaggag ggtctggtga aattccatac cgattgtccg   43500
tgtgtgagct gctgtaccat agcctccctg cagaaccact aacctgtcaa atgcagaaat   43560
agttcaggga cagagctgtt aaaggattgg cgggttaaag aaaacagtga atcccaagtt   43620
ttgttaattg gatttttttg tttgttagtt atttgttttg cttcattgtc ttcatcacac   43680
caggggcctc cttaaatctg gtggaaaaat tccttggaa aacaattcag tgtttgtcca   43740
tagacttggg agggagagat gctagatgct ggaaagtctt gcttattact ttggggacac   43800
```

```
tgagatgttc ccttcaccat gtactttgag acacacatcc tggttgagtt caggcaagga    43860
tgcctaacag ttgataagaa aactgggaaa gatagaaggg atttgtaagg taagtcaggg    43920
tgagtgaaaa cacatccggt atgctggaga cctagatgct tgactgccac tcgctcctgt    43980
cacctcagtc aatctgggtc ttgctctgtt ggccttagtt tcctccttgc taacaggtta    44040
gttccacctt tctgcccatt tattttgtag ggttattgtg gatgtcattc tgaactctaa    44100 aatacctct aaatatgaag tgatattagt gctctttaca ttgttatgat taaaaatatt     44160
tatgagaaaa aggttaactg taaggatttc attgaaaatc ttataacaac caactgatag    44220
agatagaaga taaggctatt aaattgttca cacagatgcc ttgatatcct acctttttcc    44280
ccctatattc cttttatgtg agaaatgaga tagtgattta agggaaaaac ttaaagagt     44340 tccgactatg ttggtttttt ttccccaag tcaaccttaa tatcttactt aaatcttttt    44400
cttttttatc ttttctttc ttttttcttt ttccctccct ccctcctttc ctcctcctcc    44460
ttcccttcct cctcctcctt ctgctgcttc tctctctctc tctcgtttcc ttttcttttc    44520
tattcttcct ttttcttttg agaccaggtc ttgctctgtt gctcaggctg gagtgcagtg    44580
gcaccttctt ggcttattgc aacctctgcc tcctgggctc aagtgatcct cccacctcag    44640
cctcccaagt agctgggacc acaggcacgc gccaccacac tcagctaatt tttttttttt    44700
ggtagagatg gggtctccta ggctggtctt gaactcctgg actcaagcaa tcttcctgcc    44760
tcagccttcc aaagtactgg gattactggc gtgggccacc atgcctggct gaaatttttt    44820
ctatggcttt attctttctc caagtacaga gtctacccaa ccttctgaga tctttggttt    44880
tcttttccta ggtaactata gtacatactt atttatgtta aacaacagca atcacacatt    44940
tcttttctta tacagtcatg ctttataggc aaataaagcc tccgtcttag gctttctgga    45000 tttttcaaa agatgcaatt cctggagtat gttttttactt agagcaaagc agcctagtct    45060 cctataccti ctgcatctgc agaaaagttg gttaaacaga ctttgtaatg atgcccctta    45120
caattctgaa gggacttgtg aaatagtttc acagagtttc agtgttaggt atatttgatc    45180
aatgctaact tttggaaaac tttggtgcct gtatgattca gagggtaggg cagaatatta    45240
aattaatcac aacttcttgt attttaacca ttctgggtaa attgggattc cgtgacgccc    45300
aggcaaaatt atttgtttat agaagatggg ctgaattttc catcgtccat ttctgagaaa    45360
tgaggtaggt ttagaaagag acaatcaggc ctcttcttta acagaaatgt ttgtgtctac    45420
taggtgtgtg tcacaatatg agttcctgaa gaaataagtg tccgctattg ggttgtatac    45480
ttgtacttcc tattttctta ttttgcacat ttttctggta tttcccttc tatggtgagt     45540 ggcttctgat cgtctttcct tttgtaaagt gtaatgatat gagaatcata atcgtggtgc    45600
ggtcttttgt gttgcatatt tgtaggggggt cagtatgaat ggcccgtggt gaggctgcac    45660
tgaaagatta ggagcagcca ccttgatgcg gaggaggctt agtgactttg gacatgatgg    45720
gctatggctg gctatactct cagctttggg cgcataagca gagtattgat tttgtatttg    45780
gttaaaacca gaagtacaac tttctggcac cagaggatta ggaaaattta acagcggaaa    45840
gccatcatga ggatagtaac caattaattc gattttttttg gtcagacatg gctcccacct    45900
gtaatcccag cactttggga ggctgaggtg ggagggtcat ctgaggtcag gagtttgaga    45960
ccagcctgac caacatggta aaacccgatc tctactaaaa atacaaaaat tagcctggcg    46020
tggtgatacg cgcctgtaat cccagctact cgggaggctg aggcaggaga atcacttgaa    46080
gctggaaggt agaggttgca gtgagtcgag cttgcgtcac tgcactccag cctaggcaac    46140
agagtaagac tgtatctcaa aaataccata attcgttttg tcttttcttt actttttct    46200
```

-continued

```
ttccttttcc ttccctctc ccctcccctc cttcccttc ctccccttc cttcccttc   46260
catctcttc cttccttct tttctctctt tctctcttc tttcaacagg gtctcgctct   46320
gaaccttc cagtcagaat tgctcaggga ttttagact tccattctgg aaaagagggg   46380
gtagttattt tggtgagatt gtggtcttgt ggttagacct tgtgatgggg gcctcagcca   46440
aagggttcag gattttttc caagcttc cctcacaact tgagttaatc cgaaacgttg   46500
ctattaggcc accggacatg cttttctgca tgcctgtgtt gggctgttg gattgaaggc   46560
ccagcaaggg aaggcaccct cgcccatctg acacaggcag gcctctacaa ttttattccc   46620
taaccagggc atgacaaact atggcccata gaccaaaatt ggcttgccac gtgcttttt   46680
ctggccagtg agttaagaat gacttttat tatcattatt attaatattt tttgagccag   46740
gttctcattt tgtcacccag gctggagtgc agtggtgcaa tcacggctcc tgcagcgtga   46800
aactcctggg ctctagcaat cctcctgcta acttttta tttttgtaca gtcttgctgt   46860
tgttgcccag gctggtctgg aactcctggc cttaagcaat cttccggcct tggccttcca   46920
aaatgttggg actacaggcc tgagccgctg catccagcac ttttattatt tttaaatggt   46980
tgaaacacat caagagagga ataatatttt ctgacacagg aaaatgatat gaaattcaca   47040
tttcagtatc tgtaaataag cttttattgg agcacagcca tgatacaaga catatactga   47100
ctgcctgtgg ctgctttcga gttacaatgg ctgagtcgag tagttatgac agagattgtg   47160
tgggccgcaa agcctaagat atttgctgtc tggcactttg cagaaaaagt ttgccaaccc   47220
tgccctgaac aaataaaggg acaaattcca cttgccccgt ccatctgtgg agcagagtca   47280
ctgaaaggaa atactggaaa tactggaagc cacttggtgt tttatcaagg atgtgaggtt   47340
tcctggcaac tttgtcgcca tatcatcatc atcatcacca tcatcatcat catcatcatc   47400
atcatcatca tcatcatcat catcatctgc cctttaagtt ttctgcttgt ttagaaaaga   47460
aattataca gagcccccag tagcagctgt aaggggcag gttcttggag cagcccatcc   47520
tcaacattct tgctgctgat ggaagattct caaggatgaa ggcccctcta tgggagcagg   47580
atcagtctgg ctttagtaga tgccaatttc tgctaagact attcctaaa ggagcctctc   47640
ctcattgcc ttttctccct gttttcattg ggggaggtgg aagaggagaa aataattag   47700
agatgctcac ctttttcttt tgctggcaa tttaacagtc ttttcagctg ctttgattcc   47760
ttcaggcca ttggtgttgt atatatttca agatttgctc acaggtccaa agcttaactt   47820
aagctccctg agacatatca taaaatatga tttggggaaa aaccctaatg ggccatgatc   47880
agaacattat tattcaacaa aggatgaaat gcttaagcca agatggcctt cttctttct   47940
ttctttcttt cttttttt aatgaaagtt gagcagactc ccgtccaaca gttttcaatg   48000
taggaattcc cacagcccca tttgattgca gtttgttgaa aagtttaatg tttttgtagg   48060
caattcataa tttccacatt gaacagcctg agaggaagag agctggagcc cactgttgtt   48120
tttgtagtgg gatggtggga actttttttt tccctcccc aaaaggatat aaaactaagt   48180
cagatggttg ggaaaacgtg gcacagggtt ccagcccttt tgtaaatctg agatgccccc   48240
tcctttaggt cttcctttag gacccaacag aatagaaatt cctgctgctt aatgtctcca   48300
ggaaggaaaa aaattttcct ctaggctgta atagtaccta atttccttt tcttctcttt   48360
atttatttat tttccctatt aataagcacc aattgtagaa gatgaaggaa gctgggaaac   48420
ccatcacttt tggagaaggt taatagcttc ctttagaaaa tcctgacata atacttattt   48480
ccccaaaagg cacttcatca gcctgaatgc cagttaagat tcaaggaatg ggcttggatt   48540
```

```
tgtgtgtacc cagcggttct gtggcatcaa gttgcactgg aaggagagt ttggggctgt    48600 cactgtggag tccctgcaag tcagcaggac cagggctgtc ttcctgcacc atctggattt    48660
ggttagctct ctctgggcag tggggccgag tctcatttcc tccaacaata atgttatata    48720
ggcaatgatc ctgggctgcc ctaacataat tgaaaattat gtgtattgta ggcttggagt    48780
gctgaaatgt gggctcataa aaatatgtgg tgcaggtagc ctatggagat tggatgtggc    48840
acacaatgaa gcttttatgt aaagtaagaa ttataagtct ccatgttaat attgtattat    48900
gagtatgaca gttcttgggt gggtcctcag ggcaggtctg tcaccttcaa caaagcccga    48960
gtttcctaat tctacagagc tggtatttgg atgtaatcaa atcggttttg caggtggcca    49020
aagatgaaaa cttgtccacc aatccagctc tccccactga gggatagcat gggatgtaga    49080
tgggtttgac tccatttggc attttgttc acgggttttt atgagatgga gaggtgagtg    49140
ttggtgggtg tccatttttgg ttggcctcaa ggaaatgact ctattgagtg gttttgacca    49200
atgcagctca tatagttatg tggtaagtga aatgggaag aagttgggat gagatggggc    49260
agtttagatt cccagagccc tctggcctgg gttacagatg gagactggaa atatttactt    49320
tagtggttct caacttgaga tgatactgct cccagagaag gtatttggaa gtgatgagat    49380
ggtaaggata accaagggg ttcctgttgg tatttactgt ctgggggctt ggagtcctac    49440
aagtccttca gtgtttgggg cagactcccc acctaatacc ctgtcgcaga taggacaact    49500
cattcagtac acagatgaaa aaaacagaga tcactgaagc aaggggagtc gatgcagggt    49560
cttgtggcaa gatgcagaca caaccggact aataactagg ttgctcacca cgggaggcct    49620
ctaggtgaaa gctctgaatt tgtagcagac acacccacct cgtatagatc ctagacgtca    49680
tgggaaaatc gactgtgtac tttggcaagt agttcttggg caatgatctt ccagcttag    49740 gtataaccaa atttggtttg aatttgccaa gcagtcgtat cttcgaggaa ctccgtcggc    49800
tggcttgtgg atggctttgg cacttctgtc tctcgtggga tttgtgcaaa cccttctttc    49860
tgtattatcc tttcctgtct ttttttcttc tattgaaatt gttctgacca tcaagaccta    49920
actctgtgca gccttcccca gtctattgtc ccagaaattc tgtcatcttt cttggcattt    49980
cctgagtccc tgagtctctg tcacagtgtc accatgttct gtcttgattt acctgtgtct    50040
gtaaggctcc tcatgctggc aaaactcccc gagagcggac atctttgtct ctcctagtgc    50100
ttgtcacagc ctgtacacaa agcaagtagt actcagtgtt cattgagtaa agttttctat    50160
agaattaata ttaaaaccag ccatttattt tgcttgagga ggtctccgaa atgaccaagg    50220
tgtctcctta tatcttatat cccctccaag cattcattaa ctgatggatt agtgagttgg    50280
ccttgagaag cataaaggct cgtctccatg tgcttctaag cattgtgtct aagttctgtt    50340
tggtttcctg agtgaaactg tcttaatgtt accaacagaa gttaaatgcc taagagtttc    50400
ttatacatgg gctgagtacc tctgtgactg ggcaagccac ctcacctcat tttaccttgt    50460
ctgcaaaatg aggaactggg tcaactcatc gttcaaatct cactgaaagc taattgatcg    50520
cttttgacag aagtagctcc cttgggccgt atatttattt cctagcttgg aggaaggtgg    50580
ggacagacag aattgatgta caccttattt tttatctcta tggtaaacct gtgcatacta    50640
aagcattcct ctggtctttt gagatgagtg tatacattgt gtctggccct gtgcattttt    50700
taccaagaag taagttttgt tgagtaaact tgggttgtat gaagaactgc atgctcaccg    50760
tactcaagta gcttttgcta cctaaaggac agctgctcat atgtacttga cttccttaa    50820 agtgaaggat gatgacattt gaaaacgga ggttgaaaag gagcagattt ggaattgatg    50880
gtttcctagg acacttctgg cttgagattt gtgttttact ttcttccttt ggaatagctc    50940
```

```
tatattctttt cctctccctc cccacctctc ccactcccct ccagccccca ccaagttaag   51000
gtagtagtaa tgaaatcatt ttttctgaag ctaccctgta ctttgaatgc aaagacaaaa   51060
aatacagttg ctagtaacat taatcttcta tatgtgtact tactgaactt gagctctgag   51120
gaagacccta ttggaattgc atgctttttt attttttaa tgattatttg catgcttgta    51180
tgtttttcag tttctgaccc atgtcacagt tatttcttgg gctagttgtt ctgcatttac   51240
tttctgaatt cattgttttt catttcactt ttgtttcctc tcgccagtat ctccagatga   51300
aatggccact gcttgatgtc caggcaggga gcctccagag tagacaagcc ctcaaggatg   51360
cccggtcccc atcaccggca cacattgtcg taagtaacct cccagagatg atggcttcct   51420
ttattgaggg ggtgaaaaag aaaatgcttt tttgatgata acaggcctta tttgtcattt   51480
ttttctttct ttaaacacat tttctttgga aatattgttg ggtatagttt atatctataa   51540
ggtattcatt ttctgctatt ggaccttaat gattgtaacc tacctggaaa ttttacaaac   51600
ctttcctcca ctcttttcca tgtatttggt taaaatctag ccttgtgggc tctagtttat   51660
aggacacaat caccatggta tggaggagac tagaggtggt atcaaagcag ttataaaaat   51720
acattcaggg caggtgaagt gaagaagagg gaattagaaa actcaaaagg gggtcctgga   51780
tttgaaactt gcctattatc ctctccccca atttatctta atatttgttg gcaacattct   51840
acactaacat tagaaaaatt tcatctgggc tggctgactt gtaaacctag agtagaaatg   51900
aactttgaaa ggctaaaatg gaatttaatc tatacatcca tggctttgaa agtatgtagg   51960
tttgatagag aaagcatttg ttttttagtac taagagacta caagtgtgtg tctacatata   52020
tttttaatgt atttcttag ggttttgtag gctctaagag tggaatttat aaattaacct   52080
cttgagaaga tagctcagcc ttatttgaag attcccttct atgtatttat atcatgagct   52140
ggacttcata cttttgaaat aattaatgga aggcatattt ttataatgaa tccatccatg   52200
acaggtagaa ttatgcaaag catgaatcaa tcatgggttt ttcatttgag tatcacaaaa   52260
tgttaatcat aaatacattt tgcctctata ttgtaatttc taaaaattgc aaaataagtt   52320
tcttaagtag aaaaatctta agatgcattc tgccattttg ggctaactgc ctccttattt   52380
tggagcttgc tgtaattgag catgtgttat ttaatgagtt atacctctgt catatgtgtg   52440
tgtttatatc acaaaataac ttattttat aaaccatat tttgagtcat catttgtgac    52500
aatgtcttct tttctctggt ataaatgagg catgtagaaa gaagattgac atttgctaga   52560
agcttcccct ttcctctaac tccacaataa aatggatgct cataattaca tctgctccta   52620
taaggtcaag atttcagggc tggaagtgac cttagatcat ttaggcccaa cttgccctca   52680
ggaaaggaaa ctgaggccca gagatgcctt aagtgaattg cccaatgtca cacgctgagt   52740
cagtggccag agcaaggctt ggatccagtt ctctgctccc tttccagagc cttgtgatgt   52800
cttctctcct acaggaggtg aaaataactg ctgtggctgg ttctgttttg ctgactgtaa   52860
attgggtcat ggtcagggac agtgcatagg tgtaaagaag ttgctggttg ggggttctaa   52920
tgcaggtttc tccaaaagtg aatgccctgt taaaaaaaa ttcttaacaa atatacagag   52980
attttttttt taaaaagtg tgacagttct agacacctag agagtaaagt gaagaagcct   53040
gttttcaggt ttcccgcctc cctgaatttc ccagcatggt ccaggctttg aaatttattt   53100
atctgctttt ggcaatggtt gatgggaatt tcccacattt attttttagc tacagagaaa   53160
ggacattatc tttaaaatct cttcgttgtt ctctctcttt gagtgaggag agaagatgtg   53220
aatcctggca gtggttcaga gtggacacag cccctgtgtt tgtggcatag gctctgtggg   53280
```

```
ccccatgcca gggagcagta cccccgtgta aaggagtggg ggtttgtcca tttggataga    53340
gcaaagatcc tccacctcaa atcccacaag aacagttgcc acaacctggg ccctaagcat    53400
ctcattttcc tatgtagaaa ttaatgatct ggaggagatg gcaaaacatt ccttccagag    53460
cctgtgtgga ttttggccag gggtgcagca aggggggctta ggcacctttt tcctctgctg    53520
tgtcttagca ggcgtgttga ccatagcaac tcccctgggg catacacacc ctcttgtaga    53580
tggagacctt tgtccaaagc agccacagct ggcaactgtc tacaatcttt tgggcttttct   53640
gctgtgctca aggggatctg ggaatggcca ttgcctagag gggatgggct ggtggaggaa    53700
ggtgggctct gggagccggg gagaagggaa aagccatgaa tttggacaaa aggacaaatg    53760
tggtttacat ttgtgaaata cttgaatgct tgtcatgaat ggtgactttg gttctatgag    53820
tcagccctgt gatggggtat ttctgcagtc ttcacctgac accaggggtg agaaggagga    53880
tttctgggga ggaggaaaga gttgagggag ataggaaagt agagtggaag aaaggccttg    53940
cgttgttgac ctctatccac ctggtcacct atagttttg ggattgagga tgcatacacc     54000
ttgagactac aaatttatga ttatattttt gctgaacata aggcaatgtg ccaaccaaaa    54060
ccagctgttc tttggctggt acagtgtgtc tttgtttgta aagggtgcat tctgaatggt    54120
ggctgataca tcatttgggt ctttgtacag ttaaacattg ccagagggt ctggttcgtg     54180
tttagagtcg ccgatgaagg gctaactttt ctccagacac ttgggctctct tgttcacact   54240
ttgcttttca ctcttttaag taagacatag tcacatcaca gtgtttcatc agacatgttt    54300
caaaataatt gtctaaggat tgcttcttaa tttccccgaa atttggaatt gttgtaactt    54360
ttgggccaag ctatttcata attatttcta atgtctcgct tgaagaatag ggatgtattc    54420
agtgttgatt attaatcatt cgaaactaca actttacaga ttgctaagaa gaataacttc    54480
ttccagtacc catatggggc agaatcttca cgtgggaatt cagagcattt tgttggacta    54540
ttttaatctg attggattat tttcatgtgg tatgtgggtt accacattag aaacgattga    54600
tgtgtagaat aaatgttctt aacaagtgga ggtcaactta tcaaatgata tttacattaa    54660
gaatagactc cacaaatttt agttcctgta gctgatatag catctcattt gttatataat    54720
ccagtgattc ctaatctgtg ttcagaggag agaggaaatc gattgcaaca gggacgatgc    54780
cttcattggc tggcccaaaa ctgggagttt atacaaggcg tcagtctttg ccttcctcct    54840
ccctgccttc cctcttcctt cttccttccc catactcccc aacaaattca tggacttctt   54900
aacaactcag agacattagc cacaagttcc aagacacccc cacccccag cctccccagt     54960
cctattttcg cattcatata actaaactct ttttctttct tggtggagtt ttgaaattta    55020
tattttaat tctttgctcc cttttttcct cttacaaaat gagtgccaag cagctaagtt     55080
gtgctgagtg gtagagtttg agtcagtctt ggctggtaag ctgtgggggtt aggagccgct   55140
ccctggatac cacctctggt gtctttgcta tacaaagact ttcatttagc ctcctttgta    55200
tccagcaaaa aaagattcag tacccaaaat ggtggtattt tggtatagta tgtatcttac    55260
aaaacggcaa aagacttcaa aagttcctac aattttatct tgggggtttc cttttgaagt    55320
cgatgtagaa ttttaccttg gggtggattt tttgtacttc ttggtctggt gtgttttgtt    55380
gtgtaatgag catggaggtg tgggataaga aagcagactg aatcccgagg aacaaagcct    55440
gccagactgt ggtggtgtac ttttcttgtt gttattgctt aaatgctgca agagagtgga    55500
aaactcttac gaaataatgc acgatgggta gaacttcaga gaaaatctct gccgtctacc    55560
ctgtgcattt tcgaggaagc tcagagggca tgctgaacct ttgcttttttg tttctgaaga   55620
gttcagggga acctacccat aattaatttt ttaaaacact acctagagag cacccctcttg   55680
```

-continued

| | |
|---|---|
| gttattaaac acatgcgctg tttcgatggg atgtttgacc tggattgtgg atgcttgctg | 55740 |
| ggacgtggca tgtgttggga ggctctgtgc tgcctgctga gcaccagcaa agccacagtg | 55800 |
| gcccctacct ctgtgggagg ccctgtgcca ggtgccctca aagagtaggg ggcccatgag | 55860 |
| ggtatgacca gggggaccctg atttcggctg agaagttggc ggggattaca ggcctgggcg | 55920 |
| gctccctgag gaaattgcat taaaaatgag atctgaaggc ttgattgggg ttggcccaat | 55980 |
| gaagggatag gagaagggat ggggagtggg cagaaggaaa cacatgtgtg aaggtcctca | 56040 |
| agggaaaagt gcttggcttg gacagaggca ggaaatcagg taggaggcta gaggtcgggc | 56100 |
| agggctccgg gagagtgact tggggtgcag catatggtga ggatctgaca ctggggagtc | 56160 |
| atttgagcag gttggctgtt tctgtaggag cgtgtgttaa gctgctggca gtggggatgg | 56220 |
| tgaaaataga gatgtggagg aaacagcagc ggaacttgct gacaggttag atattggcat | 56280 |
| tgagggagaa aggagagtca aaggtaggta gatggagatg cttcactgag tggggagtat | 56340 |
| tggaggagga gcaggtttgg ggtggaagcg ttgtcctttt agagagattg tatttgccat | 56400 |
| tgattgattc attcattgtt tctgcaaata tttagtgtgg gaaaaagcat gctagacacc | 56460 |
| aagagagagt ggagtcaatg aagaacgata acagcaacaa agactgtagc gcttcctatg | 56520 |
| cgaggcttgt tccagttgct tcagaggctg tgttacccct gttctagaga ggaggaacta | 56580 |
| ggcccaggga ggtggggatt tgcccagtcg tgggagtcag gatgtgaaac aaggcaccct | 56640 |
| ggctccagag cacaccgtcc tctcaaccac tgcagagaag ctgggaaaga gacaaataag | 56700 |
| tgggtgctta gagcacaatg tgtgtggtgt gccaagagca gctgggagcc ctgggacccc | 56760 |
| cagggaaccc cagccccacc tgggcatggt gggcatggct ggaggaggcc tgctggcttt | 56820 |
| gctgagagt gggacatgca tcaaggtggc cagagactgg gcttctgggt gtcgtgctgt | 56880 |
| gactgctgca aagggctcat tgacatatgg tggggagggc cagcgtattt tctgcgggca | 56940 |
| ggacatttgg gggatatggg gtgtgaccct gtactatcta aaatcttta cttctggatt | 57000 |
| atctccactt tctctactgc atatatactt tgtttttatt tattttattc atttatctat | 57060 |
| gactcagcca gactctctaa aagagttgac ttgtgtttcc tagcagccac tgagtcagaa | 57120 |
| cttcccatt tcgcagtcag ggctgtggtc agggtgtctg tgttgtctaa ggatataaag | 57180 |
| caagccttcg ggcactacca aaacattatt ttataaggag aactatgagt acctaatagg | 57240 |
| aagaaccagg caatcaggtt atcttttggt gaggaagaag tggtagatgg gatcattggt | 57300 |
| gctttgaagg gagtgggtgg tgtagactcc aaagtgtaca tggggccatg atagagtcta | 57360 |
| tgtcagatgt ccaaagcttc cttctctcct cccagaaact ctgtcctctg gtgaagagtt | 57420 |
| ttgaagttc ctgaggtttg ggttcatggt gtggcaggtg ataccatggc aatagaaaat | 57480 |
| atcccatcaa gaaggattgt gtgacctcag ttgtagcccc tgcatgttgg aatcacaaca | 57540 |
| atttgcaggg ccttaaaatc aaatgccatt tcaccaactg ccctcccccg ttttttcag | 57600 |
| cactgtttgg tagctatctg tttcccctga tattcttgga cacttccaga gatgggggct | 57660 |
| ctatctcctg gtggtagact gtttctttt ggtacaatat gaactcttaa gagagttcta | 57720 |
| cctttaggga gctgcagtct ctctcctgga aatgctcaac tccttaattc atgttttgct | 57780 |
| gttaaattct gctaatgcct caccttacat gtcttgacaa tttgaaggta gctattgtat | 57840 |
| tccccgcaac cccaagtctt ctcttcaaaa tgattattaa ttgtaattca aatcatcagt | 57900 |
| gactggtatc ttagactact taaggatggg aattgctaat tttgtattta aaagttgtac | 57960 |
| ctctaaagta agtgaaattt atttttaaac gtagctttct tcattcataa agtttatgtt | 58020 |

```
cattgtaggc agtttggaaa acagcccata atctcaccac tcggagatta cattgtgaat    58080
aatttggtat atttccttttt agaaatatac caaattatcc tttttttcctc tgagtgtatg    58140 aatatttata tttgttttta acatacttga gctcatagtg ctcagtattt ccaacgttct    58200
gtttatttaa gatgaaaatt gctgtagtta ataagcactt ccccatgtca ttaaaatgct    58260
taaggatttt taatgaccac ataacagtcc ataatatgat taaacccaa tttactgaat    58320 caatgccata ttgttgggtc tttagattgt ctccttttgt ttctgctact gtgaatgatc    58380
ctgtgatgat catctttgtg tgtaaatctt tgtcccctcg ccccctcccc ttttattatt    58440
ttcttgggat agaccccagg acaaaaggta gaaaagaaca aagtgttaaa aaatttcttg    58500
atacatagcc acagattatt ttcctgaaag ttctcaacat ttataactac gagcagtatg    58560
taagagagtt atggttggaa tgattttaat gtctctgggg aatttaacaa caaaaaaact    58620
ttaggcttct ttggagagag acatgcccctt aactccaccc cgccctagaa cagagaccca    58680
gcccatccaa gtcagcctcc ccaggtcctc caccttcaaa acaggcaaac gaaatcattt    58740
cttgaataat tggtaggctt caaggtcaga tgtttatttt agataattca cagcataaat    58800
ttatatgttt taggtacctt agcccctgaa tatactcagt tcatttagga ctattttaga    58860
ggtcttgagt ttactcttat aacctcacat tttttttgtga atttttagtt ctattatctt    58920
tgttttcatg gcatattatt gggcaaagat actatttatt cgatgctatg tgtgagctgg    58980
gtcaggatta tgaccctgag ttatgtttct gggaaaatgt acccacttgt caaagatgcc    59040
gttggctcct gtgattaagg tcagcccaca atgaatgtgg ggagggctgg cagcctctca    59100
aatcagctct tgaccatttc tcaagctggg gcctgttgtg cttggggaa gagtctttgg    59160 cagctcagct cggggctagc gtttcctgac atttgtttcg ctgaatgtta acaaggttac    59220
tggaaaaaag ggttctctcc taaaataggt ttagggaagc actgggatat gcgaagtgaa    59280
tgagtttctt tagggcagga tcttgactct gcagggggct tggaggcctt ccctagagtg    59340
gggcttccta acactgcaga gctcttccca ggacgagggg caagattggg acctactttg    59400
gaaggttgtt tttgtttcgg cacctgctct gtttacgaag cgtgggagcc tgttttaaat    59460
taatgtgcgc ctactagag ctacactcat ggttttgact atgtttatct ttccagtaaa    59520
taaaacaaaa ttgttcattt ggcacccagc ctgtcctgct tgtcatttct tgtcttgctg    59580
attaactcta tggatgggc atgtttctcc aaccagattg taagtttctt gaagccaagg    59640
agccctgtgg ttgatttctt cacatgtggc tctctctcct cccacaatgg tgcttcgtta    59700
attaagcaga aaacccatct ctggttaggg actggagttg atttcgtttg gaatgagtgt    59760
gacttcatca tgacctgaaa gtgttcagaa ccatcttggt tagcacaagg gcgtggacgt    59820
gtgtctactt tctacctgat gggatagcat gtttaatttg gggttatgac actgaatggt    59880
ttgccagtaa cttgctaatc caaccttata cattccagct cacagtggag cgtgtctaat    59940
tgccacagca gcatttatgt ggaacgtggt tgcacaaaag ctccagaaag tcaggctgag    60000
ggctcctatc tctcctcaat cttggtttac gatgtctgtt tctgaggaat cctgggatgg    60060
ggccactggc tctttaagag agagcccgat ttggaaatct aggacttgat tgttgattat    60120
gggcaataga tacattttaa gaatgatgtt gtaggctgta tgaagtcatt tgatgattgt    60180
tttgttaatg gcttgcaggt cagattttca tcttttttaaa ttaattatca tagaaggaga    60240
aaacaactgg atttcagaat tgtcccttga ggtgtactgg aaactaaggc gtgagggact    60300 catagggtc tggcttggaa agtgtattgc tatgtccagt ttacacataa ggatgtgcaa    60360
atccagcagg ttagctgagc tgcccaggaa tatccaggca agaatgacca tattctgata    60420
```

```
attactcagg cctctgcctc atctccgctg cccccccgcc ccctgactct cttctgagtg   60480
ccagattcag cctccatttg aatgccaaat agacaggaaa ttagcatgcc cagaatccac   60540
gtctttagtg cactctctcc ccagctccaa acctgttact gcttgtgttc aacatctcag   60600
taaagctcaa caacatcgac ccattactta ggcctcaaac cttgggtggc atcgtcgatt   60660
gctcttttct ttcataccc  acattcaacc catcagccca tcccacaggc ccaagtgtgt   60720
cctctctacc ttcaaagcgt gtgtggcatc caccgcttat caccacctct gccattacca   60780
ctggagtcca gtgccatcat ctctcacttg gatgtggcca gagtgtcttt gctggtctcc   60840
ttcttgcttc ctacctttgt aacagcctat catctatctc tggtctccat agctcactcc   60900
catactttga gagggccttt gaaagcctta gacagatcat atcacagacc tctatactga   60960
aagtcgggat aaattttatc tctggaaaga gtcccaaagc agcgatgaac agatattttg   61020
tcctgtcact tgatgaagag gtggggcttt gagacccaag agcttagaat ggagagccta   61080
gatgccacta agcccaggca ctggccatgc ttcgagtgga gcttttgtgc tggtggagga   61140
gagatggctg ggggacacct gtaggctgag caagtcccg ttcatcagac cctggctcat   61200
ccagcagggc gtggctgatg ttttcaatgt tgtatcctga gtgggaccca gatgcttccc   61260
aactgtgcca catctgagcc ctgcatgcca tctgtccagt tgcagcctga ctgcaatgtg   61320
aggctgctga agagctctgg atggtgtgaa gcaatctgtt ttctagcccg agcctgcata   61380
gctggtggat cctggaccgt gattaagtgc atcacctagg cttcaatgag atggagtcac   61440
tgtgtgtcca acagtggga taaaggcttt actctttgtc ttcctgctct gagggcacaa   61500
gctgcttgtt tctctcacaa ggacaccgtc tgtgttgctc aggtgctggg gtgaaaaaaa   61560
cagcaagcat ttgaaaaggc tgaagaagga agaaagctg agagcggtac agccttgggg   61620
actgagccat cccattgtcc cagaggtggg ggtgttatca agacctgttt ttgagccata   61680
cctctgactc ttcctggaaa gttagaccca actcaagaac acactaagag aagtgtttcc   61740
ccctagccct ttcagattga aaggagacgc caaccttgat gggtggaggt agaaaataaa   61800
gtcccaaaac agtgtcttgt aagcgaaggg gaacatggct gggcagaggg cttctggtga   61860 aactttggg agtattcagt tggaactcag gaaaaaaaaa ttgttttttt ggaaagaggt   61920 agcagcccc ttcagccaaa gctcataaat gaaggaatgt ctgagactca gaattacagt   61980
gaccaaggca agacattgtc aaaggctgaa taagtgagtt tgactgacag aggccatctc   62040
catttttagt atatggccaa gcatctttcc cacagtcttc cttgagcccc ttcccatccc   62100
acttctgaaa agcactgagt tggccattat tatgcttttt tcttaaatta tgaagttgtt   62160
ttcaggtatt gagaataaca cccaggtgct gaactcccag cataagaaat caaacattca   62220
aaatggagta aggttctgaa gctgacatct gtctctacac attttttttt ttctgataat   62280
ggcatttcct atctccaccc tcactctttt tgttgtggtg aactacactt cccttgttcc   62340
actcggttct gttgcacatg tgattaggca agggcagat atgtgatatt tattatgagt   62400
cttttccacg cagagaggat ctaaatctgg ctctttgcaa ttgccttcat acatgtgcat   62460
acacaccaca cacacacaca cacacacaca cacacacaca cacacagaca catacatatg   62520
cacacacccc gactcaatgg aggaccctca tttgtagaag ggtaaaatgg gtgaggcgga   62580
aatgcctgta tggcaccatg gagttctgtg tagccagttc taatcctggg ctatttggta   62640
aggaatgaag ttggagatag tcttctgtcc cttacaacca aaggaattct aactaatagt   62700
ttgccaagtt ttatgtttat aataaaaaat gacatgcttt ttcttttgga tttttaatgc   62760
```

```
ttttgaatta aaaatgctag aacatgaact gattcttcta tcgctattta gatagagcct   62820
tgcaagagca gagcacgcat gctttcttta agaacaggtt ggtttgtggt cgtctgagga   62880
ctgttttaag gagacttatt atacacaatc atcccccaca aatgatttct aaagagaggc   62940
tggtatgaaa gaaggagttt ccatgattct gtcctgtggt tctggggaat tctgaaaatg   63000
aactttagat attttgtga aattcttatt ttcatatttt tggtatctca gagttttctt    63060
ttctggcttc tgtttaacat actcttcttt gccctaaatc tctcttattt ttgctccttg   63120
ggacaactga agaatcctta gataattaat agtatgaaat actgcccttt tagttgaaaa   63180
atgtcacaat aatgtaataa gataaataag gaggtgtcgc tttaacctgt atcgtgtagt   63240
ctcctctact tactaacact tacttgtatt actagaagca ttattttta aatcatggaa    63300 aattggtggc aagctgagca tacagttgtt tatttctgtt tgactgatta ttcaacttc    63360 attatttgat gaaggttctg tacgttttcc tttaagacac atagaaattg tgagaagatc   63420
ctgcagcccc gaaaggctac agtgttgatc caaggactct gagccgagtg cagggtttgt   63480
acttggacct gcaggctggg tggcgtctgt gggagcagtg tgttgagaga gattctgagg   63540
ctgtatgtgt cagggcctcc aggggaagga tgcattgatg gattaatttc tgccaaggct   63600
gaaagaggag agagtaagag gctgtagagg tgtcacagct gtcattgctg ttttaggcag   63660
tcaagctttt gggaaagtgt cagaaattga gccccctact ggatctatcg gagccctgtc   63720
aaatgtccat ttagatgtcc tggtgaacaa agttctctg actcaccatt taaaaacttg    63780
ttccaaatga aattatggga gaaggaaca ttttcatcc gaacccagaa tgaggatgta     63840
cccaaggaaa aggacgtagg ctcaggagct ggactgtggc tcagctggcc tgatgtatcc   63900
cactttgttc ctcccatggc tgggatgtct ctttgctctc catgacccat gtatcttgag   63960
gacatgacac atggaccaag cttgaactgc ggattcattt ttatgcattc tacctgtgaa   64020
tgattgcagc ggatctagtc gtatttctga gagttactca aactggactt cagcagtgaa   64080
ctctacagtt ctcttttcct cccaccttc tattagacat tgcatgatac aaaaatcaag    64140
atatttctaa gagggtgata acttcaatgt tatctaaact tttaatttgg aagaagaggg   64200
gttctttgtt ctttttaaaa agatacaaac gaacttcttt atctgattct ttttttggtg   64260
caaacccatg atgccttctt cctgattcat ctgctacact gtgagttcaa gcctggcgtg   64320
ggacacaggc acagctctca tgccaacgat ctcatggtta agttttggaa cataatttga   64380
aaaatgtaac ccattgagag gcagtaagga catacggtga gctagtgcgt gtttggacgt   64440
ctgtgtggaa taagtgagtg ggtagagagg acatttgtca aggagcggga gggcgggcca   64500
ttggcttggg ggaaatgggc tgagactcta ggggtggcca gcaccgcata cggaggccag   64560
cagggttggg cttggctaag tgctgtggtg tctggatgcc tatgtgagtt tcctccagaa   64620
gttttcagtt ggcaaagtag aacctgctgg atatgtagca agggtgtgga ttgtcgggat   64680
cctgctgggc gcaggcgtgt gataccagag gtcagaacag aagctgaggg atgaggcttt   64740
gggagctttt tgtcatgcac tgtcctggag cctcagttac tacaaagtct gcaaatgata   64800
gaccggagct ttggttctgc ctgatgctag ctcccctgtt cctgatttt cttttcaata    64860 ttagacttaa tcccagaatt cacatgttga agaaaactt agaggtctag tgacataaaa    64920
gcctcatttt gatcgttaca gaactgatgc cttgagaaat ggagagagaa gtacacgatc   64980
atggtaatac tggatgttca ctgagcactc actagctcca ggccttttct aagtaattta   65040
tgaagttgtc aggtttaatc ctcacaacgc ccttatgaat gagctattgt tattatcccg   65100
atttggcaga tgaggaaact gaggcttgag gggaggatga cgtactcaag gtcacacagc   65160
```

```
tgggaggcgg caagctggaa gttgaaccca aggagtctca catcggagcc aggactctca    65220
cccttcagtg ttatgctgcc ttaatcaggc acacatacag gcggggagag gcaggtttcc    65280
ggacaccaga ctaggctggt gccggtcagg ctacaccagg gaacctggag gcctgtcatt    65340
cttttgtgat gctgttagtt cctgttgagg aagtgaggct ttgtgggttc ccaggaggaa    65400
aaggtatgaa ctcatggcaa agaaaggaa ccaaaaaagg gagatttgca tcacaatgag    65460
ccttctattc atcctaaatt atacctcctt ttataccatg tgtgtctgca aacttgtggg    65520
taaatcacaa atctttctgg taagttacaa tggatggaag gttttttgcat ttctctcaaa    65580 tcaccaacca tttaatgcta tgtgtagtca ctccctaatc tatcttttgt ataaatttgg    65640
atctttgagt attggggttt tccatgatgt ttggcagttc cccttagggt gtctatctca    65700
aagtttgtca cactgacaag ctttggggag agaagttaga ggtgggcttc cctgttttta    65760
gtggctgtgt ctgattgttc tgtctgttct ccaggacagg agagattgat tgctttctag    65820 cttttttaa aattaaaaca acaacaacaa aaaatacag aaaggtacaa aggataacaa    65880
acacattcat gtacctgcca cctaaaataa caattactaa tcttttcacc ctcctagccc    65940
atgatcttcc ctcccaggct gttattaata tgaaaaccga gttcaggttt ttatactttt    66000
cgacatctat ttatattaac gtatgtatta taaataatct tagtagtttt taactttgac    66060
ataagtggct tcacattcca cataacattc tgcagcatgt tttctttat ttttattttt    66120 ttctttattt ttaaattttt attttgcagc atgcttttct tattcaacat tacatttgaa    66180
ttttttcaac attgtacatt gaatttagc tcattctttt taactgctct gtagtattta    66240
ttgtatgcat atactacagc tttctatttc tgtattgatg gttaattagg ttgcttacag    66300 tttttaaga ttacagattc tgctgtaata accatccttt gggcaagtgt atgtaggtac    66360
ctatatatga gtttctctag gattcatacc aaagtagagg aattggtagg gcattggttt    66420
gctggtttta attttaattc acatgctatt gtcaagctct ccagaacaac tggatgagtt    66480
gattggatca atgagtattt ccatcaccag catataaact cttctcctcat aatcacacca    66540 atgcttgatc ctgttggact taaaattttt gccaatttgc tgggtatgca acggcatctt    66600
acctaatttg cctttatttg atgactcctg aggttgaaca tctggtcata tgtttatttt    66660
ctcctctgtg gcttgcctgg tttaatgcct tcttcatttt aaagaatcag atagttttct    66720
gttattgatt tataggaact ctttatataa gttgaaaact tgattatatg tgttggaaat    66780
acttttctta ggctgtgatg ttttaaaata ttgcttaga tgggttttca tttttacctt    66840 ttatttaga gatggagtct cactgcattg cccaggctgg attgcagtgg ctattcacag    66900
gaaagagcat agtatgttac agcctccacc tcctggtacc aagaggtcct cctgccccag    66960
cctcctgaat aggtgggacc acaggtgcac atcactgtgc ctagctttgg atgggttttg    67020
aaagaaagaa gttttaaatt ttaatgccct caaattcatc tgtatttcc tctgtgcttt    67080 tattttgtac ccactctaag tagctccgaa ttctgcagat agttggtgca ggaattctga    67140
ttttgagtgg acatctgctc tctaacagtc acattgaagg aaattaggtt ttttggtag    67200 gaatctaagc aaggggttga tttgtaaact aggctttaaa tatgattta agcaactcac    67260 ttagaacaag atacaaaaat tgtggactgg acctatatct ggaaaacttg aaagtgctag    67320
ggcaataaat aattcttggt cacatacagc cgagatcctg ggctcctgac tctgggacag    67380
aagcttctta tattttatct catcagtctt tgcaacaggc tccttgaagc aattttatcc    67440 ccatttaga gataagaaaa ccagagctta aagcagttag ataatttatg aagtaagtgg    67500
```

```
cagagccaag attcaaatcc agacctttct gaccacaaag ctcgttgctg aataccgcgc    67560
ctcattgcct tcttgcgaat tacttgggat ttgtttgaat cccaaaatct ttatatgtta    67620
ttttaaattt gaatctaatt ggaagtgggg cagtgagggt agaggacaga aagaagggga    67680
agagcttgag actcaataat agaaacaaaa aacccgtctc caggagggcg gttcaaaagg    67740
aagaattcca tatttcatgt aactgaaacg ttaaaagccc aaataattgc atcatgcaag    67800
tctgatgctg agtaatcacc ctcccccata ttattgggga gaggggggcaa gaagtctggg   67860 aagctgtttt tgcctaagga attacattcc aggggactct gaggatttag gtaaccacaa    67920
aagccattta tttcgagtac actgagattt ctaccacttt gatccctaat ccatagcata    67980
attaataaat gaaatgtgct gtagcatggg tttttttacaa agtgtacttt taaaatggct    68040
tttggtctga catgattcat ttgccacttg gaaaagcgtc atcgcctcag atgggcaggc    68100
tgggagaggc tgcctggtgg gtagctgagg gcggtttcct ggggcacagt tcctgccttg    68160
ggcctctaca gagcggtctc atccaaacat ctcccagact ctgcgttttc caggaagcgt    68220
gcagaaatag gaggccagta ctgaaatgct atctgctctg tgtatgtcag aagaccacaa    68280
accacttata acaaatgaag atcttttttat ttgttcttat ccctttatgt cacttgagga    68340
aagttgctgt gagtaggtga tgatcattac agtgatcact ggttgcccaa actgagaagc    68400
cagacatttg gcttggtttc tctcccttcc tcttgtctct cctaccctgt aaacacatac    68460
ttggtgatta cccatgggga gacaagacag gctgggaata tatacttctg caacttcagc    68520
ctcctgggtt ccagcgattc tcctgcctca gtctccagaa gagctcggat tacaggtgtg    68580
caccaccagg cccagctaac ttttgtatt tttagtaaag atggggtttc atcatgttgg     68640
ccaggctggt ctcgaactcc tgacctcagg tgatctgccc ttctcggcct cccgaagtgg    68700
tgggattata ggcgtgagtc accgagcctg gccccaggca ataatatacc agtgggcaag    68760
aaaatattct tgctctcatg ggacttctgt tgggggtcag ggtataggga ggaaggcata    68820
gagatgaaaa ccagtaaaata agtaacaggg gaaaacattt taaatacatt aataactaat    68880
aaaatagaaa taaatctgtt ggctacttaa caggatgtgc cacattccag atacattacg    68940
ttaatcctta tgatctttgg gggctaagta ttagtattcc attttacgga tgaagagact    69000
gaggctcaga gggaagggag gtggcttttc tcaggtggaa agccagacct tttcagtggt    69060
cattcagttc atagctaagg tcttattttc tgtgctctct gtcggctgaa aatgggcaag    69120
gtaatttcac atagtgacag agccatgtc agagaaagag caggacagtg ggacagagag    69180
ggaccaggct gggggctgtt tgagatggag ggtcaggaag aaccaaacta agatgtgaac    69240
agtgggaggt gttggagctg tggtgcttgc ctagaaggac cctcatcgag caaatagaag    69300
cttctggcag gaagaagtta atgtcttgcg tgtgccctat gtaggttcat tagggccttt    69360 aaaggggaa gaaggtggtg gctataaatg ttacaatctt acctttggcc cctagggatt     69420
ctgtctttca accttggttc agtaacaact tgtgactgcc caacagggct tccttttcggg   69480 agagaatggc ttgttacatt caaatatgcc atgaaagtat caccatttat ttcagtgtct    69540
gatgccccag cttgggcagc ctgagcaggc tctgaatggg tctgaagagg ccctttagag    69600
tagagatgaa gaggggtgg ggaatcctca attctaaaca aagagtctgc aatgggaaga    69660
tggccaaatg ctgttttttgg agtgggtgag agggaaaaga aaggtataga tggttcgttg    69720
gaaaatgtgg ttttataccg ggttttggtg tcaggtcccc gagggcaaca tggactccac    69780
actgtgatcc tccgggcagc tcatagcccc agccccttcc ttttgcttcc tggtcagttt    69840
gtgagaagga ggggttgtgt ctccaatctg agcaataagg ggtctgaggg gggttggatc    69900
```

```
catgtggctt tcctgtgtct tgttccttgt aaaagttcca ggttttgggt cgtgagctgt    69960
gtgtgtgtgt gtgcgtgtgt gtgcgctgta cgttaatatg gagagatggg cttgggccag    70020
tgggaaatag agagacccgc aagcacagag tgacagggtt tgatagtaag cagcaggcca    70080
gcgttgctgc ttttattcct cggtaaatcc ttgcacaatg ccatatgctc ttgcattccg    70140
tagctgctgc atagggtgtg atttagttaa tgcccgctct gcaaacagga aacggtgctc    70200
actgctgtgt atgcttttca tggagataaa gtgtcaggag caagacccca aacctgcgaa    70260
atcactaatg caaccgcccc ccatgcccca aaaggtggga gtgggggata aaaagagtag    70320
gaaagtggtg tggggagggg aagctttagg gccataactc agacaatttg tcaggcagtg    70380
gcatcggttg ggaggaaaat attgatgtac acttttttgtt tttgaacctg aagtttgggt    70440
tttttcggat gcattggagg actttttaaat gttttcggag tgccagagtt tggactgtta    70500
ggtcaccgta ggtaccggct tgcatatcat ttcagaggaa tattttcaaa actccataaa    70560
aacatgcggc tttcaaggct ggaccacttg ttcaggtcct cctcccaccc cccacccttt    70620
ttggcaaaac catgcaaaca ttggtattca aaatatttt gttactttc ttggcaaagt    70680 gttccaagaa ggaattgcaa cacagtctca gagttaggag gcaactttct ggggaaaagg    70740
cgggggttgg ggaggtttgg agtttgaatc aaaaacagac accgaagctt taataaaata    70800
aatgaagcgg agccctttca gctcacggtg gactgtgttg gtgcgcgggt caggctttaa    70860
cgtgcctagt ggaaattgac agtctgagaa ctgggacata aacaaaaatg tcagtccctg    70920
ggagtcttgt tcactggaca atgtctcaat tgttcctttg gttttcaagg cagcaggag    70980 agtggaatat taactgttta ctgcccaaag ctggctcgga aattgcttgg agaaggggag    71040
aaaaaagaca gaaaatcaca ttttttattt agaaactatt aaacatgtca gtaagagata    71100 ggaaagagc agattgtttt ctccttaatt atctgccatt cacttccata tttctgcata    71160 ccattttttgg ggtgtgtgtg tgtgaaggaa cagcagggtc tttcttttta aatttgaatg    71220
ttagccttgc atattgtcag ttttttaaagc ttgctggcat gtagattatc cgcccccggt    71280
ggatatgaca gtgggcttta ggaaaggaag tgtgatttct gataacatttt acatcttagc    71340 tgttcagcgg ataccctgtt agtgtttgtt cttcagaatg ctcagataga acaaaaatca    71400
agtggttgga attttaaaaa acaaaatgta tttggctctc cataaaatg catttagtga    71460 taaaggggg cagcaagtaa ctatgtctga gagaaggaat tgcaggcaca gaggagatcc    71520
agaattctgt tcacacttga atttacttga ttcgagaaac aaacagcaaa gcctggtgta    71580 ttggcctta tctgggcaaa gttcaaaact caactggtaa ttatgtcctt agaagcctta    71640
aaaggactgt gttgttacaa aagcagtgac tgagcttact tcttcaggac cgaatgcact    71700
cgagttgttt gttagataaa cttgttttaa taaatggggg ggtcagggga gaggtttctg    71760
ttcttggaag attccctgat aagtagcttt cttctcttgg agaacttcag gctttctctc    71820
caagcgaggg gttttgcaggc agctaaagtc agcttcggct tctgcttcct gtcagtcagg    71880
aagtcacttc cttaacccaa attacaagct agagcacaac tccccagcca taccgaaaag    71940
agcaggtttt tcccagaaga ctgtgtttct agatgcggaa gtgtaaattg gtacgctgtg    72000
tgatcatgga atgcccaaaa tacataggga acagtgttgt tggaaagagg cgctgtgtcc    72060
ccaaggagaa gacgccgccc agaatggctg gatcgcctgt tgtggctgag tgcgaggcag    72120
ctgtggctgg ctgctgtgtg acgatgacct agtagccacc catgtggagt cctggctgcc    72180
tcagaaccct atcacatcta ggcaaaatct tgcatttttt atctgggagg cctgaggact    72240
```

```
tcagggctgg tggatagtaa gctccttggt tatctcacag atacaagagg tcttgggaat    72300
ccacgatcaa acttgatgtg tgcgtttacc ctcctccctt tgaatctgtt attcaaatat    72360
ttaagcctcc aaccttgtgg cccctacctg caccacccct cacccccccg acaaaaatca    72420
agctcttgac ctcatggctt ctttcagtga cccttggggg acagggtttc ccaaggctgg    72480
ttgccagctg gcatggtccc ccgttggtga agtggagacc tgtgttttt  tggtcatttt    72540 gcaaagagct tatggatgac agcagttctc tgtgcctcgc tgggacagag tgtattctga    72600
ggtccagcgt ctgcatggag atctgcctat ccttcacttg gggtgctcag tagataacgc    72660
ggccactttc ctatacattt ccttaattta agggaacagc gtaaactcag cccaggtgga    72720
ttaatctctc cagtgacttt tgaaacttca atttccaatt tccctcttat gtctaggtgt    72780
gagtgaggat acgtgtagta attgtcgcag gtattagtga gaaagggtgc agatcacaca    72840
aatatttcac acgttattag ttggaccaga ctttggaggc aagggagggc cgtgtcacct    72900
aggaaatttg ctcttccgtg gagatgaaag ggcagtgaat taagtgcctg ctttttctcc    72960 cttttttccct ctgacggtta ttgatcctcc cctggaactg tacagttcac gttctgatct    73020
ttttcttgac aaagggaatt cccagtttgt tcgctggcga acgcactagc aggtgaggag    73080
ttaaaagttg gcaacgcctg ccctctcgag agtgtcagga ttttttagtct cttccttgag    73140 agctagaaga tgtttctaaa agaatctctt tggtgactta aagtggaga  gagctttaga    73200 agcatggcac aaataaaagg aaagaggcaa acaccgtcat tctacatctg tttatttttgt   73260 tattaacaaa aggcaaggcg attttcatta aagttttgct ggggttgggg ttgagggtgt    73320
agagagcaaa agtgtgagtt gtacaccatg actggaatcg cttggacata ctcttcagca    73380
gacatcgtgt gactgtggaa gaaatgagtt tcatgaagat gactgataga aggaagccac    73440
tgaaccagtc ctctatcacc tcttccaagg ctaaagtttg gagccacttg cagaaggctc    73500
tcctcaaacc cctgtgttct ttgcctaccc ctgctgttgc cacatcatct tggagagctg    73560
gctgcttccc tcctcaacta gaagttccta gtgcctgctt agttcttgtc tcttgcttcc    73620
caagtgctca caaaatacat ccatgttcgc tacgaggaaa tggaccacat aaggtttccg    73680 tgaaaaccctt agcccttagg tctaacacag taggaacaga agttaatgtt ttcctgacgt    73740
agaagtttct cttgctgctt ctggtcacat ttctttcttg tgtggttctt ctatggctac    73800 tgcactttt  ttttttttctt actgtctccc ccttcccca  cacaccacct tttgggata    73860 gggtggcagg tgagaatata aacagataat ggttaagaga tagtttagtc tttctaggcc    73920
agattattta gttttttgcca tctaggtaaa attcggtcca attaagcgtc cattaagtgt    73980
tttaatataa gctggagaag gagttgaacc tggaggtcag ggctctgtgg tctattacag    74040 tcccctggg gtctctagcc caagggagac tccagggtct taataaatga ctgggggttt     74100
cattttgagg cctttactac caaagactga ataatacatt gggcatgatg gttttgtcct    74160
aaacattaac agccacaaaa ggtagagagt gtgtctgttt atagatacac atgtatcatg    74220
aataattagt tggggactgt gcatcaggtc tctcattta  cattcgagga agcaatgcac    74280
ggaatgaatt ctgaccctgc gaactctgaa tttcaattct ctgtctccta cttttactgg    74340
agtgcttgca aacagtacag tgttttgtt  gtgaagttat accgtgcctg taatctctct    74400
gcgggtggcc ctcctaagcc ctacttcaag aaatagctct aagctcatga cacccgcccc    74460
acccgatgcc tacatatgtc ttatatcctt ggagtagtgt ttggggttgc aaatttgact    74520
ttagggagac atactctctg atgataggct aatgcttata tttactgata aacttccttt    74580
ttgacggtca tgggcttcgg gggccaccca accaaactgt gtggctgctt ttatgttggg    74640
```

```
ccaaaagaca ggctccttgt gtcctcccag tttcttaaac aatgaagtca tggcatttta      74700
cagtgctggt gaatggattg agattgtggt ggccctggaa tgtggcactg ctctggctgg      74760
agggaagatg agagtgaggg atggagagga gaggagagcg ggagatggga acctggtgga      74820
cacaggaggg agtgtgagtt ctgagggcca aaggaaactt gacaccggat gggacattaa      74880
tctgattctg ttatctgagg ctgtcaccag tcctccctgt cctcctggca                 74930

<210> SEQ ID NO 2
<211> LENGTH: 384
<212> TYPE: DNA
<213> ORGANISM: Homo sapiens

<400> SEQUENCE: 2
ttcaggccat tggtgttgta tatatttcaa gatttgctca caggtccaaa gcttaactta        60
agctccctga acatatcat aaaatatgat ttggggaaaa accctaatgg gccatgatca       120
gaacattatt attcaacaaa ggatgaaatg cttaagccaa gatggccttc tttctttctt       180
tctttctttc tttttttta atgaaagttg agcagactcc cgtccaacag ttttcaatgt       240
aggaattccc acagccccat tgattgcag tttgttgaaa agtttaatgt ttttgtaggc       300
aattcataat ttccacattg aacagcctga gaggaagaga gctggagccc actgttgttt      360
ttgtagtggg atggtgggaa cttt                                            384

<210> SEQ ID NO 3
<211> LENGTH: 20
<212> TYPE: DNA
<213> ORGANISM: Homo sapiens

<400> SEQUENCE: 3
ttcaggccat tggtgttgta                                                  20

<210> SEQ ID NO 4
<211> LENGTH: 20
<212> TYPE: DNA
<213> ORGANISM: Homo sapiens

<400> SEQUENCE: 4
aaagttccca ccatcccact                                                  20

<210> SEQ ID NO 5
<211> LENGTH: 366
<212> TYPE: DNA
<213> ORGANISM: Homo sapiens

<400> SEQUENCE: 5
ttgtcccttg aggtgtactg gaaactaagg cgtgagggac tcatagggt ctggcttgga        60 aagtgtattg ctatgtccag tttacacata aggatgtgca aatccagcag gttagctgag      120
ctgcccagga atatccaggc aagaatkacc atattctgat aattactcag gcctctgcct      180
catctccgct gcccccccgc cccctgactc tcttctgagt gccagattca gcctccattt      240
gaatgccaaa tagacaggaa attagcatgc ccagaatcca cgtctttagt gcactctctc      300
cccagctcca aacctgttac tgcttgtgtt caacatctca gtaaagctca acaacatcga      360
cccatt                                                                366

<210> SEQ ID NO 6
<211> LENGTH: 21
<212> TYPE: DNA
```

<213> ORGANISM: Homo sapiens

<400> SEQUENCE: 6
ttgtcccttg aggtgtactg g        21

<210> SEQ ID NO 7
<211> LENGTH: 20
<212> TYPE: DNA
<213> ORGANISM: Homo sapiens

<400> SEQUENCE: 7
aatgggtcga tgttgttgag        20

<210> SEQ ID NO 8
<211> LENGTH: 558
<212> TYPE: DNA
<213> ORGANISM: Homo sapiens

<400> SEQUENCE: 8
gctgtgaaat cccctgtgta gtgggaagaa gaaatagcaa atcttagctg ccttggacct        60
gatataatta tttgtcttca tttacatggt tyatccttca aggttgaata atgatgtgg        120
gagctagtca aggggcttta ggtatgtgat ttcatgccta ctttttttta ggtagagaaa        180
ctgaggtcac agggtactag agaatggact ctaagattca ggtttctgaa ttgcctgtgg        240
ttttgttgac tcaactgctc ttctgttgtt tttagccac atgccttgaa acagtcctct        300
ttcccatgtt tcttcatcag caccattaac ccaaggtata ctgtcctctc ttatctttca        360
caaggtcttg gagttcccat gcctttgtaa gcatccctcc ccgagattca gcaccaacca        420
aaatcacatt tggaaaaatt gcttgtttcc caagaagctt tggaggatat gatttttgtat        480
agaacgggtt cacaggtttt ctgttcattc ttctatggtg gagtgtgtgt gtatgtgact        540
ctgtcttctc tccattcc        558

<210> SEQ ID NO 9
<211> LENGTH: 21
<212> TYPE: DNA
<213> ORGANISM: Homo sapiens

<400> SEQUENCE: 9
gctgtgaaat cccctgtgta g        21

<210> SEQ ID NO 10
<211> LENGTH: 23
<212> TYPE: DNA
<213> ORGANISM: Homo sapiens

<400> SEQUENCE: 10
ggaatggaga gaagacagag tca        23

<210> SEQ ID NO 11
<211> LENGTH: 364
<212> TYPE: DNA
<213> ORGANISM: Homo sapiens

<400> SEQUENCE: 11
aagggagaaa gcaggattga gcaggggag ccgtcagatg gtaatgcaga tgtgatgaga        60
tctctgccgg accaaagaga agattccttt ttaaatggtg acaaattcat gggctttctc        120
tgcctcaaaa cctagcacag ctgttattta ctgaacaatt agagagctaa gcactttta        180
gatayta tat aatttaattg ccgtatgagg cacccttagt tttcagacga gaaccacag        240

```
ttacagggaa ggcaagtaac ttagtcaatg tcagataact aggaaaaggt tagagggggcc    300 ctggacacag gcctgtgtga ctgagaagct tgggcacttc actgctacat tcatctctt     360 cgct                                                                  364
```

```
<210> SEQ ID NO 12
<211> LENGTH: 20
<212> TYPE: DNA
<213> ORGANISM: Homo sapiens

<400> SEQUENCE: 12
aagggagaaa gcaggattga                                                 20
```

```
<210> SEQ ID NO 13
<211> LENGTH: 22
<212> TYPE: DNA
<213> ORGANISM: Homo sapiens

<400> SEQUENCE: 13
agcgaagaga tgaaatgtag ca                                              22
```

```
<210> SEQ ID NO 14
<211> LENGTH: 579
<212> TYPE: DNA
<213> ORGANISM: Homo sapiens

<400> SEQUENCE: 14
ctgatgaggg tagggagcat ctgtctgcag cttcatcttc attgtctagg ggctccagaa     60
atatctgtga gtaaataagt tatttaatct ttgcctcaaa tttccagtga ctgtagggat    120
atagctgtga gcctctagga gctgagattt tttaaatttc ccacttaaac atttatttaa    180
aaattttgtg ctcagcatgg actaaggact ttacattcat taactcattt acagcttgat    240
cctatgcggt gggcattcat ttacagagga tcccatttta caggtgagga agaggccagc    300
taggggtgca gcctaggtta gtattctaga gctcatcagg ctgtgttgtc cccagtgaaa    360
gaataagcaa agaagtgaat gttgtgcatt gagaaaaatg actctcggag gaggatgagc    420
ctctcggata tggcgaccga agtgatwtgg ggcccttgtc aagggtctct attatggcat    480
caagaaaaga tgctgctttc ggtgatgccc gaggagagcc tcaatatttt acatgggaaa    540
cctaaaaaag gggccatgtt gtggtctctg cacctaaga                           579
```

```
<210> SEQ ID NO 15
<211> LENGTH: 19
<212> TYPE: DNA
<213> ORGANISM: Homo sapiens

<400> SEQUENCE: 15
ctgatgaggg tagggagca                                                  19
```

```
<210> SEQ ID NO 16
<211> LENGTH: 22
<212> TYPE: DNA
<213> ORGANISM: Homo sapiens

<400> SEQUENCE: 16
tcttaggtgc agagaccaca ac                                              22
```

```
<210> SEQ ID NO 17
<211> LENGTH: 486
<212> TYPE: DNA
```

<213> ORGANISM: Homo sapiens

<400> SEQUENCE: 17

```
tatttagaaa ccataaaatc cacctatttg aggtgtacaa ttgagtgatt ttctgtatag      60
tcacagatct gtgcagtcat ccacaccctc taactccagg acattttcct cacccccgag     120
gagaaacctc ccttacccat tagcagtcac tcctcatttc ctctccccccc agccctggc     180
aatcactgtg gatttgcctg ttcttgacat ttcatataaa tggtatcata aaatctaygg     240
gcttttgtgt ctgtctgctt tcacttagca tacggttctc aaggttcatc cagtattgta     300
gcatctatca gtatgtcatt cctttttatg gccaaataat attttattgt atggatagac     360
attttgttta ttcatttatc tgttttttggt tattatgagt aacactacta tgaacatttt     420
gcacaaattt ttgtattgac atgttttcat ttctcctggg tatagtccta tgagtggaat     480
tgctgg                                                                486
```

<210> SEQ ID NO 18
<211> LENGTH: 27
<212> TYPE: DNA
<213> ORGANISM: Homo sapiens

<400> SEQUENCE: 18

```
tatttagaaa ccataaaatc cacctat                                          27
```

<210> SEQ ID NO 19
<211> LENGTH: 22
<212> TYPE: DNA
<213> ORGANISM: Homo sapiens

<400> SEQUENCE: 19

```
ccagcaattc cactcatagg ac                                               22
```

<210> SEQ ID NO 20
<211> LENGTH: 428
<212> TYPE: DNA
<213> ORGANISM: Homo sapiens

<400> SEQUENCE: 20

```
ttgtctcctt ttgtttctgc tactgtgaat gatcctgtga tgatcatctt tgtgtgtaaa      60
tctttgtccc ctcgccccct cccctttat tattttcttg ggatagaccc caggacaaaa      120
ggtagaaaag aacaaagtgt taaaaaattt cttgatacat agccacagat tattttcctg     180
aaagttctca acatttataa ctacsagcag tatgtaagag agttatggtt ggaatgattt     240
taatgtctct ggggaattta acaacaaaaa aactttaggc ttctttggag agagacatgc     300
ccttaactcc acccgccct agaacagaga cccagcccat ccaagtcagc ctccccaggt     360
cctccacctt caaaacaggc aaacgaaatc atttcttgaa taattggtag gcttcaaggt     420
cagatgtt                                                              428
```

<210> SEQ ID NO 21
<211> LENGTH: 23
<212> TYPE: DNA
<213> ORGANISM: Homo sapiens

<400> SEQUENCE: 21

```
ttgtctcctt ttgtttctgc tac                                              23
```

<210> SEQ ID NO 22
<211> LENGTH: 22

```
<212> TYPE: DNA
<213> ORGANISM: Homo sapiens

<400> SEQUENCE: 22
aacatctgac cttgaagcct ac                                              22

<210> SEQ ID NO 23
<211> LENGTH: 330
<212> TYPE: DNA
<213> ORGANISM: Homo sapiens

<400> SEQUENCE: 23
tcagggacag tgcataggtg taaagaagtt gctggttggg ggttctaatg caggtttctc     60
caaaagtgaa tgccctgtta aaaaaaaatt cttaacaaat atacagagat ttttttttta   120
aaaaagtgtg acagttctag acacctagag agtaaartga agaagcctgt tttcaggttt   180
cccgcctccc tgaatttccc agcatggtcc aggctttgaa atttatttat ctgcttttgg   240
caatggttga tgggaatttc ccacatttat tttttagcta cagagaaagg acattatctt   300
taaaatctct tcgttgttct ctctctttga                                     330

<210> SEQ ID NO 24
<211> LENGTH: 20
<212> TYPE: DNA
<213> ORGANISM: Homo sapiens

<400> SEQUENCE: 24
tcagggacag tgcataggtg                                                 20

<210> SEQ ID NO 25
<211> LENGTH: 23
<212> TYPE: DNA
<213> ORGANISM: Homo sapiens

<400> SEQUENCE: 25
tcaaagagag agaacaacga aga                                             23

<210> SEQ ID NO 26
<211> LENGTH: 574
<212> TYPE: DNA
<213> ORGANISM: Homo sapiens

<400> SEQUENCE: 26
tatttagaaa ccataaaatc cacctatttg aggtgtacaa ttgagtgatt ttctgtatag     60
tcacagatct gtgcagtcat ccacaccctc taactccagg acattttcct cacccccgag   120
gagaaacctc ccttacccat tagcagtcac tcctcatttc ctctcccccc agcccctggc   180
aatcactgtg gatttgcctg ttcttgacat ttcatataaa yggtatcata aaatctatgg   240
gcttttgtgt ctgtctgctt tcacttagca tacggttctc aaggttcatc cagtattgta   300
gcatctatca gtatgtcatt cctttttatg gccaaataat attttattgt atggatagac   360
attttgttta ttcatttatc tgttttttggt tattatgagt aacactacta tgaacatttt   420
gcacaaattt ttgtattgac atgttttcat ttctcctggg tatagtccta tgagtggaat   480
tgctgggtca tataataaat aactgtttaa cattttgggg agctgccaaa cttttaaaac   540
cttgggttct gtgatgtacc agttgtgtta ggca                                574

<210> SEQ ID NO 27
<211> LENGTH: 27
<212> TYPE: DNA
```

<213> ORGANISM: Homo sapiens

<400> SEQUENCE: 27
tatttagaaa ccataaaatc cacctat                                              27

<210> SEQ ID NO 28
<211> LENGTH: 22
<212> TYPE: DNA
<213> ORGANISM: Homo sapiens

<400> SEQUENCE: 28
tgcctaacac aactggtaca tc                                                   22

<210> SEQ ID NO 29
<211> LENGTH: 571
<212> TYPE: DNA
<213> ORGANISM: Homo sapiens

<400> SEQUENCE: 29
tgccaggggt tttatggtta attttcctcc attatgaggg ttgactcagc cttgggtatt          60
agatgtcttt gagaatccag ggttcaaata ccacagctgg tagaatgttt ctcaacttgg         120
agccaatctc catctactga aggtacgctg gtttagacag acaacaggga catcagcatt         180
ttaaaaagcg gtggaaaaag tttgcttgtc ttgattggag ccatgacatt ttattttgaa         240
atttcaaata acatgaaggg aggtttggag cggttttttgg tttatccaaa gggcagtgga         300
ttgaaggctg agaaacacca ggctgaatgg gagaggggtt ggggtccccc tgtgagatag          360
tgaaacaatg gtagtgccat ccaatgatag gcacttttct gtcattcaga agcagaaagg         420
gggccagagg cccattggcc ttactgggma gtaagctgta gagctgctgc cttttcgtga         480
aagggttgac accaaccttc tcccccagga agagtgacca gggacctgag gggcatggtc         540
gagcagatga cagcctttgt aaaacatctc c                                        571

<210> SEQ ID NO 30
<211> LENGTH: 20
<212> TYPE: DNA
<213> ORGANISM: Homo sapiens

<400> SEQUENCE: 30
tgccaggggt tttatggtta                                                      20

<210> SEQ ID NO 31
<211> LENGTH: 23
<212> TYPE: DNA
<213> ORGANISM: Homo sapiens

<400> SEQUENCE: 31
ggagatgttt tacaaaggct gtc                                                  23

<210> SEQ ID NO 32
<211> LENGTH: 614
<212> TYPE: DNA
<213> ORGANISM: Homo sapiens

<400> SEQUENCE: 32
ttggtagaga tggggtctcc taggctggtc ttgaactcct ggrctcaagc aatcttcctg          60
cctcagcctt ccaaagtact gggattactg gcgtgggcca ccatgcctgg cttgaaattt         120
ttctatggct ttattctttc tccaagtaca gagtctaccc aaccttctga gatctttggt         180 tttctttttcc taggtaacta tagtacatac ttatttatgt taaacaacag caatcacaca        240

```
tttcttttc  tatacagtca  tgctttatag  gcaaataaag  cctccgtctt  aggctttctg    300
gattttttca  aaagatgcaa  ttcctggagt  atgtttttac  ttagagcaaa  gcagcctagt    360
ctcctatacc  ttctgcatct  gcagaaaagt  tggttaaaca  gactttgtaa  tgatgcccct    420
tacaattctg  aagggacttg  tgaaatagtt  tcacagagtt  tcagtgttag  gtatatttga    480
tcaatgctaa  cttttggaaa  acttggtgc   ctgtatgatt  cagagggtag  ggcagaatat    540
taaattaatc  acaacttctt  gtattttaac  cattctgggt  aaattgggat  tccgtgacgc    600
ccaggcaaaa  ttat                                                          614
```

<210> SEQ ID NO 33
<211> LENGTH: 20
<212> TYPE: DNA
<213> ORGANISM: Homo sapiens
<400> SEQUENCE: 33
ttggtagaga tggggtctcc                                                     20

<210> SEQ ID NO 34
<211> LENGTH: 20
<212> TYPE: DNA
<213> ORGANISM: Homo sapiens
<400> SEQUENCE: 34
ataattttgc ctgggcgtca                                                     20

<210> SEQ ID NO 35
<211> LENGTH: 633
<212> TYPE: DNA
<213> ORGANISM: Homo sapiens
<400> SEQUENCE: 35

```
tatcttatat  cccctccaag  cattcattaa  ctgatggatt  agtgagttgg  ccttgagaag     60
cataaaggct  cgtctccatg  tgcttctaag  cattgtgtct  aagttctgtt  tggtttcctg    120
agtgaaactg  tcttaatgtt  accaacagaa  gttaaatgcc  taagagwttc  ttatacatgg    180
gctgagtacc  tctgtgactg  ggcaagccac  ctcacctcat  tttaccttgt  ctgcaaaatg    240
aggaactggg  tcaactcatc  gttcaaatct  cactgaaagc  taattgatcg  cttttgacag    300
aagtagctcc  cttgggccgt  atatttattt  cctagcttgg  aggaaggtgg  ggacagacag    360
aattgatgta  cacctttatt  tttatctcta  tggtaaacct  gtgcatacta  aagcattcct    420
ctggtctttt  gagatgagtg  tatacattgt  gtctggccct  gtgcatttt   taccaagaag    480 taagttttgt  tgagtaaact  tgggttgtat  gaagaactgc  atgctcaccg  tactcaagta    540
gcttttgcta  cctaaaggac  agctgctcat  atgtacttga  cttcctttaa  agtgaaggat    600
gatgacattt  gaaaaacgga  ggttgaaaag  gag                                   633
```

<210> SEQ ID NO 36
<211> LENGTH: 25
<212> TYPE: DNA
<213> ORGANISM: Homo sapiens
<400> SEQUENCE: 36
tatcttatat cccctccaag cattc                                               25

<210> SEQ ID NO 37
<211> LENGTH: 21
<212> TYPE: DNA

<213> ORGANISM: Homo sapiens

<400> SEQUENCE: 37
ctccttttca acctccgttt t                                              21

<210> SEQ ID NO 38
<211> LENGTH: 1081
<212> TYPE: DNA
<213> ORGANISM: Homo sapiens

<400> SEQUENCE: 38
ttgagcatgt gttatttaat gagttatacc tctgtcatat gtgtgtgttt atatcacaaa     60
ataacttatt tttataaaac catattttga gtcatcattt gtgacaatgt cttctttctt    120
ctggtataaa tgaggcatgt agaaagaaga ttgacatttg ctagaagctt cccctttcct    180
ctaactccac aataaaatgg atgctcataa ttacatctgc tcctataagg tcaagatttc    240
agggctggaa gtgaccttag atcatttagg cccaacttgc cctcaggaaa ggaaactgag    300
gcccagagat gccttaagtg aattgcccaa tgtcacacgc tgagtcagtg ccagagcaa     360 ggcttggatc cagttctctg ctccctttcc agagccttgt gatgtcttct ctcctacagg    420
aggtgaaaat aactgctgtg gctggttctg ttttgctgac tgtaaattgg gtcatggtca    480
gggacagtgc ataggtgtaa agaagttgct ggttgggggt tctaatgcag gtttctccaa    540
aagtgaatgc cctgttaaaa aaaaattctt aacaaatata cagagatttt tttttwaaaa    600
aagtgtgaca gttctagaca cctagagagt aaagtgaaga agcctgtttt caggtttccc    660
gcctccctga atttcccagc atggtccagg ctttgaaatt tatttatctg cttttggcaa    720
tggttgatgg gaatttccca catttatttt ttagctacag agaaaggaca ttatctttaa    780
aatctcttcg ttgttctctc tctttgagtg aggagagaag atgtgaatcc tggcagtggt    840
tcagagtgga cacagcccct gtgtttgtgg cataggctct gtgggcccca tgccagggag    900
cagtaccccc gtgtaaagga gtgggggttt gtccatttgg atagagcaaa gatcctccac    960
ctcaaatccc acaagaacag ttgccacaac ctgggcccta agcatctcat tttcctatgt   1020
agaaattaat gatctggagg agatggcaaa acattccttc cagagcctgt gtggattttg   1080
g                                                                   1081

<210> SEQ ID NO 39
<211> LENGTH: 26
<212> TYPE: DNA
<213> ORGANISM: Homo sapiens

<400> SEQUENCE: 39
ttgagcatgt gttatttaat gagtta                                         26

<210> SEQ ID NO 40
<211> LENGTH: 20
<212> TYPE: DNA
<213> ORGANISM: Homo sapiens

<400> SEQUENCE: 40
ccaaaatcca cacaggctct                                                20

<210> SEQ ID NO 41
<211> LENGTH: 599
<212> TYPE: DNA
<213> ORGANISM: Homo sapiens

<400> SEQUENCE: 41

-continued

```
tagtgctcag tatttccaac gttctgttta tttaagatga aaattgctgt agttaataag    60
cacttcccca tgtcattaaa atgcttaagg attttttaatg accacataac agtccataat   120
atgattaaac cccaatttac tgaatcaatg ccatattgtt gggtctttag attgtctcct   180
tttgtttctg ctactgtgaa tgatcctgtg atgatcatct ttgtgtgtaa atctttgtcc   240
cctcgccccc tccccttta ttattttctt gggatagacc ccaggacaaa aggtagaaaa    300
gaacaaagtg ttaaamaatt tcttgataca tagccacaga ttattttcct gaaagttctc   360
aacatttata actacgagca gtatgtaaga gagttatggt tggaatgatt ttaatgtctc   420
tggggaattt aacaacaaaa aaactttagg cttctttgga gagagacatg cccttaactc   480
caccccgccc tagaacagag acccagccca tccaagtcag cctccccagg tcctccacct   540
tcaaaacagg caaacgaaat catttcttga ataattggta ggcttcaagg tcagatgtt    599
```

<210> SEQ ID NO 42
<211> LENGTH: 25
<212> TYPE: DNA
<213> ORGANISM: Homo sapiens

<400> SEQUENCE: 42

```
tagtgctcag tatttccaac gttct                                          25
```

<210> SEQ ID NO 43
<211> LENGTH: 23
<212> TYPE: DNA
<213> ORGANISM: Homo sapiens

<400> SEQUENCE: 43

```
aacatctgac cttgaagcct acc                                            23
```

<210> SEQ ID NO 44
<211> LENGTH: 599
<212> TYPE: DNA
<213> ORGANISM: Homo sapiens

<400> SEQUENCE: 44

```
tagtgctcag tatttccaac gttctgttta tttaagatga aaattgctgt agttaataag    60
cacttcccca tgtcattaaa atgcttaagg attttttaatg accacataac agtccataat   120
atgattaaac cccaatttac tgaatcaatg ccatattgtt gggtctttag attgtctcct   180
tttgtttctg ctactgtgaa tgatcctgtg atgatcatct ttgtgtgtaa atctttgtcc   240
cctcgccccc tccccttta ttattttctt gggatagacc ccaggacaaa aggtagaaaa    300
gaacaaagtg ttaaaaaatt tcttgataca tagccacaga ttattttcct gaaagttcts   360
aacatttata actacgagca gtatgtaaga gagttatggt tggaatgatt ttaatgtctc   420
tggggaattt aacaacaaaa aaactttagg cttctttgga gagagacatg cccttaactc   480
caccccgccc tagaacagag acccagccca tccaagtcag cctccccagg tcctccacct   540
tcaaaacagg caaacgaaat catttcttga ataattggta ggcttcaagg tcagatgtt    599
```

<210> SEQ ID NO 45
<211> LENGTH: 641
<212> TYPE: DNA
<213> ORGANISM: Homo sapiens

<400> SEQUENCE: 45

```
tgctatgtcc agtttacaca taaggatgtg caaatccagc aggttagctg agctgcccag    60
```

```
gaatatccag gcaagaatga ccatattctg ataattactc aggcctctgc ctcatctccg    120
ctgscccccc gccccctgac tctcttctga gtgccagatt cagcctccat ttgaatgcca    180
aatagacagg aaattagcat gcccagaatc cacgtcttta gtgcactctc tccccagctc    240
caaacctgtt actgcttgtg ttcaacatct cagtaaagct caacaacatc gacccattac    300
ttaggcctca aaccttgggt ggcatcgtcg attgctcttt tctttcatac cccacattca    360
acccatcagc ccatcccaca ggcccaagtg tgtcctctct accttcaaag cgtgtgtggc    420
atccaccgct tatcaccacc tctgccatta ccactggagt ccagtgccat catctctcac    480
ttggatgtgg ccagagtgtc tttgctggtc tccttcttgc ttcctacctt tgtaacagcc    540
tatcatctat ctctggtctc catagctcac tcccatactt tgagagggcc tttgaaagcc    600
ttagacagat catatcacag acctctatac tgaaagtcgg g                        641

<210> SEQ ID NO 46
<211> LENGTH: 25
<212> TYPE: DNA
<213> ORGANISM: Homo sapiens

<400> SEQUENCE: 46
tgctatgtcc agtttacaca taagg                                          25

<210> SEQ ID NO 47
<211> LENGTH: 24
<212> TYPE: DNA
<213> ORGANISM: Homo sapiens

<400> SEQUENCE: 47
cccgactttc agtatagagg tctg                                           24

<210> SEQ ID NO 48
<211> LENGTH: 284
<212> TYPE: DNA
<213> ORGANISM: Homo sapiens

<400> SEQUENCE: 48
ccatctgtgg agcagagtca ctgaaaggaa atactggaaa tactggaagc cacttggtgt     60
tttatcaagg atgtgaggtt tcctggcaac tttgtcgcca tatcatcatc atcatcacca    120
tcatcatcat catcatcatc atcatcatca tcatcatcat catcatctgc cctttaagtt    180
ttctgcttgt ttagaaaaga aatttataca gagcccccag tagcagctgt aaggggggcag    240 gttcttggag cagcccatcc tcaacattct tgctgctgat ggaa                     284

<210> SEQ ID NO 49
<211> LENGTH: 20
<212> TYPE: DNA
<213> ORGANISM: Homo sapiens

<400> SEQUENCE: 49
ccatctgtgg agcagagtca                                                20

<210> SEQ ID NO 50
<211> LENGTH: 20
<212> TYPE: DNA
<213> ORGANISM: Homo sapiens

<400> SEQUENCE: 50
ttccatcagc agcaagaatg                                                20
```

```
<210> SEQ ID NO 51
<211> LENGTH: 145
<212> TYPE: DNA
<213> ORGANISM: Homo sapiens

<400> SEQUENCE: 51
tccacgcaga gaggatctaa atctggctct ttgcaattgc cttcatacat gtgcatacac        60
accacacaca cacacacaca cacacacaca cacacacaca cagacacata catatgcaca      120
caccccgact caatggagga ccctc                                             145

<210> SEQ ID NO 52
<211> LENGTH: 21
<212> TYPE: DNA
<213> ORGANISM: Homo sapiens

<400> SEQUENCE: 52
tccacgcaga gaggatctaa a                                                  21

<210> SEQ ID NO 53
<211> LENGTH: 20
<212> TYPE: DNA
<213> ORGANISM: Homo sapiens

<400> SEQUENCE: 53
gagggtcctc cattgagtcg                                                    20
```